(12) United States Patent
Groman et al.

(10) Patent No.: US 7,048,907 B2
(45) Date of Patent: May 23, 2006

(54) SYNTHESIS, COMPOSITIONS AND METHODS FOR THE MEASUREMENT OF THE CONCENTRATION OF STABLE-ISOTOPE LABELED COMPOUNDS IN LIFE FORMS AND LIFE FORM EXCRETORY PRODUCTS

(75) Inventors: Ernest V. Groman, Brookline, MA (US); Christopher P. Reinhardt, Worcester, MA (US)

(73) Assignee: BioPhysics Assay Laboratory, Inc., Worcester, MA (US)

( * ) Notice: Subject to any disclaimer, the term of this patent is extended or adjusted under 35 U.S.C. 154(b) by 179 days.

(21) Appl. No.: 10/060,652

(22) Filed: Jan. 30, 2002

(65) Prior Publication Data

US 2003/0059368 A1 Mar. 27, 2003

Related U.S. Application Data

(60) Provisional application No. 60/266,647, filed on Feb. 5, 2001.

(51) Int. Cl.
*A61K 49/00* (2006.01)

(52) U.S. Cl. ............... 424/9.2; 424/1.11; 424/1.65; 424/9.1; 534/7; 534/14

(58) Field of Classification Search ............... 424/1.11, 424/1.65, 9.1, 9.2, 9.3, 9.4, 9.5; 534/7, 10–16
See application file for complete search history.

(56) References Cited

U.S. PATENT DOCUMENTS

| | | | |
|---|---|---|---|
| 4,647,447 A | 3/1987 | Gries et al. | |
| 4,885,363 A | 12/1989 | Tweedle et al. | |
| 4,908,202 A | 3/1990 | Schulz | 424/9 |
| 5,071,775 A | 12/1991 | Snapka et al. | |
| 5,100,646 A | 3/1992 | Choyke et al. | |
| 5,275,801 A | 1/1994 | Niedballa et al. | |
| 5,277,895 A | 1/1994 | Platzek et al. | |
| 5,284,647 A | 2/1994 | Niedballa et al. | |
| 5,362,476 A | 11/1994 | Sherry et al. | |
| 5,647,363 A | 7/1997 | Rabito et al. | 128/659 |
| 5,674,467 A | 10/1997 | Maier et al. | |
| 5,676,923 A | 10/1997 | Platzek et al. | |
| 5,834,456 A | 11/1998 | Kiefer et al. | |
| 6,083,479 A | 7/2000 | Platzek et al. | |
| 6,548,822 B1 | 4/2003 | Morris et al. | 250/573 |
| 2003/0049202 A1 | 3/2003 | De Stasio et al. | 424/1.11 |

FOREIGN PATENT DOCUMENTS

| | | |
|---|---|---|
| EP | 0 730 873 A1 | 9/1996 |
| WO | WO 00/00204 | 1/2000 |

OTHER PUBLICATIONS

Akine et al. (1993). *Japanese J. of Cancer Research 84*. 841-843.
Awang et al. (1993). *J. of Labelled Compounds and Radiopharmaceuticals 33*. 941-948.
Awang et al. (1994). *Nuclear Medicine and Biology 21*. 905-909.
Bianchl et al. (1973). *J. of Nucl. Biology and Medicine 17*. 158-61.
Bohlen et al. (1994). *J. of Immunological Methods, 173*. 55-62.
Choyke et al. (1992). *Kidney International 41*: 1595-1598.
Dean et al. (1985). "Lange's Handbook of Chemistry. Section 3—Atomic and molecular structure," 3-21-3-98.
Elster et al. (1989). *Am. J. of Neuroradiology 10*. 1137-1144.
Fawdry et al (1985). *Eur. J. of Nuclear Medicine 11*. 7-12.
Funck-Bretano et al. (1987) *Revue Francaise D'Etudes Cliniques et Biologiques 12*, 790 English Abstract p. 798.
Helene (1995). *Veterinary Quaterly 17*. S36.
Ikeda et al. (1989). *J. of Radioanalytical and Nuclear Chem. 131*. 65-72.
Kale et al. (1990). *J. of the Indian Chem. Society 67*, 901-902.
Konks et al. (1964). *Database—Chemical Abstracts Service*, an: 60:80327.

(Continued)

*Primary Examiner*—Dameron L. Jones
(74) *Attorney, Agent, or Firm*—Lawson & Weitzen, LLP; Sonia K. Guterman

(57) ABSTRACT

Stable isotope labeling and neutron activation to measure biological functions are provided, as are the use and method of adding a chemical monitor to correct for neutron flux to sample vials prior to the addition of sample is presented, and the use of stable isotopes as a chemical bar code for vials and other items. Methods are provided also for measuring glomerular filtration rate and glomerular sieving function in a subject, and for measuring other physiological functions.

16 Claims, 8 Drawing Sheets

OTHER PUBLICATIONS

Matsumura et al. (1997). *Neurologia Medico-Chirurgica 37*. 327-331.
Milko et al. (1990). *Database—Medline US Nat'l Lib. Of Medicine*, an 74024757.
Moe et al. (1995). *Research in Veterinary Science 58*. 138-143.
Mombelli et al. (1969). *Radiologia Medica 55*. 242-7.
Shih et al. (1992). *Medical Physics, Am. Inst. Of Physics 19*, 773-744.
Vasil'eva et al. (2000). *Database —Chemical Abstracts Service*, an: 134:77301.
Agodoa et al. (1997). *Kidney International 52*: S-144-S-150.
Apperloo et al. (1996). *J. of the Am. Soc. of Nephrol.* 7:567-572.
Back et al. (1988). *J. of Pharmaceutical Sci. 77*: 765-767.
Barnas and Mayer (1997). *Kidney International 52*: S-78-S-80.
Benness et al. (1996). *Inv. Radiol. 31*: 211-217.
Blouch et al. (1997). *Am. J. Physiol. 42*: F430-F437.
Bocchetta et al. (1993). *J. of Cellular Physiol. 156*:601-609.
Chou et al. (1993). *Nucl. Med. Biol. 20*: 631-636.
Cohen et al. (1969). *Pediatrics 43*: 407-415.
Cul et al. (1997). *Antiviral Chemistry and Chemotherapy* 8:529-536.
de Belder and Granath (1973). *Carbohydrate Research 30*: 375-378.
de Caestecker et al. (1995). *Eur. J. of Gastroenterol. & Hepatol. 7*: 955-961.
Earp and O'Keefe (1981). *J. Clin. Invest. 67*: 1580-1583.
Eberstadt (1984). *International J. Urol & Nephrol. 16*:3-11.
Edwards and Deen (1995). *Am. J. Physiol.* 268:F736-F745.
Failey et al. (1979). *Anal. Chem. 51*: 2209-2221.
Farkkila et al. (1996). *Clinical Science 90*: 315-319.
Fujioka et al. (1999). *J. Clin. Gastroenterol. 28*: 329-333.
Gaspari et al. (1997). *Kidney International 52*: S-151-S-154.
Goeckeler et al. (1987). *J. Nucl. Med. 28*: 495-504.
Hulme(1975). *Contr. Nephrol. 1*: 3-8.
Josephson et al. (1990). *Magnetic Resonance Imaging 8*: 637-646.
Kakuta et al. (1997). *Nuclear Med. Comm. 18*: 937-942.
Kato et al. (1992). *Exp. Cell Res. 198*: 59-68.
Killian et al. (1994). *Radioactivity & Radiochemistry 5*: 34-41.
Kim et al. (1994). *Art. Cells, Blood Subs., and Immob. Biotech 22*: 619-624.
Kitchin and Brown (1995). *Anal. Biochem. 229*: 180-187.
Kokudo et al. (1999). *J. of Nucl. Med. 40*: 137-141.
Lang et al. (1997). *Transplantation 64*: 1585-1590.
Lauffer et al. (1985). *J. Comput. Assist. Tomogr. 9*: 431-438.
Lauffer (1987). *Chem. Rev. 87*: 901-927.
Leveille-Webster et al. (1996). *Hepatology 23*: 1631-1641.
Lufft et al. (1998). *Clin. Transplantation 12*: 409-415.
McCormick et al. (1973) *Gut 14*: 895-902.
Milkiewicz et al. (1997). *J. of Hepatology 27*: 1106-1109.
Millard et al. (1977). *Am. J. Physiol. 232*: H331-H334.
Nair et al. (1991). *J. of Biol. Chem. 266*: 567-573.
Neer et al. (1978). *Calcif Tiss. Res. 26*: 5-11.
Paumgartner (1986). *J. of Hepatology 2*: 291-298.
Perrone et al. (1992). *Clin. Chem. 38*: 1933-1953.
Popper "Hepatocellular Degeneration and Death", Ch. 45, in *The Liver: Biology and Pathobiology* eds. Arlas et al. Raven Press, New York (1982).
Potter (1998). *Dig. Dis. 16*: 118-124.
Prevot et al. (2000). *Pediatr. Nephrol. 14*: 370-375.
Reimer et al. (1992). *Radiology 182*: 565-569.
Remuzzi et al. (1987). *Am. J. Physiol. 253*: F318-327.
Rudberg and Nylander (1996). *Acta Radiologica 37*: 672-675.
Rustom et al. (1993). *Clinical Science 85*: 733-736.
Saini et al. (1987). *Radiology 162*: 211-216.
Sato et al. (1986). *J. Biochem. 100*: 1481-1492.
Sawamura et al. (1984). *Gastroenterology 87*: 1217-1221.
Scandling et al. (1992). *Adv. In Nephrol. 21*: 159-176.
Scott and Baxter (1996). *Endocrinology 137*: 3864-3870.
Sigman et al. (1965). *Inv. Urology 2*: 432-438.
Snapka et al. (1986). *Proc. Natl. Acad. Sci. USA 83*: 8939-8942.
Theilmann et al. (1991). *Transplantation 52*: 1020-1023.
Thilveris et al. (1991). *Nephron 57*: 470-476.
Tweedle "Relaxation Agents in NMR Imaging" in *Lanthanide Probes in Life, Chemical and Earth Sciences, Theory and Practice* eds. Bunzli and Choppin Elsevier, (1989).
Vera et al. (1995). *Acad. Radiol. 2*: 497-506.
Walser et al. (1988). *Kidney International 34*: 412-418.
Betebenner et al. (1991). *Bioconjugate Chem. 2*: 117-123.
Albert et al. *J. Lab. Clin. Med.*, 141:106-109 (2003).
Berthezéne et al. *Invest. Radiol.*, 27:346-351 (1992).
Brown et al. *Inorg. Chimica Acta*, 25:121-125 (1977).
Bulte et al. *Invest. Radiol.*, 33(11):841-845 (1988).
Database Chemabs, Accession No. 98:194239 (Zhao et al.), 1984.
Dini et al. *Mech. Aging Dev.*, 50:57-69 (1989).
Fleming et al. *Eur. J. Nucl. Ed.*, 18:391-395 (1991).
Galatola et al. *Gastroenterol.*, 100:1100-1105 (1991).
Groman et al. *Clin. Chem.*, 46(9):1519-1521 (2000).
Ha-Kawa et al. *Eur. J. Nucl. Med.*, 24:130-137 (1997).
Harding et al. *Eur. J. Cell Biol.*, 36:230-238 (1985).
Jakobsen et al. *J. Am. Chem. Soc.*, 104:7442-7452 (1982).
Kempka et al, *Exp. Cell Res.*, 176:38-48 (1988).
Kirmse et al. *Inorg. Chem.*, 23:3333-3338 (1984).
Knapp et al. *J. Nucl. Med.*, 21:258-263 (1980).
Kolb-Bachofen et al. *Carbohydrate Res.*, 213:201-213 (1991).
Mumper et al. *J. Nucl. Med.*, 33(3):398-402 (1992).
European Search Report for EP 02 71 9031, mailing date: Aug. 18, 2004.

SYNTHESIS, COMPOSITIONS AND METHODS FOR THE MEASUREMENT OF THE CONCENTRATION OF STABLE-ISOTOPE LABELED COMPOUNDS IN LIFE FORMS AND LIFE FORM EXCRETORY PRODUCTS

RELATED APPLICATION

This application claims priority to provisional patent application U.S. Ser. No. 60/266,647, filed Feb. 5, 2001, the contents of which are hereby incorporated by reference in entirety herein.

FIELD OF THE INVENTION

The invention relates to methods wherein, by recording the concentration or amount of one or more stable isotopically labeled xenobiotic compound containing an element detectable after neutron activation, this xenobiotic compound may be determined in a living subject in blood, serum, plasma, urine, fecal, biopsy, or other body fluid or composition.

BACKGROUND OF THE INVENTION

Neutron activation and stable isotope labeling allows for the detection of low amounts of molecules in biological systems, as shown in chromatographs and gel electrophoretograms (1) For many diagnostic and therapeutic applications, it can be important to detect small amounts of a molecule of interest in a biological sample. Present methods for detecting biological compounds or physiological processes of interest can lack the requisite sensitivity and non-toxicity for in vivo administration.

SUMMARY OF THE INVENTION

The invention is based in part on the discovery of highly sensitive stable isotope-containing compositions that allow for detection and measurement of small quantities of a biological molecule in samples taken from a subject. An embodiment of the invention features a composition comprising a compound having a structure X-M, wherein X is a chelator, M is an atom of a stable isotope of an element having a nucleus capable of capturing a neutron and subsequently emitting a photon, M is noncovalently bound to X, X being at a concentration at least as great as that of M, the composition having a counterion and a physiologically acceptable buffer. In general, the atom of the stable isotope M is selected from the group consisting of: $^{45}Sc$, $^{50}Cr$, $^{55}Mn$, $^{58}Fe$, $^{59}Co$, $^{63}Cu$, $^{103}Rh$, $^{113}Cd$, $^{114}Cd$, $^{113}In$, $^{115}In$, $^{123}Te$, $^{133}Cs$, $^{139}La$, $^{141}Pr$, $^{146}Nd$, $^{149}Sm$, $^{152}Sm$, $^{151}Eu$, $^{153}Eu$, $^{152}Gd$, $^{155}Gd$, $^{157}Gd$, $^{159}Tb$, $^{158}Dy$, $^{160}Dy$, $^{161}Dy$, $^{162}Dy$, $^{163}Dy$, $^{164}Dy$, $^{168}Yb$, $^{169}Tm$, $^{174}Hf$, $^{178}Hf$, $^{175}Yb$, $^{165}Ho$, $^{175}Lu$, $^{176}LU$, $^{181}Ta$, $^{185}Re$, $^{187}Re$, $^{190}Ir$, $^{193}Ir$, $^{196}Hg$, $^{202}Hg$, and $^{197}Au$. The counterion is, for example, meglumine (1-deoxy-1-methylamino-D-glucitol antimoniate). The chelator X can be selected from the group consisting of: diethylenetriaminepentaacetic acid (DTPA), diethylenetriamine-pentamethylenephosphonic acid (DTPMP), tetraazacyclododecanetetraacetic acid (DOTA) or a derivative of DOTA, ethylene-diaminetetraacetic acid (EDTA), tetraazacyclododecanetetrakis (methylene phosphonic acid) (DOTP), hydroxypropyl tetraazacylododecanetriacetic acid (HP-DO3A), diethylenetriaminetriacetic acid bismethylamide (DTPA-BMA), and MS-325. The concentration of X is between about 100 micromolar and about 1.5 molar.

In another embodiment, the invention features a method of preparing a pharmaceutical composition of a compound having a structure X-M, the method comprising: providing a solution having X and M, wherein X is a chelator, and M is an atom of a stable isotope of an element noncovalently bound to X and having a nucleus capable of capturing a neutron and subsequently emitting a photon, and the concentration of X is at least as great as that of M, the solution being aqueous and having a physiologically acceptable buffer; and sterilizing the solution. In a related embodiment of the method, M is selected from the group consisting of: $^{45}Sc$, $^{50}Cr$, $^{55}Mn$, $^{58}Fe$, $^{59}Co$, $^{63}Cu$, $^{103}Rh$, $^{113}Cd$, $^{114}Cd$, $^{113}In$, $^{115}In$, $^{123}Te$, $^{133}Cs$, $^{139}La$, $^{141}Pr$, $^{146}Nd$, $^{149}Sm$, $^{152}Sm$, $^{151}Eu$, $^{153}Eu$, $^{152}Gd$, $^{155}Gd$, $^{157}Gd$, $^{159}Tb$, $^{158}Dy$, $^{160}Dy$, $^{161}Dy$, $^{162}Dy$, $^{163}Dy$, $^{164}Dy$, $^{168}Yb$, $^{169}Tm$, $^{174}Hf$, $^{178}Hf$, $^{175}Yb$, $^{165}Ho$, $^{175}Lu$, $^{176}Lu$, $^{181}Ta$, $^{187}Re$, $^{187}Re$, $^{190}Ir$, $^{193}Ir$, $^{196}Hg$, $^{202}Hg$, and $^{197}Au$.

In yet another embodiment, the invention provides a method for quantifying by neutron activation an amount of a complex having a structure X-M, the method comprising: exposing each of the X-M complex and a standard to a neutron source, wherein X is a chelator and M is an atom of a stable isotope of an element having a nucleus capable of capturing a neutron and subsequently emitting a photon, and wherein the standard has a predetermined quantity of M, X-M and the standard being exposed to the neutron source at the same time, such that M emits a photon after capture of a neutron; detecting an emitted photon from each of X-M and the standard; and comparing an amount of photonic emissions from each of the X-M and the standard, thereby quantifying the amount of the complex having the structure X-M.

The invention in another embodiment features a method of determining the glomerular filtration rate (GFR) of a subject, comprising: administering a known quantity of a test substance to the subject, the test substance having at least one atom of a stable isotope of an element with a nucleus capable of capturing of a neutron and subsequently emitting a photon, the test substance being filtered by the kidneys and detectable by neutron activation analysis in a sample of a bodily fluid; obtaining at least one sample of a bodily fluid from the subject at least one predetermined time interval following administering the test substance; determining the amount of test substance in a volume of the at least one sample of the bodily fluid by neutron flux activation; and calculating the GFR from the amount of photon emission by the activated element, thereby determining the GFR of the subject.

In a related embodiment of this method, determining the amount of the test substance further involves comparing photon emission of the activated element in the sample of the bodily fluid to photon emission from a standard that includes the same stable isotope and is exposed to the same neutron flux. Another related embodiment of this method further comprises, prior to administering the compound to the subject, obtaining a sample from the subject of at least one bodily fluid for determining a baseline of concentration of the element. In other various related embodiments of the method, the test substance is selected, for example, from the group consisting of Sm-DTPA, La-DTPA, Lu-DTPA, Sm-DOTA, La-DOTA, and Lu-DOTA; the test substance is, for example, an iodinated contrast agent; the agent comprises iohexol or iothalamate; a dose of the test compound administered to the subject is about one μmol to about 0.5 mmol per kg body weight of the subject; the test compound is administered, for example, intravenously; the time interval can be about 10 to about 60 minutes; calculating the GFR an further involve using a computerized program; and obtaining a sample from the subject further comprises catheterizing the urethra of the subject.

The invention features in yet another embodiment a kit for measuring glomerular filtration rate in a subject, comprising: at least one vial of a test composition, the test composition having: a compound of structure X-M, wherein X is a chelator and M is an atom. of a stable isotope of an element having a nucleus capable of capturing a neutron and subsequently emitting a photon, M being noncovalently bound to the X, and a counterion, the compound being dissolved in a physiologically compatible solution; at least one sample container to collect a bodily fluid; and instructions for use. The kit in a related embodiment further comprising a data recording system. The kit can further comprise an internal standard monitor distributed into each of the sample containers.

In another embodiment, the invention provides a composition comprising at least one compound $\Omega_i$-$X_j$-$M_k$ and a counterion, wherein: each $\Omega_i$ is an organic compound having a molecular weight greater than about 50; each $X_j$ is at least one chelator covalently bound to each $\Omega_i$; and each $M_k$ is noncovalently bound to X and has a nucleus capable of capturing a neutron and subsequently emitting a photon and is an atom of a stable isotope of an element selected from the group consisting of $^{45}$Sc, $^{50}$Cr, $^{55}$M, $^{58}$Fe, $^{59}$Co, $^{63}$Cu, $^{103}$Rh, $^{113}$Cd, $^{114}$Cd, $^{113}$In, $^{115}$In, $^{123}$Te, $^{133}$Cs, $^{139}$La, $^{141}$Pr, $^{146}$Nd, $^{149}$Sm, $^{152}$Sm, $^{151}$Eu, $^{153}$Eu, $^{152}$Gd, $^{155}$Gd, $^{157}$Gd, $^{159}$Tb, $^{158}$Dy, $^{160}$Dy, $^{161}$Dy, $^{162}$Dy, $^{163}$Dy, $^{164}$Dy, $^{168}$Yb, $^{169}$Tm, $^{174}$Hf, $^{178}$Hf, $^{175}$Yb, $^{165}$Ho, $^{175}$Lu, $^{176}$Lu, $^{181}$Ta, $^{185}$Re, $^{187}$Re, $^{190}$Ir, $^{193}$Ir, $^{196}$Hg, $^{202}$Hg, and $^{197}$Au, wherein each $M_k$ is distinct in identity; i, j, and k each being a number from 1 to 8, wherein i is at least equal to k.

In another embodiment, the invention provides a composition comprising at least one compound $\Omega_i$-$X_j$-$M_k$, at least one compound $\Psi$-N, and a cationic counterion, wherein: each $\Omega$ is an organic compound having a molecular weight greater than about 50; each X is at least one chelator covalently bound to $\Omega$ and noncovalently bound to M; $\Psi$ is a chelator noncovalently bound to N; N is different from M, N and M each being an atom of a stable isotope of an element selected from the group consisting of $^{45}$Sc, $^{50}$Cr, $^{55}$Mn, $^{58}$Fe, $^{59}$Co, $^{63}$Cu, $^{103}$Rh, $^{113}$Cd, $^{114}$Cd, $^{113}$In, $^{115}$In, $^{123}$Te, $^{133}$Cs, $^{139}$La, $^{141}$Pr, $^{146}$Nd, $^{149}$Sm, $^{152}$Sm, $^{151}$Eu, $^{153}$Eu, $^{152}$Gd, $^{155}$Gd, $^{157}$Gd, $^{159}$Tb, $^{158}$Dy, $^{160}$Dy, $^{161}$Dy, $^{162}$Dy, $^{163}$Dy, $^{164}$Dy, $^{168}$Yb, $^{169}$Tm, $^{174}$Hf, $^{178}$Hf, $^{175}$Yb, $^{165}$Ho, $^{175}$Lu, $^{176}$Lu, $^{181}$Ta, $^{185}$Re, $^{187}$Re, $^{190}$Ir, $^{193}$Ir, $^{196}$Hg, $^{202}$Hg, and $^{197}$Au, each M and N, independently, having a nucleus capable of capturing a neutron and subsequently emitting a photon; and i, j and k are independently each a number from 1 to about 8.

In another embodiment, the invention provides a composition comprising: a compound $\Omega_i$-M and a cationic counterion, wherein: each $\Omega$ is an organic compound having a molecular weight greater than about 50, i being a number from 1 to about 8; and M is an atom of a stable isotope of an element selected from the group of elements consisting of $^{36}$S, $^{74}$Se, $^{79}$Br, $^{81}$Br, $^{107}$Ag, $^{109}$Ag, $^{127}$I, $^{197}$Au, $^{190}$Pt, and $^{196}$Hg, wherein M is covalently bound to $\Omega$ and has a nucleus capable of capturing of a neutron and subsequently emitting a photon. In various related embodiments of this composition, the at least one $\Omega_i$-X-$M_i$ compound differs in molecular weight range from the other compounds, the $\Omega_i$-X-$M_i$ compounds having the same net charge; the $\Omega_i$-X-$M_i$ compounds have different net charges and about the same molecular weight; and $\Omega_i$ is a polymer.

In various additional related embodiments of this composition, the polymer is selected from the group consisting of a polysaccharide, a polypeptide, and a polynucleotide; the polysaccharide is a ficoll, a dextran, a pullulan, a starch, or a hydroxyethylstarch; the polypeptide is covalently attached to a polyethylene glycol polymer; and the non-covalently bound chelator is a bile acid compound. In various additional related embodiments of this composition, the bile acid compound is selected from the group consisting of cholic acid, cholic acid taurine, chenodeoxycholic, deoxycholic acid, homocholic acid taurine, and lithocholic acid; the bile acid compound is a synthetic derivative of a bile acid; the non-covalently bound chelator is a drug or a drug metabolite; $\Omega_i$ is selected from the group consisting of a hormone and a hormone antagonist; $\Omega_i$ is a steroid hormone; and the non-covalently bound chelator is selected from the group consisting of an antibiotic, a tranquilizer, a vitamin, a narcotic, a cannabinoid, a barbiturate, and an alkaloid.

An embodiment of the invention also provides a composition comprising a plurality of colloids having the structure Y—$O_u$-$M_t$ and a cation counterion, the composition being suspended in a physiologically compatible buffer, wherein: Y is a polymer having a molecular weight greater than about 1000; O is oxygen and u is a number between zero and about 200; and each M is an atom selected from the group of stable isotopes capable of capturing a neutron, thereby becoming unstable and emitting a photon having a characteristic energy spectrum, the photon being selected from the group consisting of a gamma photon, an x-ray photon or a prompt photon, t being an integer from 1 to about 10. In a related embodiment, each colloid among the plurality has a distinct molecular weight and is uniquely associated with a distinct M.

An embodiment of the invention provides a method for quantifying by neutron activation an amount of at least one compound $\Omega_i$-$X_j$-$M_k$, wherein each $\Omega_i$ is a unique organic compound having a molecular weight greater than about 50; each $X_j$ is at least one chelator covalently bound to $\Omega_i$; and each $M_k$ is an atom of a stable isotope of an element and is distinct in identity and has a nucleus capable of capturing neutrons and thereby emitting photons, and i, j, and k are each numbers from 1 to 8, i being at least as great as k, the method comprising: exposing a first container having $\Omega_i$-$X_j$-$M_k$ and a second container having a standard known quantity of $M_k$ to a neutron source using the same neutron field, such that $\Omega_i$-$X_j$-$M_k$ and the $M_k$ standard capture neutrons and emit photons, wherein each $M_k$ is selected from the group consisting of $^{45}$Sc, $^{50}$Cr, $^{55}$Mn, $^{58}$Fe, $^{59}$Co, $^{63}$Cu, $^{103}$Rh, $^{113}$Cd, $^{114}$Cd, $^{113}$Cd, $^{113}$In, $^{115}$In, $^{123}$Te, $^{133}$Cs, $^{139}$La, $^{141}$Pr, $^{146}$Nd, $^{149}$Sm, $^{152}$Sm, $^{151}$Eu, $^{153}$Eu, $^{152}$Gd, $^{155}$Gd, $^{157}$Gd, 159Gd, $^{158}$Dy, $^{160}$Dy, $^{161}$Dy, $^{162}$Dy, $^{163}$Dy, $^{164}$Dy, $^{168}$Yb, $^{169}$Tm, $^{174}$Hf, $^{178}$Hf, $^{175}$Yb, $^{165}$Ho, $^{175}$Lu, $^{176}$Lu, $^{181}$Ta, $^{185}$Re, $^{187}$Re, $^{193}$Ir, $^{196}$Hg, $^{202}$Hg and $^{197}$Au; detecting resulting photon emissions; and comparing photon emissions of $\Omega_i$-$X_j$-$M_k$ with photon emissions of the standard, thereby quantifying the amount of at least one compound $\Omega_i$-$X_j$-$M_k$.

An embodiment of the invention provides a method of evaluating the rate of at least one physiological process in a subject, the method comprising: administering at least one test composition to a subject, wherein each test composition is differently labeled with one of the group of stable isotopes of one or more elements; obtaining a plurality of samples of a bodily fluid from the subject, the samples being obtained at different times after administering the composition; determining by neutron activation the amount of the at least one test composition in a volume of the samples; and calculating the rate of change of concentration over time of the composition in the bodily fluid, thereby evaluating the rate of the physiological process in the subject. In a related embodiment of this method, the rate of the physiological process is the glomerular filtration rate.

In various additional related embodiments of the method, the physiological process is the glomerular integrity rate; the rate of the at least one physiological process is a glomerular filtration rate and a glomerular integrity rate; the rate of change of concentration of the at least one test composition is glomerular selectivity according to size of the test composition; the rate of change of concentration of the at least one test composition is glomerular selectivity according to charge of the test composition; the physiological process is at least one hepatic function; the physiological process is at least one gastrointestinal function; and the rate of the physiological process is evaluating absorption of a bile acid compound.

In related embodiments of the method, evaluating the rate of the physiological process is evaluating cirrhosis; further, evaluating the rate of change of the physiological process is evaluating liver function after liver transplantation.

A featured embodiment of the invention provides a kit for measuring glomerular integrity rate, comprising: a test composition X-M and a counterion in a physiologically compatible solution wherein X is a chelator noncovalently bound to M, and M is an atom of a stable isotope of an element having a nucleus capable of capturing a neutron and subsequently emitting a photon; at least one sample container to collect at least one samples of a bodily fluid; instructions for use; and a data recording system.

An embodiment of the invention provides a composition for lot labeling a plurality of sample containers, the composition comprising at least one stable isotope of an element and a binding agent, wherein the binding agent maintains the stable isotope in the container, the stable isotope having a nucleus capable of capturing a neutron and subsequently emitting a photon.

Accordingly, the binding agent is selected from the group consisting of: a polyurethane, a wax, an oil based adhesive, an organic solvent, a water based adhesive, an aqueous solvent, an acrylic and a plastic.

An embodiment of the invention provides a method for monitoring neutron flux variation within a set of samples, the method comprising: providing a lot having a plurality of sample containers, each container having a predetermined amount of a first stable isotope; adding a test sample containing a second stable isotope to each of the containers, wherein the first and second stable isotopes are different and are selected from the group consisting of $^{45}$Sc, $^{50}$Cr, $^{55}$Mn, $^{58}$Fe, $^{59}$Co, $^{63}$Cu, $^{103}$Rh, $^{113}$Cd, $^{114}$Cd, $^{113}$In, $^{115}$In, $^{123}$Te, $^{133}$Cs, $^{139}$La, $^{141}$Pr, $^{146}$Nd, $^{149}$Sm, $^{152}$Sm, $^{151}$Eu, $^{153}$Eu, $^{152}$Gd, $^{155}$Gd, $^{157}$Gd, $^{159}$Tb, $^{158}$Dy, $^{160}$Dy, $^{161}$Dy, $^{162}$Dy, $^{163}$Dy, $^{164}$Dy, $^{168}$Yb, $^{169}$Tm, $^{174}$Hf, $^{178}$Hf, $^{175}$Yb, $^{165}$Ho, $^{175}$Lu, $^{176}$Lu, $^{181}$Ta, $^{185}$Re, $^{187}$Re, $^{190}$Ir, $^{193}$Ir, $^{196}$Hg, $^{202}$Hg, and $^{197}$Au; exposing the resulting containers to a neutron source; and comparing the resulting photon emissions from each of the first and second stable isotopes in each container of the lot to monitor neutron flux variation within the set of samples.

An embodiment of the invention provides a method for associating each of a plurality of tubes with a particular lot, the method comprising: providing a plurality of containers having a predetermined amount of a first stable isotope composition, M, for identification of the lot, and a known amount of a second stable isotope composition, N, to monitor neutron flux variations, wherein M and N are different and are selected from the group consisting of $^{36}$S, $^{45}$Sc, $^{50}$Cr, $^{51}$V, $^{55}$Mn, $^{58}$Fe, $^{59}$Co, $^{63}$Cu, $^{75}$As, $^{79}$Br, $^{81}$Br, $^{103}$Rh, $^{107}$Ag, $^{109}$Ag, $^{113}$Cd, $^{114}$Cd, $^{113}$In, $^{115}$In, $^{123}$Te, $^{121}$Sb, $^{123}$Sb, $^{123}$Te, $^{127}$I, $^{133}$Cs, $^{139}$La, $^{141}$Pr, $^{146}$Nd, $^{149}$Sm, $^{152}$Sm, $^{151}$Eu, $^{153}$Eu, $^{152}$Gd, $^{155}$Gd, $^{157}$Gd, $^{159}$Tb, $^{158}$Dy, $^{160}$Dy, $^{161}$Dy, $^{162}$Dy, $^{163}$Dy, $^{164}$Dy, $^{165}$Ho, $^{168}$Yb, $^{169}$Tm, $^{174}$Hf, $^{178}$Hf, $^{175}$Yb, $^{175}$Lu, $^{176}$Lu, $^{181}$Ta, $^{184}$OS, $^{185}$Re, $^{186}$W, $^{187}$Re, $^{190}$Ir, $^{190}$Pt, $^{193}$Ir, $^{196}$Hg, $^{206}$Hg, and $^{197}$Au, the containers configured to receive a test sample, wherein the test sample is substantially free of M and N; exposing the containers to a neutron source; and detecting the resulting photon emissions at spectra characteristic of M and N, so as to associate each tube of the plurality of tubes with the predetermined quantity of the first stable isotope, for identification of the lot. The phrase, "substantially free" for example of M and N, shall mean that the sample is at least about 90% free, for example at least about 95% free, for example at least about 98% free, and for example, at least about 99% free of M and N, on a solute basis, or on a dry weight basis.

| Energy (kev) | Isotope |
|---|---|
| 103.2 | $^{152}$Sm (n,γ) $^{153}$Sm |
| 112.95 | $^{176}$Lu (n,γ) $^{177}$Lu |
| 208.36 | $^{176}$Lu (n,γ) $^{177}$Lu |
| 295.95 | $^{191}$Ir (n,γ) $^{192}$Ir |
| 308.46 | $^{191}$Ir (n,γ) $^{192}$Ir |
| 316.50 | $^{191}$Ir (n,γ) $^{192}$Ir |
| 328.5 | $^{193}$Ir (n,γ) $^{193}$Ir |
| 338.8 | $^{193}$Ir (n,γ) $^{193}$Ir |
| 411.8 | $^{197}$Au (n,γ) $^{198}$Au |
| 554.3 | $^{81}$Br (n,γ) $^{82}$Br |
| 559.1 | $^{75}$As (n,γ) $^{76}$As |
| 564.1 | $^{121}$Sb (n,γ) $^{122}$Sb |

Figure 3:
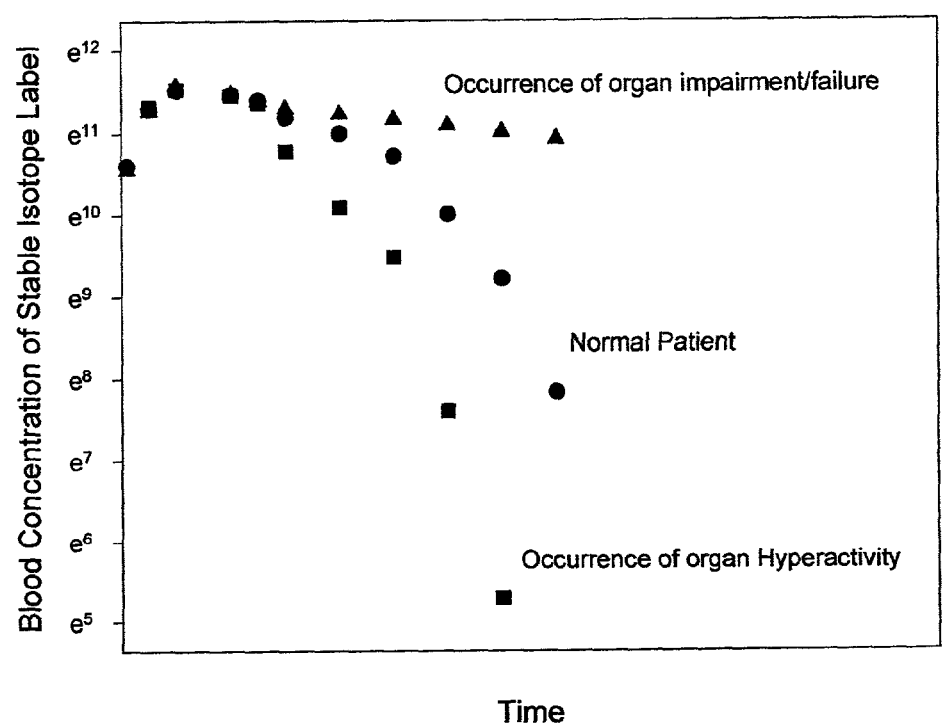

FIG. 3 is a graph that illustrates the relationship between the blood concentration of a test compound, for example, to test glomular filtration rate over time following bolus injection of the compound. The blood concentration of the test compound will increase sharply and then decrease over time until reaching its preinjection concentration in a normal subject. When organ impairment, for example, kidney impairment occurs, the blood concentration of the test compound will decrease more slowly and take a longer time to reach preinjection levels. In rare cases organ function may be increased compared to normal function in which case test substance blood concentration will decline more rapidly than in a normal subject. The time scale illustrates points from an 8 hour total time course.

Figure 4:
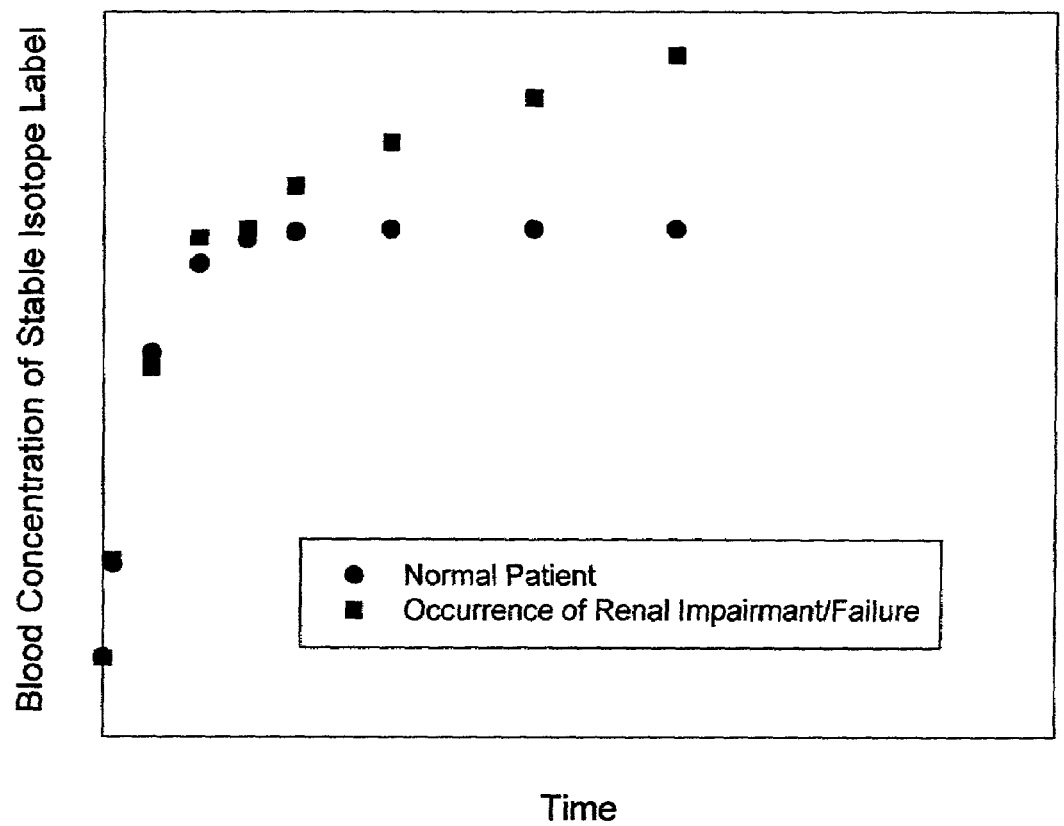

FIG. 4 is a graph that illustrates the relationship between the blood concentration of a test compound and time following injection by constant infusion. Upon initiation of the infusion the measured blood concentration of the test compound will increase sharply, and will then become constant for a normal patient at steady state where the excretion rate equals the rate of infusion. When organ impairment occurs, the value of a test compound will continue to increase over time. The time scale illustrates points from an 8 hour total time course.

Figure 5:
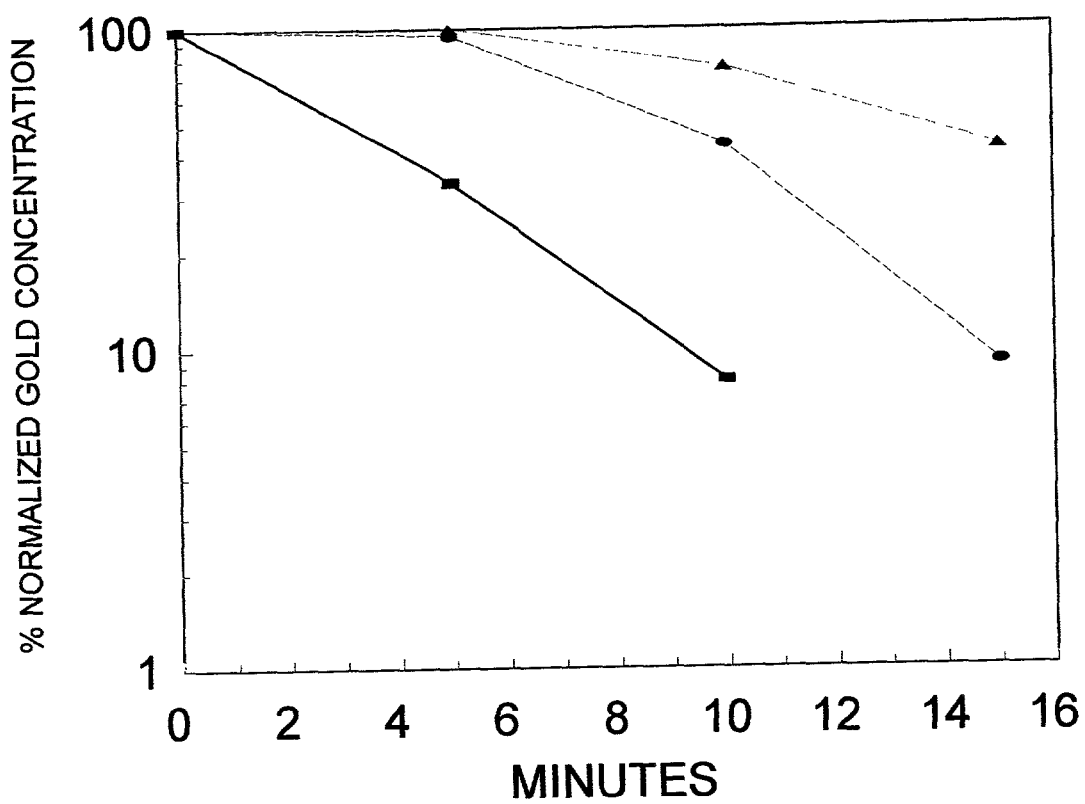

FIG. 5 is a graph that shows the kinetics of removal from blood of 20 nm diameter gold colloid particles coated with lactosylated albumin or albumin. Rats were injected with gold colloid coated with lactosylated albumin in the absence (squares) or presence of asialofetuin (ovals), or with gold colloid coated with albumin (triangles). Samples of blood were removed at the indicated times and the percent of gold remaining in the blood (normalized for gold concentration at time equal to zero) was determined using neutron activation analysis. Values presented in the figure represent the mean value obtained with three rats.

Figure 6:
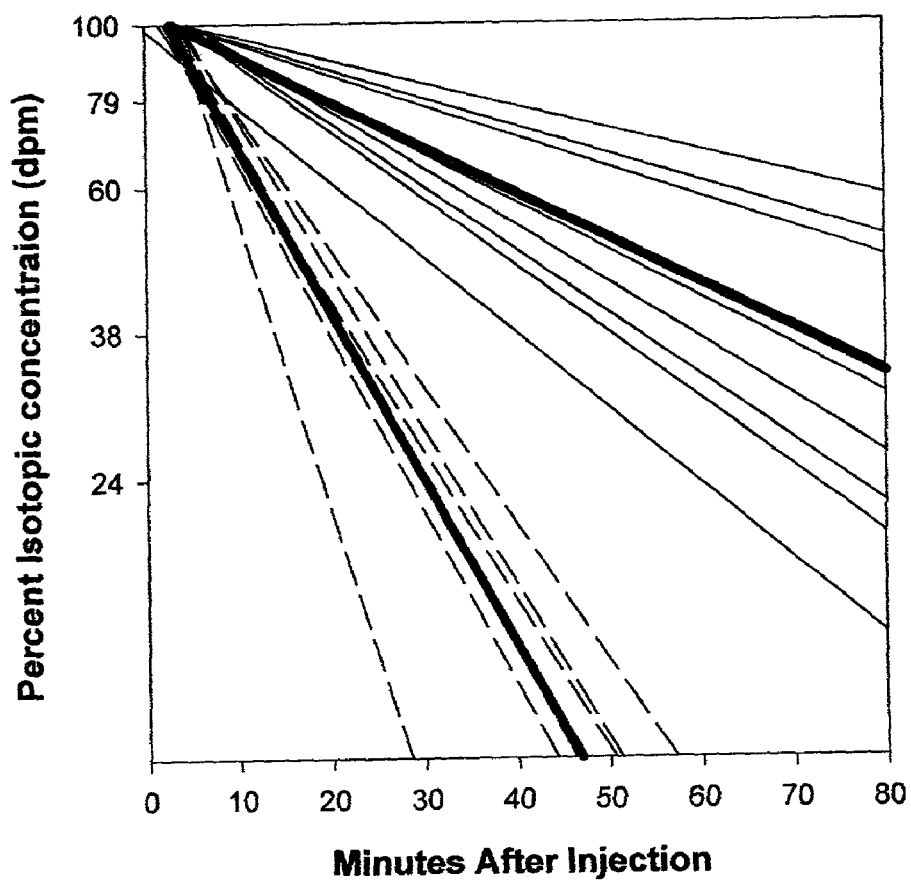

FIG. 6 is a graph that predicts clearance of plasma samarium for 60-minutes after injection of Sm-cholic acid. Solid lines represent samples obtained from patients with cirrhosis, and have a mean $t_{1/2}$ of 120.7±53.9 minutes. Dashed lines represent subjects having a mean $t_{1/2}$ of 30.7±6.2 minutes. Cirrhosis verses normal group is p=0.006. The bold lines represent the respective mean values of each of the two groups.

Figure 7:
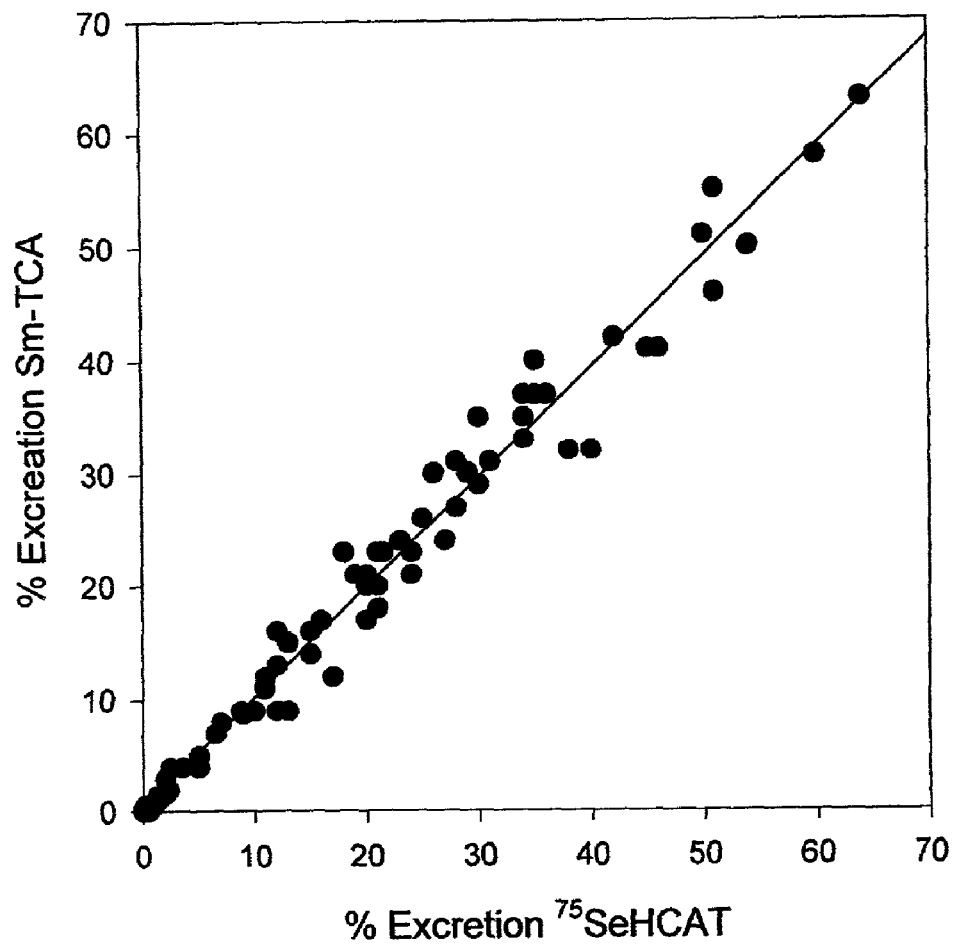

FIG. 7 is a graph showing daily excretion of Sm-TCA and Se-CAT tracers of bile acid, expressed as percentage of the administered doses. The paired values as measured by both tracers of detection is represented by the equation y=0.97x+0.52, with a coefficient of correlation of r=0.99.

Figure 8:
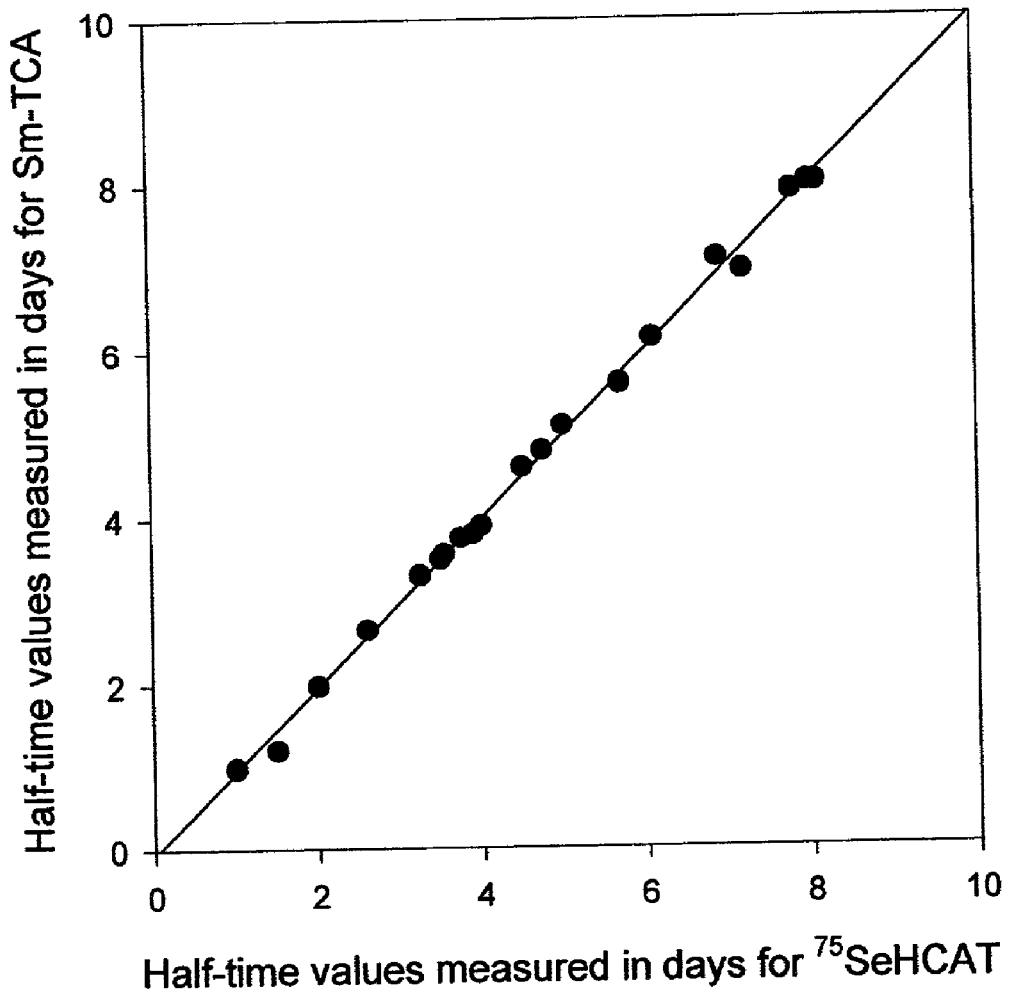

FIG. 8 is a graph showing half time of elimination of bile acid tracers. The paired values (in days) as measured for both tracers is represented by the equation y=1.01x−0.05, with a coefficient of correlation of r=1.00.

DESCRIPTION OF SPECIFIC EMBODIMENTS

A method is provided for evaluating the clearance rate of a xenobiotic compound from a living subject, thereby providing a noninvasive method for determining the status of the (excretory) organs of the subject and a method for determining the proper dosing regimen of a pharmacologically active compound to be administered to the subject. Also provided are compositions of xenobiotics containing stable isotopes, both of natural abundance and enriched, that can be subject to neutron activation and thereby used to determine their amount and concentration.

More specifically, an embodiment of this invention relates to a method of determining the glomerular filtration rate (GFR) and the glomerular sieving function (GSF) of a subject that comprises determining the concentration of a stable isotope in serum and urine samples obtained from a subject given a substance detectable by neutron activation, e.g., Sm-DTPA. The stable-isotope labeled substances are filtered by the kidney in accordance with specified formulas. More particularly, an embodiment of this invention provides a method that compares the concentration of the stable isotope before and after its administration to a patient. The present method is non-radioactive, safe to the patient and the health practitioner, extremely accurate, and easy to perform.

Stable Isotope Labeling.

"Stable isotope labeling" means conjugating a suitable stable isotope with a molecule or chemical entity of interest. See (1) and U.S. Pat. No. 5,071,775, which is incorporated herein by reference. Representative stable isotopes are listed in Table 1. Molecules and chemical entities of interest include but are not limited to chelates, proteins, nucleic acids, lipids, polysaccharides, and colloids. Stable isotopes do not emit radiation and normally can only be measured on a mass basis. Some stable isotopes, however, can be exposed to neutrons and upon capture of a neutron by the nucleus of the atom, become thereby unstable. The newly formed unstable atom will de-excite by emitting an energetic particle such as an electron or photon. The emitted photon can then be measured using high-resolution gamma spectroscopy.

Elements that are found only in trace amounts in biological tissues are best suited for stable isotope labeling and neutron activation. Examples of such trace elements include samarium, lanthanum, and gold. Samarium and lanthanum may be combined with biologicals through the use of chelators that are covalently attached to the biological. Gold serves best as a stable colloid coated with the biological reagent. Stable isotopes do not emit radiation but after neutron activation, can be detected in blood samples and other isolated tissues. The advantage of the use of stable isotopes for biological measurements is their sensitivity, absence of radiation, and the ability to measure multiple elements simultaneously.

Stable isotopes may be used in their natural abundance, or as enriched isotopes. Use of enriched isotopes in some instances allows the use of two or more isotopes of the same element as labels that can be assayed simultaneously. For instance, two isotopes of antimony, antimony 121 and antimony-123, provide an example of an element with two isotopes that can serve as stable isotope labels.

Quantitation of Stable Isotopes.

Quantitation of stable isotopes typically, but not always, includes three steps: activating the stable isotope by exposure to a neutron field, allowing a time interval of differential isotopic decay during which certain omnipresent isotopes decay, and monitoring of emission after a time period to measure photonic emissions. Activating stable isotopes is accomplished by exposure to neutrons generated typically by about a 0.1 to a 20 megawatt nuclear reactor, for example, a 1 to 20 megawatt nuclear reactor, certain isotopes such as californium, or an electronic source such as a particle accelerator. Exposure varies from about 5 to about 120 minutes, for example, from about one to about 5 minutes, from about 5 to about 15 minutes, from about 15 minutes to about 60 minutes, and from about 60 minutes to about 90 minutes. A 15 minute exposure is usually used as this provides sufficient neutron exposure while allowing adequate time to manipulate the next round of samples for exposure. Increased sensitivity of detection of stable isotope can be gained by increased time of exposure to the neutron field. A "neutron source" as used herein means any device that produces a field of neutrons, such as a nuclear reactor having a range of about 0.1 to 20 megawatts, an isotopic source, and an electronic source.

A "differential decay period" allows short-lived omnipresent isotopes, such as sodium, to decay, leaving longer lived isotopes of interest in a better medium to be measured with a lower background. This decay period generally is from about 1 to about 5 days, depending upon the relative amounts of each of the sodium and the isotopes of interest. During the measurement of prompt photons, the differential decay period is omitted.

Depending upon the type of isotope exposed to neutrons, three types of photonic emissions are produced (Table 1). These are gamma rays, x-rays, and prompt photons whose emission energy ranges are about 60–2500 kev, about 0.005–60 kev, and about 100–20000 kev, respectively. The half-lives for the various isotopes and associated half-lives are also included in Table 1. All of these photons can be detected using a germanium crystal photonic detector that is able to accumulate photonic emission events across a wide energy range. An example of the level of resolution obtainable with such a detector is presented in FIG. 2. Improved resolution and sensitivity of detection can be obtained by using a Compton suppressed germanium detector. Accumulation of photonic emissions is usually referred to as "counting", and the period of counting is typically about 1 to about 10 minutes. Longer counting times can be used to increase the sensitivity of detection.

Detection of photo emissions is achieved using a solid state crystal such as a germanium crystal, or using a scintillation detector such as a sodium iodine crystal. Further, photon detection is accomplished using Compton suppression alone, or Compton suppression operation in coincidence mode.

The amount or concentration of isotopes of interest can be determined using a standard curve, which is generated using a separate set of tubes containing known amounts of the isotopes of interest, which are exposed to the same neutron field and treated in the same way as the samples of interest.

TABLE 1

List of stable isotopes useful for neutron activation and biological applications*.

| Element | Isotope | Abundance | Cross-Section (barns) Thermal | Fast | Half-live (day) | Detection Mode |
|---|---|---|---|---|---|---|
| Antimony | Sb-121 | 57.30 | 5.9 | 200 | 2.72 | INAA |
|  | Sb-123 | 42.7 | 4.0 | 130 | 60.2 | INAA |
| Lanthanum | La-139 | 99.1 | 9.0 | 12.0 | 1.68 | INAA |
| Samarium | Sm-149 | 13.8 | 40000 | 3100 |  | PNAA |
|  | Sm-152 | 26.7 | 208 | 3000 | 1.929 | INAA |
| Europium | Eu-151 | 47.8 | 924 | 5800 | 4942.1 | INAA |
|  | Eu-153 | 53.2 | 350 | 1500 | 3136.45 | INAA |
| Gadolinium | Gd-157 | 15.65 | 255000 | 800 |  | PNAA |
| Tellurium | Te-122 | 2.6 | 2.4 | 80 | 119.7 | INAA |
| Dysprosium | Dy-161 | 18.9 | 580 | 1100 |  | PNAA |
|  | Dy-162 | 25.5 | 1800 | 2800 |  | PNAA |
|  | Dy-163 | 24.9 | 130 | 1600 |  | PNAA |
|  | Dy-164 | 28.2 | 1700 | 1000 | 0.1 | INAA |
| Lutetium | Lu-176 | 2.59 | 2300 | 1200 | 6.68 | INAA |
| Holmium | Ho-165 | 100 | 61 | 680 | 1.117 | INAA |
| Rhenium | Re-185 | 37.4 | 112 | 1700 | 3.777 | INAA |
| Hafnium | Hf-174 | 0.16 | 530 | 410 | 70 | INAA |
|  | Hf-178 | 27.3 | 50 | 300 | 25.1 | INAA |
|  | Hf-180 | 35.1 | 13 | 35 | 42.4 | INAA |
| Iridium | Ir-191 | 37.3 | 920.14 | 0 | 73.83 | INAA |
|  | Ir-193 | 62.7 | 112 | 1400 | 170 | INAA |
| Iodine | I-127 | 100 | 6.2 | 150 | 25 | INAA |
| Gold | Au-197 | 100 | 98.7 | 1550 | 2.7 | INAA |
| Ytterbium | Yb-168 | 0.13 | 2300 | 21000 | 32.03 | INAA |
|  | Yb-174 | 31.8 | 120 | 60 | 4.19 | INAA |

*4th Edition Chart of the Nuclides a General Electric Company Publication. INAA = Instrumental neutron activation analysis; PNAA = Prompt neutron activation analysis.

Neutron Activation Technology and its Application to Medicine.

Neutron activation analysis can provide the research and clinical communities with capabilities not readily available with other assay technologies. Neutron activation is well known for its excellent sensitivity and elemental specificity for the simultaneous measurement of trace elements. (2) This offers the potential of being able to measure multiple isotopic tracers per assay. Neutron activation analysis provides the research and clinical communities with capabilities not readily available with other assay technologies.

Unlike techniques such as MR imaging or NMR spectroscopy that can only measure (the effect of) one contrast agent at a time, stable isotope labeling and neutron activation analysis can measure multiple labels simultaneously. Unlike optical lasers, neutrons can penetrate solid tissue and opaque-liquid samples, thereby providing an assay that is completely self-contained and requires minimal sample preparation. Unlike other element detection methods, such as atomic absorption spectrophotometry, neutron activation is not chemically or physically destructive. Therefore, samples can be archived, re-assayed, and/or undergo additional chemical analysis following neutron activation. Unlike most optical tracers, many stable biologically-rare isotopes are nontoxic and can be safely used in human subjects, including pregnant women and pediatric subjects.

Typically only the ex vivo samples of interest are activated; thus neutron activation can significantly reduce occupational and patient exposure to radiation and reduce the amount of low-level radioactive waste generated, e.g. gloves, protective clothing, animal carcasses, etc. Stable isotopes do not undergo radioactive decay or cause radiokinetics. Stable isotope labeled research and clinical products will have a significantly longer shelf-life compared to many other competing labeling methods.

Neutron activation has been used in conjunction with enriched or biologically-rare isotopes, as substitutes for radioactive isotopes in laboratory experiments (1, 3) and in clinical applications. (4, 5) Kitchin et al. (3), for example, successfully used neutron activation to measure iodine and bromine for the assay of 5-iodo-2'-deoxyuridine and 5-bromo-2'-deoxyuridine as DNA precursors for determination of cell mitosis and death rates. Compared to each of immunocytochemistry and fluorescent-activated cell sorting, neutron activation-based studies of DNA synthesis were able to evaluate more cells per assay (up to $10^5$ more) due to the elimination of signal quenching errors associated with both beta-radiation and fluorescent counting, and the method required less labor and in-house laboratory equipment. In addition, this technique offered improved accuracy and precision, with coefficients of variation as low as about 3 to about 5% compared to both immunocytochemistry and flow-activated cell sorting. Recently, Chou et al. (4) refined a neutron activation technique for the clinical assay of protein-bound iodine in blood serum samples. The measurement of protein-bound iodine, as well as the assay of T4 and T3, is a conventional clinical test of thyroid function. This refined neutron activation technique provided a simple and highly sensitive assay (down to a few ppb), while avoiding systematic and temperature-dependent errors associated with traditional clinical analytical techniques.

General Principles Underlying Neutron Activation.

Figure 1:
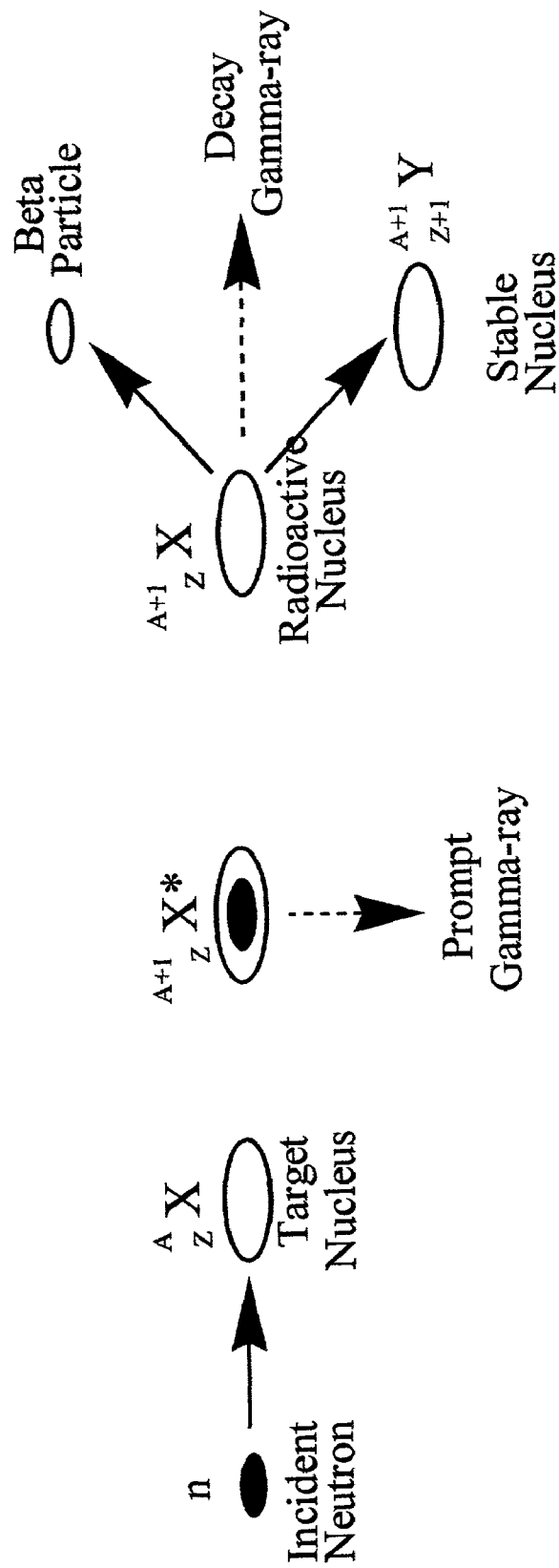
FIG. 1 is a schematic design of the general principle of neutron activation.

The general principle underlying neutron activation is that an incident neutron is captured by an atom (the parent nuclide) forming a radioactive nucleus (the daughter nuclide). As shown in FIG. 1, two modes of detection are often possible following neutron capture. The first is the measurement of the prompt gamma ray. This method is called Prompt Neutron Activation Analysis (PNAA). The half-life of this emission is usually under one second (see Table 1 for a few examples). The second method, and often more desirable for many of our applications, is to measure the decay of the resulting, radioactive daughter nuclide. This method is called Instrumental Neutron Activation Analysis (INAA).

With INAA detection, an ideal radioactive nucleus for use as a label is short-lived and emits a gamma ray during the decay process (6). The energy of the gamma ray is discrete and distinct for each stable atom. Specialized, high-resolution detection equipment can then be used to identify and measure the emitted gamma ray. The number of emitted gamma rays is directly proportional to the total mass of the parent isotope, and therefore is proportional to the total concentration of the labeled research product contained in the sample. In practice, a sample is exposed to a flux of neutrons, $\phi$, for a given time, t. The specific activity, S, induced in any parent nuclide can be calculated from the Formula:

$$S = 6.02 \times 10^{23} \phi \sigma f A^{-1} \{0.5\}^{t_1/t_{1/2}} \{1 - (0.5)^{t/t_{1/2}}\}$$

where: S is specific activity in disintegrations per unit mass ($s^{-1} kg^{-1}$), $\phi$ is flux of neutrons in $m^{-2} s^{-1}$, $\sigma$ is cross-section for neutron interaction with parent nuclide ($m^2$), f is fractional abundance of the parent nuclide, A is atomic weight of the parent element, $t_1$ is time between activation and counting (hours), t is activation period (hours), and $t_{1/2}$ is half-life of daughter nuclide (in hours).

The sensitivity of any nuclear reaction can be estimated using Equation 1. For samarium, the potential reaction is $^{152}Sm(n, \gamma)^{153}Sm$; $t^{1/2}$ is 1.93 d. Therefore, using a flux of $2.0 \times 10^{17}$ $m^{-2}$ $s^{-1}$ and an irradiation time of 30-minutes followed by a decay period of 2-days, a specific activity of $1.5 \times 10^{13}$ disintegrations $s^{-1}$ $kg^{-1}$ is obtained for $^{153}Sm$. Conservatively, this technique can determine less than $10^{-14}$ kg (0.01 ng) of samarium. Therefore, this assay may theoretically measure less than 65 fmol of labeled marker assuming "only one" samarium atom per marker molecule.

Moreover, given recent improvements in detector technology and computer electronics, such as Compton-suppression equipment, this sensitivity estimate can be improved by a log. It is important to recognize that increasing the neutron flux and/or increasing the duration of the neutron exposure will also improve the sensitivity of this assay. In addition, using an enriched isotope as the tracer will also increase sensitivity. For example, recalculating the specific activity for "enriched" samarium increases the estimated specific activity to $1.1 \times 10^{14}$ disintegrations $s^{-1}$ $kg^{-1}$ which translates to 16 fmol of labeled marker (f is 1 rather than f is 0.26). Similar results are obtained for lanthanum having an estimated specific activity of $3.9 \times 10^{12}$ disintegrations $s^{-1}$ $kg^{-1}$. Equation 1 also demonstrates that this assay only activates a minute population of the stable element present. Therefore, the assay can be repeated to enhance sensitivity and/or to retrieve results from expensive experiments that might otherwise be lost with competing technologies that requires sample destruction to perform the assay.

The activation process will also activate other isotopes present in the sample, adding background noise to the signal, thereby potentially decreasing the sensitivity of the assay. Given their relative high concentration in biological samples, sodium and chloride pose the greatest concern. However, given their short activated half-lives ($t_{1/2}$ of $^{24}Na$ is 15 h, $t_{1/2}$ of $^{38}Cl$ is 37 min) compared to the proposed label of interest, this background activity becomes low following a 2 day decay period. A period of time to allow a short-lived background isotope to become low is referred to as a period of differential decay. Moreover, following a five week decay period, most biological samples (plus our proposed isotopic-labeled probes) will be covered under the NRC regulations for exempt concentrations (10 CFR 32.11), and therefore can be returned to the researcher including non-NRC licensed laboratories. Because components of embodiments of the assays herein are not chemically or physically destructive, researchers can perform additional analyses on the sample. However, certain highly sensitive radioassay methods, such as autoradiography techniques, may require a longer decay period to allow minute amounts of ultra-trace activity still remaining in the sample to fully decay. It is also important to note that desalting methods can be adapted to methods herein to help remove NaCl and other contaminants from samples.

Multiple Counting of Isotopes.

Figure 2:
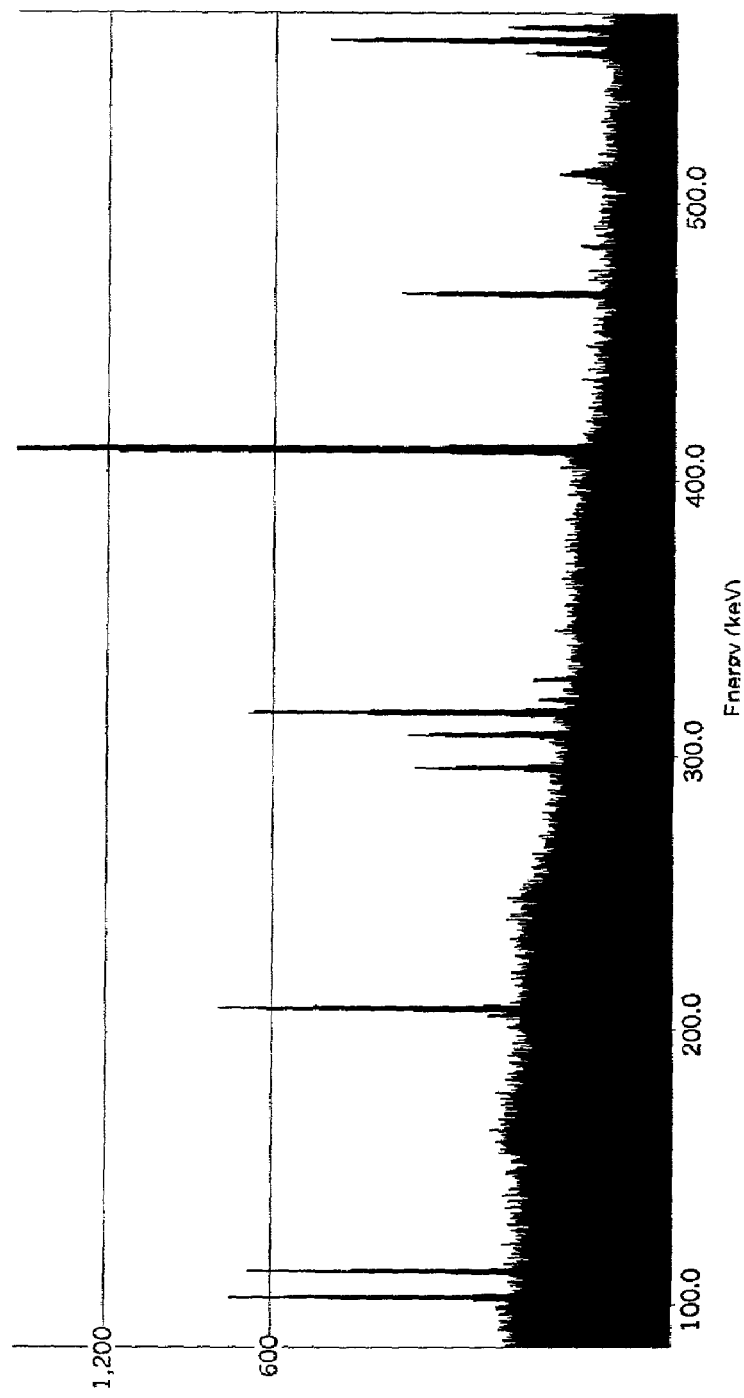
FIG. 2 is a spectrum of a sample containing 8 isotopes measured simultaneously using a photonic gamma counter. The x-axis units are expressed in kilo electron volts representing the energy of the photons. The y-axis shows the frequency in dpm of photon emissions. The identification of each peak is given in the table below.

One of the advantages of stable isotope labeling combined with neutron activation is the ability to measure multiple isotopes simultaneously in a single sample. In FIG. 2, we show the spectrum of a sample containing nine isotopes measured simultaneously using a high resolution germanium based gamma ray counting system. This capability permits conducting multiple experiments in a single animal, or doing multiple medical diagnostics simultaneously in a patient.

Addition of a Monitor Isotope to Sample Vials to Correct for Neutron Flux.

If a standard containing a known mass, $m_0$, of the element-of-interest is exposed to the same flux of neutrons, then determination of the unknown mass, m, within the sample is given by $$m = (m_0 R/R_0),$$

where R and $R_0$ are the count rates of the resultant radioactive nucleus from the sample and standard, respectively. However, it is difficult to achieve a uniform neutron flux rate. Therefore, in order to provide an internal standard, a monitor is used to gauge and correct for neutron flux non-uniformity. A monitor is an element which is useful because this element is not expected to be found within the actual sample. A known concentration of this monitor is placed into both the standard and samples prior to neutron irradiation. The flux rate can be "monitored" by measuring and then correcting differences to the generated specific activity of the monitor. As a result, the accuracy and precision of measuring the unknown mass is further enhanced, as follows:

$$m = R(m_0/R_0)(R_{0,m}/m_{0,m})(m_m/R_m),$$

where $R_m$ and $R_{0,m}$ are the count rates of the monitor in the sample and standard, respectively, and $m_m$ and $m_{0,m}$ are their respective masses.

A monitor is commonly added to samples to account for the non-uniformity of the neutron flux during neutron activation analysis.(6) For example, Neer et al. (7) describe the addition of monitor to samples of interest, however, after the addition of the samples (post-addition of monitor). Further, no efforts were made to control the geometric position of the monitor within the sample tube, i.e. at the bottom, along the side or near the top of the tube.

In commercial uses of neutron activation, tubes containing samples for analysis are received from clients. If tubes are filled to capacity, addition of monitor can be hindered. In other events, there is sufficient room to add monitor, but the monitor remains only at the top of the tube, while with other tubes the monitor may be able to settle to the bottom. Thus the tubes are corrected for neutron flux using different geometries in the counting of the monitor. Variations of several centimeters between the monitor location and the detector face may occur due to these geometrical anomalies, resulting in substantial differences in the attending correction factor. Further, the samples must be opened to add monitor. In the commercial setting, the provider is often "blind" to the customer's research. As a result, the provider risks potential exposure to pathogens within the samples.

The pre-addition of monitor to the sample tube prior to shipping of the tube to the customer eliminates all of these disadvantages. First, the position of the monitor within the tube is standardized eliminating geometrical variation. Second, sample vials can remain sealed, eliminating potential exposure to infectious diseases and toxicants.

Pre-addition of monitor can be accomplished by various means. Since monitor isotopes come in a variety of chemical forms, e.g. water and oil soluble monitor can be added to sample containers in a variety of binders. Monitor can be added to sample tubes as a solution dissolved in binders such as oil or water soluble polyurethanes, waxes, gums, glues and plastics. A variety of techniques can be used to assure that the monitor is maintained in the container, i.e., is not lost as a result of further physical manipulations. The physical location of the monitor is designed to maintain the monitor, for example, inside the main body of the container, on the outer surface of the main body of the container, or in the cap of the container. Further, the monitor can be maintained in the container because it has been formulated as a component of the plastic used to mold the container, and further is evenly distributed throughout the container.

Chemical Bar Coding of Sample Vials.

The pre-addition of monitor offers the opportunity to add other stable isotopes along with the monitor, thereby offering the opportunity to label the tubes chemically, i.e. to chemically bar code sample tubes. Tubes labeled in this manner allow for the identification of tube lot when samples are returned. Thus sample tube tracking is provided, and assures that the customer is using tubes supplied with a kit of reagents, This control allows for better reagent performance, and allows the manufactured to distinguish between its own tubes and other tubes of similar appearance, thereby allowing improved control of inventory and billing. Methods of controlling chemical bar coding include adjusting ratios of the monitor with a second, a third and a fourth suitable isotope, etc., of a stable element.

Chelates for Complexation of Lanthamides.

Stable isotope labeling includes the attachment of chelates to various molecular probes. Probes for measuring hepatic function are chosen for their ability to cross the hepatocyte membrane, and eventually be excreted via the bile. Research has focused on the use of hydrophobic ligands, for example, development of liver magnetic resonance imaging (MRI) contrast agents has concentrated on high-spin iron(III) complexes of N,N'-ethylenebis (2-hydrophenylglycine) (EHPG) .(8) Unlike other chelates, EHPG is hydrophobic due to two phenolic substituents that function as metal binding groups. Recently, Betebenner et al. (9) examined an alternate approach of using a hydrophilic chelate, EDTA, which on its own would not normally cross the hepatocyte membrane. They demonstrated that $^{111}$In-EDTA can be successfully complexed to cholic acid. Moreover, in viva mouse and rabbit models, the cholic acid-EDTA conjugate and $^{111}$In rapidly cleared from circulation and entered into the liver when injected i.v., and was subsequently excreted from the liver into the gastrointestinal tract.

An extensive study of hydrophilic $^{153}$Sm-chelate complexes was carried out by Goeckeler and others, to develop a therapeutic agent for treatment of pain associated with metastatic bone cancer.(10) From a series of 15 chelates, the study identified a $^{153}$Sm-chelate complex, EDTMP (ethylenediamine-tetramethylenephosphonate; Quadramet, Cytogen, Princeton, N.J.) which gave high bone uptake and rapid blood clearance.

Application of Stable Isotope Labeling and Neutron Activation Analysis to the Measurement of Biological Activities and Xenobiotics.

Classification of Stable Isotope Labeled Compounds by Molecular Weight.

Three classes of stable isotope labeled compounds (for example, xenobiotics) exemplify this technique for the measurement of biological functions: (i) low molecular weight compounds, e.g., organic compounds (<5000 kDa), represented by rare earth chelates and chelates of bile acids; (ii) high molecular weight compounds (>5000 kDa), represented by chelates of polymers, such as polysaccharides, polypeptides including proteins, and polynucleotides including nucleic acids; and (iii) colloids.

Proteins used herein can be pegylated, i.e., chemically modified by addition of polyethylene glycol (PEG) molecules, to improve characteristics of the protein such as stability in vivo. PEG additiona produces proteins that retain non-toxic characteristics, and confer amphophilic properties, i.e., solubility both in water and most organic solvents. Pegylation is achieved via stable covalent bonds between an amino or sulfhydryl group of the protein, and a chemically reactive group on the PEG. The reaction can be controlled by procedures known to one of ordinary skill in the art of protein chemistry, and yields prtoeins having a chosen extent of pegylation.

Examples of these polymer compounds and their use are presented for measuring renal and hepatic function. The compounds of these examples are presented for purposes of illustration and teaching, and should not be construed to represent the limits of application of such compounds or other compounds of similar nature and molecular weight. Examples of the application of this technology for the measurement of other biological functions are listed in Table 2.

Classification of Stable Isotope Labeled Compounds by Method of Labeling.

Compounds of interest may be labeled with stable isotope in two ways: (i) They may carry the stable isotope as an intrinsic atom of the molecule of interest. Examples of this method of labeling include drugs carrying a covalently linked bromine atom as part of their structure, and iron oxides such as Feridex IV. (ii) They may be labeled "externally" subsequent to synthesis. Examples of this second method include labeling DNA, RNA and analogs (including antisense drugs) with chelates binding appropriate isotopes of lanthamides (Sm, Lu, La).

Methods of Administration of Stable Isotope Labeled Compounds.

The stable isotope labeled compound may be administered orally, parenterally (for example, intravenously, intraperitoneally, intramuscularly, or subcutaneously), rectally, or by any other suitable method of introducing such a compound into a living subject, including inhalation (for example, inhalation of aerosolized samarium containing compounds, such as by use of a jet nebulizer).

Definition of Xenobiotic.

A xenobiotic is a chemical compound or colloid not found within the body of a test subject under normal physiological conditions, or found at such low levels that the compound is not detectable by ordinary methods. As used herein, the term xenobiotic connotes a compound that is labeled with an atom of a stable isotope capable of capturing a neutron, the atom thereby becoming unstable and emitting a photon.

Definition of Physiologiclly Compatible Solutions.

Stable isotope labeled compounds in general are administered as physiologically compatible solutions. A physiologically compatible solution has a pH between about pH 5 to about pH 9, for example, between about pH 6 to about pH 8. Further, the solution, when administered in volumes of about 2 ml/kg of the subject's body weight, should have an osmolarity in the range of about 230 to about 320 milliosmolar/kg. This adjustment can be accomplished using compounds such as sodium chloride, mannitol, or dextrose. Finally physiologically compatible solutions are sterile. Sterility can be accomplished using a method such as autoclaving, filtration using a filter having a pore size of about 0.1 micron, or exposure to ionizing radiation, such as gamma irradiation.

Definition of Bodily Fluids.

Bodily fluids include liquids obtained from the body of an animal or human subject including blood, plasma, serum, saliva, ascites, cyst fluid, tears, cerebrospinal fluid, digestive juices, bile, urine, semen, vaginal secretions, milk, and feces.

Determination of the Concentration of a Pharmacologically Active Compound Used for the Treatment or Prophylaxis of a Disease Condition.

An embodiment of the method of the invention is the determination of the concentration of a pharmacologically active compound used for the treatment or prophylaxis of a disease condition in a living subject, and especially to determine the proper dosing regimen thereof. Although dosing ranges for a species generally may be known or determined for such compounds, variation within a species may exist, due, for example, to the sex, age and state of health of the particular subjects. Thus, in a noninvasive method for determining the clearance rate based on excretion and/or metabolism over time for a particular subject, it is advantageous to avoid over- or under-dosing. In this embodiment, the stable isotope labeled compound may be any pharmacologically active compound which is labeled with a stable isotope suitable for neutron activation and detection, such as the appropriate isotopes chosen from pharmaceuticals containing elements Sm, La, Gd, Ir, Yb, Au, Fe, As, Sb, Pt, I, and Br. Among those pharmaceuticals currently available possessing these elements are Feridex (Fe), cis-platinum (Pt), Magnavist (Gd), iohexol, and sodium aurothiomalate (trade name Myocrisin) (Au).

In this embodiment, a neutron activatible-detectible, pharmacologically active xenobiotic compound (i.e., a compound not found endogenously in a normal subject), may be administered to a subject, and the concentration of that compound followed over time by the present method. The amount and timing of the dosage to be administered to a particular subject may then be adjusted, as appropriate, to maintain desired levels in the subject of the compound over the course of the treatment.

Determination of the Concentration of a Pharmacologically Inactive Compound Used for the Diagnosis of a Disease Condition.

Another embodiment of the invention is determination of the clearance rate. The clearance rate comprises whether or not clearance occurs, for example, as measured by a decrease in relative or absolute terms of the compound as a function of time of excretion a xenobiotic compound from a living subject. The clearance rate provides information as to the functional status of the excretory organs of that subject, such as the kidneys, liver and lungs.

In one embodiment, for example, the absence of removal of the administered compound from the body, or removal at a rate below that found in healthy subjects, assists in diagnosing dysfunction of the excretory organ, or in monitoring the progress of disease in that organ. Stable isotope labeled compounds which may be employed in this embodiment are those compounds that are cleared by the organ of interest, are not substantially metabolized by the subject, and are not cleared concurrently by organs other than the organ or organs of interest.

In another embodiment of methods of the invention, the glomerular filtration function of a living subject is measured, for example, by determining the half-life time for glomerular filtration of a stable isotope labeled compound, cleared through the kidneys, allowing evaluation of the health of these organs. An optimum stable isotope labeled compound to be employed in this embodiment is one which is substantially, or even completely removed from the subject through the kidneys, and which is neither secreted nor reabsorbed by the renal tubules. Paramagnetic contrast agents and analogs labeled with stable isotopes are particularly useful for this purpose, for example those which are chelates of samarium. Examples of the latter are $^{152}$Sm-diethylenetriaminepentaacetic acid ($^{152}$Sm-DTPA, for example, $^{152}$Sm-DTPA disodium or dimeglumine salts), $^{152}$Sm-diethylenetriaminetriacetic acid bismethylamide ($^{152}$Sm-DTPA-BMA), and $^{152}$Sm-tetraazacyclododecane tetraacetic acid ($^{152}$Sm-DOTA), for example, gadoteridol, Sm-hydroxypropyl tetraazacylo dodecanetriacetic acid ($^{152}$SmHP-DO3A). Similar compounds labeled with Gd have been described, see, for example, in U.S. Pat. No. 4,885,363. The stable isotope labeled compound may be administered to the subject by any suitable route, for example, a route that is intravenous, subcutaneous, intraperitoneal, intramuscular, or oral. Amounts employed should be suitable for detection, and may, for example, be about 5 µmol to about 1 mmol, or about 50 µmol to about 0.3 mmol, of agent per kg of body weight of the subject.

Renal Applications

Application of Stable-Isotope Labeling and Neutron Activation to the Measurement of Glomerular Filtration Rate.

An application of stable-isotope labeling followed by neutron activation is measuring kidney function through the determination of the glomerular filtration rate. Kidney and urinary tract disease affects more than 20 million Americans, with an additional 3.3 million having unrecognized and undiagnosed kidney diseases. Over 250,000 Americans are currently being treated for end stage renal disease primarily resulting from diabetes, hypertension and glomerulonephritis. Diagnosis and monitoring of renal disease is partially based on either a 24 hour creatinine clearance or on a serum creatinine test. Creatinine clearance test results have been shown to overestimate actual renal function by up to 92% in patients with very severe renal disease. Numerous studies have shown that overestimation of renal function by creatinine-based tests increases as renal function diminishes.

A determination of the glomerular filtration rate (GFR) of a subject and or patient is frequently requested by researchers and/or physicians to assess renal function. Accurate GFR determinations are important in the determination of appropriate dosing of medication, as well as for monitoring of drug induced nephrotoxicity in a patient.

The most frequently measured parameters indicative of renal function are serum creatinine and urea levels. However, much renal damage must have occured before these values become abnormal, so that early detection is not possible using these measurements. Although the creatinine clearance test is simple and does not require specialized equipment, it is subject to important and well recognized errors, some of which are described below.

The accuracy of glomerular filtration rate (GFR) measurements depends on a "filtration" marker. An ideal filtration marker would be one that is exclusively filtered by the kidney but is neither secreted nor reabsorbed by the renal tubules. Creatinine does not comply with all these requisites.

While being filtered by the patient's kidneys, it is also secreted by it. Thus, glomerular filtration rates obtained by this method are inaccurate.

Urine samples for the creatinine clearance test are typically collected from a subject over a 24 hour period. This long period of time is burdensome to the patient and to the nursing staff, and presents repeated opportunities for error. For example, the patient may forget to save one or more samples, samples may be spilled, and specimens or collection time points may be inaccurately recorded by the staff. These limitations of the creatinine clearance method have led nephrologists to rely on other techniques.

An early alternative was utilization of inulin for measuring glomerular filtration rates (GFR). Inulin is a natural polysaccharide that is exclusively filtered by the kidney. A world-wide shortage of inulin, however, combined with the cumbersome analysis techniques required by the test, have prompted the use of other methods.

An alternative test utilizing Technetium-99m-DTPA ($^{99m}$Tc-DTPA) as a filtration marker was introduced. Instead of relying on assay of the presence of chemical as with the creatinine and inulin tests, the $^{99m}$Tc-DTPA test relies on measurement of radioactivity levels in a sample. While the $^{99m}$Tc-DTPA test has proven to be accurate, there are various disadvantages to its implementation. The $^{99m}$Tc-DTPA test must be performed in an approved nuclear medicine facility by a registered nuclear technologist. In addition, the material administered to the patient is radioactive, and the patient is therefore exposed to a small dose of radioactivity. These drawbacks have led to a consideration of other techniques.

Another radioactive isotope based chelate (lanthanum-140-DTPA) has also been considered for GFR measurements.(38,39) A study using $^{140}$La-DTPA for the measurement of GFR in the dog was successful, however due to the high radiation dose associated with the decay of $^{140}$La, its use is not considered suitable for human application. (38)

Gadolinium-DTPA (Gd-DTPA) is a paramagnetic substance (Magnevist, Berlex Laboratories, Cedar Knolls, N.J.) that was approved in the United States as a magnetic resonance imaging contrast agent in 1988. Since then it has been used as an enhancer of magnetic resonance images in tomography studies (U.S. Pat. No. 4,647,447, the entire content of which is incorporated herein by reference). Gd-DTPA has proven to be an extremely safe and well tolerated agent, and has been approved for use in children.

Paramagnetic substances such as Gd-DTPA have been proposed for the measurement of glomerular filtration rates by NMR technology (U.S. Pat. No. 5,100,646, the entire content of which is incorporated herein by reference). This method has failed to find substantial use, due to the need for expensive and not readily available equipment for performing NMR measurements. A second problem with this method is its reliance on elaborate standard curves that are dependent upon the body fluid used. Third, this method is dependent upon blood processing to obtain serum. Finally, this method is limited to the measurement of a single NMR modulator at a time. Thus measurement of multiple paramagnetic probes can not be obtained simultaneously, and even further, requires the complete elimination of the first probe from the subject before the second probe can be added. A more specific limitation of the technique is testing in a situation where a probe has been administered incorrectly. In this case, a new measurement can not be executed until complete elimination of the paramagnetic probe has occurred, about 24 hours later, and can thus requires a second office or clinic visit on a subsequent day by the subject.

A commercial radioactive technology recently approved for measurements of GFR (glomerular filtration rate) in a human subject uses sodium iothalamate $^{125}$I as marker. This compound is radioactive and has all the disadvantages of radioactive materials listed above. In addition, the half life of $^{125}$I is short and requires monthly shipments of sodium iothalamate $^{121}$I to resupply hospital pharmacies. Unused material is discarded, causing inefficiencies and increased expense. Finally, the problems incurred for multiple measurements described above with paramagnetic probes are also found with radioactive probes.

Using an exogenous renal clearance marker is the most accurate method available for assessing kidney function and offers an attractive alternative or supplement to creatinine assays. Compounds such as samarium DTPA are ideal for use as GFR probes. This class of non-radioactive compounds is stable and can be detected at very low concentrations (10 to 100 times lower than paramagnetic probes) providing increased measures of safety. The measurement is made on whole blood. The potential availability of multiply labeled chelates having identical biological properties allows the repeat measurement or simultaneous measurement of GFR and other excretionary systems. Neutron activation is supplied as a service, eliminating the need for expensive sophisticated equipment within the clinic, thereby opening GFR assays to the general physician in tertiary and rural settings. Finally, the use of stable isotope labeled compounds and neutron activation has not previously been applied to the measurement of GFR.

Specific Measurement of Glomerular Filtration Rate.

Measuring glomerular filtration rate is a specific example of the general method for measuring blood clearance of xenobiotics labeled with a stable isotope. Glomerular filtration rates can be measured by the single injection technique (11) or by the continuous infusion technique.(12) Advantages of the method include that samarium-DTPA (Gd-DTPA) is filtered exclusively by the kidney, and is neither secreted nor reabsorbed by the patient's kidneys. Further, samarium ($^{149}$Sm), is not a radioactive element and therefore does not expose a patient to radioactivity. It is thus an ideal "filtration marker". Moreover, the stable isotope of samarium, $^{152}$Sm, is excellently suited for neutron activation due to its neutron cross section, the simplicity of the emission spectrum of its activated daughter nuclide and the resulting half life of the daughter nuclide.

The present methods in certain embodiments thus use direct measurement of the concentration of a stable isotope, instead of measurement of radioactivity as is the case with the $^{99}$Tc-DTPA test, and with indirect measurements of concentration such as relaxivity used with Gd-DTPA for GFR measurements that rely on the NMR properties of matter.

The methods of various embodiments of the invention may suitably be applied to the field of clinical medicine, veterinary medicine and for research applications. Advantages of various embodiments of the methods include:

[1] Administering to a patient a non-radioactive, safe, stable isotope labeled compound, such as Sm-DTPA.

[2] Performing the method in an outpatient hospital facility, a doctor's office, or the patient's home.

[3] Not requiring any special handling or treatment of specimens.

[4] Not requiring equipment for the clinic, hospital, or doctor's office, as samples are shipped out for analysis. The savings on equipment, laboratory space, maintainance and staff training can reduce hospital expenditures.

[5] Not requiring labor intensive procedures, but rather performance by a nurse or other health worker with minimal training.

[6] Availability of results of the test within two days.
[7] Performing the method in less time, more accurately, and less inconveniently than the creatinine clearance test (routine but inaccurate method to estimate GFR) or the inulin assay of GFR.
[8] Providing a simple kit that is not radioactive, and is therefore both stable and safe to handle.

Thus the present technology is suitable for widespread adoption with gains in accuracy and with lower expenditures.

In a specific example, this invention provides a method of determining the glomerular filtration rate (GFR) of a subject, with the following details: obtaining a serum sample $S_{pre}$ and a urine sample $U_{pre}$ from a subject; administering to the subject an amount of a stable isotope labeled substance that is filtered by the kidneys and that is readily detectable by neutron activation in serum and urine; allowing for the concentration of the substance to equilibrate between the blood and the extravascular spaces; allowing the subject to void and discard urine at a time $t_A$, wherein A is 0; obtaining a serum sample $S_A$ at a time $t_A$ wherein A is as described above; making A=A+1, i.e., at the next time point; allowing the subject to void at a time $t_A$ and measuring the volume of urine $v_A$, wherein $v_A$ corresponds to a time interval ($a_A = t_A - t_{A-1}$); separating an aliquot of the urine sample $v_A$ and obtaining a serum sample from the subject at the time $t_A$; calculating a urine rate $(v/a)_A$ from the formula $(v/a)_A = v_A/a_A$; repeating steps [6] through [9] until the difference among at least three of the urine rates (v/a) is less than about 2 cc/min, and determining concentration of the stable isotope label (usually samarium) by neutron activation of the serum and urine samples corresponding to the three end time points $t_A$ for the urine rates, wherein i is 0 to p, and p is at least three; obtaining the concentrations of the stable isotope labeled substance $[SI]_{S_i}$ in the $S_i$ serum samples and the $[SI]_{U_i}$ in the $U_i$ urine samples, wherein i is as defined above; and calculating GFR from the formula $$GFR = \sum_{i=1}^{p} 2 \times [SI]_{U_{i+1}} \times v_{i+1} / ([SI]_{S_i} + [SI]_{S_{i+1}})/p$$

wherein p is as described above.

Other methods of determining glomerular filtration rates have been reported using for instance Glofil 125 (sodium iodothalamate-$^{125}$I, www.glofil.com), and these methods may also be applied for this application.

Example of Glomerular Filtration Rate Determination Using the Single Injection Technique with a Stable Isotope Labeled Chelate.

The single injection technique for determining the glomerular filtration rate (GFR) of a subject is performed with the following details: administering to a subject a specific volume of an oral water load, e.g., about 20 ml/kg one hour before administration of the test substance; obtaining a serum sample $S_{pre}$ and a urine sample $U_{pre}$ from the subject; administering i.v. to the subject a diagnostically effective amount of a test substance, the test substance being a compound, X-M, wherein X is a chelator and M is an atom of a stable isotope of an element, the atom being noncovalently bound to the chelator and having a nucleus capable of capturing a neutron, thereby becoming a radioactive isotope of the element that is filtered by the kidneys and is readily detectable by neutron activation analysis in serum and urine, and waiting for a specific time interval, which is about 30 to about 60 minutes; collecting a urine sample and a blood sample, labeled, "Urine discard and Blood #1"; waiting for a specific time interval, which is about 30 to about 60 minutes, and collecting a urine and blood sample, labeled, "Urine #1 and Blood #2"; waiting for a specific time interval, which is about 30 to about 60 minutes, and collecting a urine and blood sample, labeled, "Urine #2 and Blood #3"; and determining the concentration of test substance in blood and urine using neutron activation analysis, and calculating the clearance rates by using the formula C=(UV/P)×(1.73/SA) where C is glomerular filtration rate in ml/min/1.73 m$^2$, U is urine concentration of test substance expressed in disintegrations/min/ml, V is urine flow rate in ml/min, P is mean blood or plasma concentration of test substance expressed in disintegrations/min/ml, and SA is body surface area in m$^2$.

Example of Glomerular Filtration Rate Determination Using the Continuous Infusion Technique with a Stable Isotope Labeled Chelate.

The continuous infusion technique for determining the glomerular filtration rate (GFR) of a subject is performed with in the following details: administering an oral water load of about 1500 ml two hours before administration of the test substance; inserting into the bladder a number 14 or 16, for example, French Foley catheter; infusing lactated Ringer's solution i.v.; dividing the dose of test substance equally between a priming dose and a sustaining dose diluted in about 30 to about 60 ml of isotonic sodium chloride, the test substance being a compound, X-M, wherein X is a chelator and M is an atom of a stable isotope of an element, the atom being noncovalently bound to the chelator and having a nucleus capable of capturing a neutron, thereby becoming a radioactive isotope of the element that is filtered by the kidneys and is readily detectable by neutron activation analysis in serum and urine; injecting the priming dose followed by the sustaining dose at a rate of for example, 0.5 ml/min and waiting about 40–45 minutes; collecting for example, 5 ml of blood every 15 minutes three to five times; collecting total urine content associated with each blood collection and noting the urine volume; and determining the concentration of test substance in blood and urine using neutron activation analysis and calculating the clearance rates by using the formula C is (UV/P), where C is glomerular filtration rate in ml/min/1.73 m$^2$, U is urine concentration of test substance expressed in disintegrations/min/ml, V is urine flow rate in ml/min, and P is mean blood or plasma concentration of test substance expressed in disintegrations/min/ml.

The unilateral glomerular filtration rate (GFR) of a subject may be determined by the use of ureteral catheterization.

The three methods presented for determining glomerular filtration rates indicate the importance of hydration of subjects during the process or immediately proceeding initiation of the process. Hydration may be accomplished by oral or intravenous administration of water or an aqueous solution.

Blood and urine samples are obtained from each subject/patient. The samples may be stored until the entire procedure is completed, so that the determinations are all made at one time. Alternatively, each sample may be subjected to neutron activation immediately after being drawn. The samples are stored cold or frozen, for example, at a temperature of about –70° to about 10° C., for example, at about –30° to about 5° C., in closed containers.

Suitable stable-isotope labeled substances are pharmaceutically acceptable compounds or substances that are filtered by the kidneys, for example, filtered exclusively by the kidneys, and may be compounds or substances that are neither secreted nor reabsorbed by the kidneys. Examples are samarium (and other lanthamide series) analogs of Gd-DO$_3$A (Bristol-Myers Squibb, New York, N.Y.), Gd-DTPA-BMA (Nycomed, Amersham, Bucks., UK) and Dysoprosium-DTPA (Nycomed, Amersham). Other examples include the samarium analog of Gd-diethylenetriaminepentaacetic acid (Gd-DTPA, Berlex, Wayne, N.J.), and the samarium analog of Gd-(1,4,7,10-tetraazacyclododecane-1,4,7,10-tetraacetic acid) (Gd-DOTA, Guerbet, Paris, FR). Other elements that are analogs of Gd and contain isotopes suitable for neutron activation can be substituted for Gd in the above listed chelates, including but not limited to La, Eu, Ir, Yb, and Dy.

The stable-isotope labeled substance is administered to the subject by routes known in the art, for example, any of the routes described herein, for example, i.v. A paramagnetic substance, e.g., Sm-DTPA can be administered for example, in an amount of about 0.1 µmol to about 10 µmol per kg body weight. In an embodiment of the invention, the stable-isotope labeled substance is administered in an amount of about 2 to about 80 µmol per kg body weight. However, amounts of Sm-DTPA or other stable-isotope labeled substances outside of the stated range may also be administered as long as they are detectable by neutron activation in the blood and urine samples obtained from the subject. In some cases, the stable-isotope labeled substance is administered to a subject subsequent to obtaining the first blood and urine samples, and which may, in a related embodiment, be used as controls and for the preparation of standards.

After a period of time of about 10 to about 120 minutes after administration of the stable-isotope labeled substance, for example, a period of about 60 to about 120 minutes, the patient voids and a first blood sample is obtained, for example, when the subject is capable of voiding. Alternatively, the subject is catheterized, and urine samples may be obtained about every 10 to about every 60 minutes, for example about every 20 to about every 30 minutes.

In one embodiment, the time interval between subsequently obtained blood and urine samples is, in general, determined by the subject. Suitable time intervals are about 10 to about 60 minutes, for example, about 15 to about 45 minutes. In order to minimize the number of samples that need to be taken, each subject may be requested to void every so many minutes, for example, about every 20 minutes.

Once the volumes and the time interval are obtained for each sample's time point, they may be recorded into a data recording system, for example, on a time sheet, or in a notebook having forms for recordal. Alternatively, the data may be inputted into a data recording system such as a computer, and the computer may then calculate a urine rate, or a volume:time interval ratio $(v/a)_A$ from the formula $(v/a)_A = v_A/a_A$ wherein v, a and A are as defined above.

The patient is then allowed to void again, to obtain another urine sample, and another blood sample is obtained, and appropriate steps described above are repeated, until the difference among at least three of the volume:time ratios is less than about 2 ml/min, for example, less than about 1 ml/min.

The number of time intervals for which the collected urine volume:time interval ratio between sample collections is substantially equivalent is, however, not fixed at 3 or 4. Any number of intervals may be encompassed by the present method. In general, it is observed that having at least three constant volume:time ratio intervals, will suffice to obtain accurate results.

When at least three time intervals are chosen in accordance with the criterion described above, then the concentrations of the stable isotope in the urine and corresponding serum samples are determined. This yields at least nine values, at least five of which correspond to blood samples and at least four correspond to urine samples, wherein i is 1 to p, and p is at least 3, but may also be chosen to be any value greater than 3, such as 4, 6, 10, and even higher values.

The concentrations of the stable isotopes are obtained by weighing each sample, and determining the amount of stable isotope in the sample by neutron activation.

The $[SI]_{Ui}$ and $[Si]_{Si}$ are then utilized along, with the $(v_i^U/a_i)$ volume:time interval ratios or urine rates selected to calculate the glomerular filtration rate (GFR) of the subject in accordance with the mathematical formula of step [12].

In one embodiment of the method, the concentrations of the stable isotope labeled substance in the serum and urine samples are obtained, then the calculation of the GFR in step [12] may be conducted in the data recording system that can be provided, for example, conducted manually, or with a computerized program.

In addition to the steps described above, the method of the invention may further comprise, prior to step 1, hydrating a subject with a hydrating solution. The hydration step is conducted, for example, via a route that is oral, or is intravenous. However, other modes of administration are also suitable such as a combination of oral and parenteral routes of hydration, as is known in the art.

Following the injection of the stable-isotope labeled substance, hydration may be maintained by, e.g., a combination of oral and intravenous fluids, as determined by the subjects ability to drink. The fluids may be administered at about 300 to about 500 ml/hr as determined by the subject's condition. Physiologically acceptable aqueous solutions typically include water for oral hydration or any other non-caffeinated fluid containing water (e.g. juices). Suitable intravenous fluids include dextrose, for example, 5% dextrose in water. As is known in the art, intoxication from administration of pure water or other hypotonic preparations is not recommended as it can result in patients becoming hyponatremic, usually a result of renal insufficiency and intravascular overload.

The amount of fluid administered by either route should approximate 5 ml/hr per kg of body weight, to maintain a diuresis of about 300 to about 400 ml/hr. This rate affects length of the study, since the frequency of timed intervals may be partially determined by the rate of urine production. However, in patients unable to tolerate this amount of fluid, lesser amounts of hydration are possible.

Different fluids are appropriate to hydration administered exclusively via the oral or exclusively via the parenteral route. Oral administration may consist of water, or non-caffeinated water based drinks, such as juices, in an initial amount of about 20 ml/kg body weight, with a maintenance amount of about 5 ml/hr per kg body weight. The exclusively intravenous administration of fluid comprises, in one embodiment, 5% dextrose in water, at a rate of about 300 to about 500 ml/hour, depending on patient tolerance. However, other components can be added to the hydration agent, as is known in the art.

In still another embodiment, the above method is conducted by practicing the hydration step both by the oral and parenteral routes, for example, oral and intravenous routes. Typically, the hydration step may be conducted about 10 to about 120 minutes before step 1, for example, about 30 to about 60 minutes before that step. However, other time schedules are also suitable.

In practicing the above method the amount of stable isotope labeled substance administered the subject should be sufficient for the detection of stable isotope labeled substance in the urine and serum samples prepared as described herein. Typically, the amount of the administered stable isotope labeled substance, e.g., Sm-DTPA is about 10 to about 100 mmole/kg of body weight of the subject, for example, about 20 to about 80 mmole per kg of body weight. However, other amounts of the stable isotope labeled substance may also be administered as found appropriate.

An embodiment of invention is a kit intended for practicing the method of the invention with the hydration step.

The hydration as described above may be conducted via oral or parenteral routes, or both. A physiologically acceptable, i.e., isotonic sterile aqueous solution is intended for the parenteral hydration of the subject.

Also provided herein is a kit for determining the GFR of a subject, using a stable isotope labeled substance and neutron activation analysis, comprising at least one, for example, to about 1000 sample collection vials of uniform weight and sealed sufficiently tightly to hold steam; at least one, for example, to about 1000 data collection sheets; and a physiologically-acceptable sterile aqueous solution of the stable-isotope labeled compound, comprising a concentration of about 0.001 to about 1.0M of the compound; for an example, an embodiment of the kit comprises about 10 to about 500 sample collection vials and about 10 to about 500 data collection sheets.

In yet another embodiment, the sterile stable isotope labeled solution, e.g., the sterile Sm-DTPA solution, comprises from about one μmole to about 1.0 mole of the substance, for example, about one-half M Sm-DTPA. Doses of about one μmol to about 0.2 mmol/kg weight of the patient are suitably administered. Lower concentrations are in general used, as long as they provide an amount sufficient to be detectable in the urine and serum samples by neutron activation. The accuracy of the results is not affected by the amount of the substance administered to the subject, as shown in the examples.

Generally, a kit may further contain at least one and, for example, may contain about 1,000 intravenous administration sets, for example, about 50, or about 500 sets. These sets are sterile, and are provided in separate enclosed packages, or as preloaded syringes. Each set is utilized for one patient and then discarded. The intravenous administration set may comprise a needle, a length of flexible tubing and a container or reservoir from which the hydration solution and/or stable isotope labeled compound, e g., the Sm-DTPA solution, are administered.

In an embodiment of the invention the kit further comprises a physiologically acceptable sterile aqueous solution comprising about 5% dextrose by weight.

The intravenous administration sets described above may also be utilized. These administration sets may be utilized for the separate administration of the Sm-DTPA solution and the hydration of the patient to a subject. Both administration lines may be left in place until the entire procedure is completed.

Method 2.

An alternative method for measuring GFR is presented. This method involves obtaining an initial measurement of a pre-administration sample having concentration $C_{PRE}$ from a subject, followed by the administration of an stable isotope labeled neutron activatable-detectable compound. Subsequent measurements of $C_t$ are then obtained over time, such as about every 5 to about every 90 minutes following administration. The subject may void the compound via the kidneys during the study time.

The logarithms of the differences in the concentrations of $C_{PRE}-C_t$ before and after administration of the stable isotope neutron activatable-detectable compound (i.e., $\log(C_{PRE}-C_t)$, where $C_t$ represents a concentration in a sample taken after administration, and $C_{PRE}$ represents a concentration taken prior to administration) may be plotted as a function of time, and the elimination halftime ($T_{1/2}$) calculated from the slope of the log plot according to known methods.(13) The halftime value(s) so obtained allow a diagnosis to be made as to the glomerular filtration functioning of the subject, and hence an evaluation of the health of the kidneys of that subject. Illustrative of this method but using NMR probes for detection for calculating glomerular filtration rates are described in Tweedle.(14)

Thus, the invention provides a method for the non-spectroscopic, non-imaging evaluation of the glomerular filtration functioning of a subject, comprising:

(i) recording a baseline measurement of the concentration in the subject's blood of the stable isotope under consideration;

(ii) administering to the subject an isotope labeled agent, wherein the agent is capable of renal excretion and is detectable following neutron activation;

(iii) sampling blood from said subject at suitable time intervals for determination of stable isotope concentration;

(iv) calculating the halftime $T_{1/2}$ from the values of concentration; and (v) evaluating the glomerular filtration of said subject from the value $T_{1/2}$.

Application of Stable-Isotope Labeling and Neutron Activation to the Measurement of Glomerular Integrity Rate (GIR), also known as Glomerular Size Selectivity (GSS).

Glomerular integrity rate is a general term for measuring renal function which can be determined using rate measurements of change in blood or urine concentration after addition of a test compound to the blood of a subject. Glomerular integrity rate measurements include renal blood flow, glomerular size selectivity, glomerular charge slectivity, and glomerular filtration rate.

The incidence and prevalence of end-stage renal failure in the United States continue to increase.(15) In 1995, the incidence rate was 262 per million population, with a prevalence rate of 975 per million population.(15) The exact number of individuals with abnormal renal function but not yet at end-stage failure is difficult to assess. However, crude estimates place this number at approximately 0.4% of the U.S. population.

The rate of progression is also difficult to assess. In general, subjects displaying renal manifestation of certain systemic diseases, such as diabetes mellitus and systemic lupus erythematosus, and those with significant proteinuria, seem to have a more rapid progressive course to end-stage failure. If intervention is expected to be successful in halting or slowing such progression, accurate assessment of early manifestations of renal disease, and renal structure and function, need to be established.

Current methods that can best measure these parameters involve elaborate and expensive laboratory procedures, extensive hospital stays, radioactive tracers, and/or potentially nephrotoxic contrast media. As a result, the availability of these assays is restricted to licensed and/or experienced facilities, limiting or excluding the ability to effectively monitor patients over the time course of the disease. These same limitations also restrict researchers from measuring physiological parameters in experimental models. Therefore, providers of reliable diagnostics to measure renal structure and function that are cost-effective, easy-to-use and can be repeated in subjects to monitor their response to therapeutic intervention will have a clear advantage in this market.

In September 1996, the National Institute of Diabetes and Digestive and Kidney Diseases of the National Institutes of Health convened a meeting of experts to review the current status of diagnosis and treatment of progressive renal disease, and to make recommendations pertaining to the current status of techniques used to identify and monitor progression of renal disease.(15) The conference members concluded that better methods are needed to identify patients at risk of developing end-stage renal failure and that more efficient techniques are needed to monitor their response to therapeutic intervention.

Currently accepted methods of assessment of renal disease include measurement of renal function such as serum creatinine and glomerular filtration rate, (16–18) measurement of proteinuria, (19) assessment of tubular function, (20) glomerular sieving and permselectivity, (21, 22) radiologic imaging techniques, (23) and evaluation of histomorphometry.(24) Given its low-cost and availability, serum creatinine is the most frequently used test to assess renal function.

Unfortunately, by the time the serum creatinine is "abnormal", the glomerular filtration rate is already substantially diminished.(25) Other tests that can better assess early-stage disease involve elaborate and expensive procedures, diminishing their usefulness as a widespread screening diagnostic and restricting their repeated use for monitoring the progression of the disease.

Glomerular Integrity Rate (Glomerular Size-selectivity).

The glomerular capillary is a unique and highly efficient barrier providing a highly permeable structure for the filtration of water and small molecular substances, while preventing the loss of important macromolecular substances the size of albumin or greater. This barrier is the result of glomerular permselective properties, which are described by two distinct features: [1] size-selectivity, the ability of the glomerular filter to progressively hinder the passage of macromolecules from the blood into Bowman's space, with increasing molecular radius; and [2] charge-selectivity, the ability of the membrane to restrict filtration of negatively charged molecules more effectively when compared to equally sized uncharged or cationic compounds.

To study normal and diseased glomerulus, researchers have estimated the fractional clearance of a nonprotein inert polymer, such as dextran, (23, 26) polyvinylpyrrolidone, (27) and Ficoll (21), relative to some "freely permeable" reference polymer, such as inulin. Of these exogenous probes, uncharged dextran, a polymer of glucopyranose, has been most extensively used to study the normal barrier function as well as to study the abnormal changes that occur in the setting of proteinuria. However, dextran's conformation becomes altered during transglomerular permeation. As a result, its transport is facilitated, leading to an overestimate of the effective radii presented by functional glomerular pores to permeating proteins. In contrast, recent studies have shown that Ficoll, a polymer of sucrose, more closely approximates that of an ideal, uncharged globular protein. (26) Like dextran, its component molecules have a broad distribution of molecular radii, ranging from those small enough to be freely filtered to those that are sufficiently large to be impermeant. Ficoll also is uncharged, permitting exclusive evaluation of the size-selective properties of glomerular capillary walls. As a result, Ficoll has recently become the polymer-of-choice for researchers studying glomerular size-selectivity.

However, current procedures that use non-reabsorbable polymers, such as Ficoll, to measure glomerular size-selectivity are cumbersome in practice. Although optically-labeled polymers are valuable for studying permeability, (28) sensitivity and toxicity issues have limited their usefulness, particularly in human subjects. Therefore, radioactive tags remain the standard reagent. Polymers are either labeled on site, a labor-intensive procedure frequently requiring more than 24 hours to complete, or are purchased pre-labeled from a vendor whose labor costs are reflected in the purchase price. Following infu sion of the labeled polymer, each collected urine and serum sample is fractionated using various chromatographic techniques, to separate the polymer into fractions having narrow size distributions. This separation step employed on each sample is time consuming, requires specialized equipment and skilled laboratory labor, and in the clinical arena, exposes laboratory personnel to agents of infectious diseases. Once the size distribution of the inert polymer is known, one can then characterize the size-selective properties of the glomerular filtration barrier by calculating the fractional clearance (or sieving coefficient, θ) of the polymer. The fractional clearance is defined as the clearance of the labeled polymer divided by the glomerular filtration rate (GFR) of water. The clearance of inulin is frequently used to measure GFR. (21, 22) This separate assay adds complexity and increases the cost of current procedures for measuring glomerular permselectivity. Once all the data is collected, the fractional clearance is calculated from the urine concentration (U) and plasma concentration (P) of the labeled polymer and of inulin as follows:

Fractional clearance=$(U/P)_{polymer}/(U/P)_{inulin}$

Given that the labeled polymer is neither reabsorbed nor secreted, and that the excretion of inulin is also not modified by tubular function but appears in Bowman's space in the same concentration as in the plasma water, the ratio of urinary clearance of the labeled polymer to inulin is equal to the ratio of the concentration of inulin in Bowman's space to its concentration in plasma water. Therefore, the fractional clearance value is a convenient measure of permselectivity, varying from zero, when the labeled polymer is impeded, to unity when it encounters no measurable restriction to filtration. For example in normal human subjects, neutral-labeled molecules with radii less than or equal to that of inulin (~14 Å) appear in Bowman's space in the same concentration as in plasma water (i.e, fractional clearance equals 1).(24) As labeled molecular radius increases, filtration decreases progressively, reaching low values as the size of serum albumin (~36 Å) is approached.(24) Therefore, this measurement can diagnose abnormal renal function and may also offer the ability to stage the disease and then gauge the effect of therapeutic intervention.

This general method for determining glomerular selectivity has been used to study changes in renal function due to dietary influences, (29) disease, (21, 22) organ transplantation, (19) and therapeutic interventions. Despite the technical difficulties, it is clear that this technique provides unique insights into the mechanisms of proteinuria in experimental models and in humans and can play an important role in evaluating the effectiveness of dietary and pharmacological therapies. A review by the National Institute of Diabetes and Digestive and Kidney Diseases of the National Institutes of Health states that issues related to cost, technical analysis and modeling of data derived from glomerular selectivity studies using current methodology preclude its wide-spread use, and that research should be directed to overcoming these barriers.(15)

In embodiments of the invention, pre-sized polymers of distinct molecular weight and narrow non overlapping size distribution are each labeled with a different stable isotope. When a set of these molecular markers are administered simultaneously, their passage across the glomerulus can be determined in a single measurement and in the absence of any separation steps.

The adaptation of stable isotope labeling and neutron activation to the measurement of glomerular size selectivity thus offers an innovative method to assess this renal parameter. Advantages include, first, that this approach is non-radioactive, and eliminates the cumbersome step of post-separating macromolecule fragments found in each of the urine and serum samples. The stable-isotope method is less labor intensive and less expensive than conventional methods. Second, with simplified sample handling (no chromatography), a safer environment is provided for the technologist. Third, multiple molecular markers of different sizes can each be labeled with a different stable isotope probe, providing, a method to quantitate the extent of glomerular deterioration in a single measurement. Fourth, stable-isotope probes can also be used to known labeled reference polymers of proved utility, such as inulin or others, (17) and chelates such as DTPA and DOTA (described above under GFR). Fifth the combined administration of multiple molecular markers together with a GFR marker to the subject will simultaneously obtain a GFR measurement and glomerular size-selectivity data. Unique diagnostic information is obtained while consolidating sample collection and data analysis. Altogether, stable-isotope labeling and neutron activation applied to glomerular size selectivity determinations provide an improved way of handling and processing samples that is less labor intensive, less expensive, and provides more information in a shorter time, compared to current methodology which relies on the separate determination of these two parameters.

In addition to providing unique clinical opportunities, a nonradioactive and nontoxic method of measuring glomerular selectivity in research subjects and in humans will accelerate the development of effective research products that will allow clinical investigators to better understand the normal and pathophysiologic basis of macromolecular permeation across the glomerular filtration barrier.

Hepatic Applications

Application of Stable-Isotope Labeling and Neutron Activation to the Measurement of Bile Acids.

In the United States, 62 million people are diagnosed with digestive disorders each year, resulting in nearly 200 million sick days, 10 million visits to physicians, 10 million hospitalizations, and nearly 200,000 deaths per year. Given the insidious onset of hepatic disease, many patients are misdiagnosed, or go undetected until they are clinically advanced. Furthermore, most digestive diseases are complex, having subtle symptoms that further confound detection and diagnosis. Because of this, patients can expect to undergo extensive and expensive diagnostic tests before a correct diagnosis is reached and an effective therapy can begin. For example in 1992, direct healthcare expenditures approached $107 billion for diagnosing and treating digestive diseases. Therefore, the development of more reliable diagnostics to measure specific functional parameters of digestion that are easy-to-use and can be safely repeated in patients to monitor their response to therapeutic intervention can reduce both human suffering and overall healthcare costs. Applications of these improved methods to screening diagnostics that can accurately detect patients in the early stages of "specific" hepatic diseases can improve prognosis, reduce suffering, and serve as a means to identify patients at high risk. In addition, improved methods to measure functional parameters will aid research directed toward the development of more effective therapies.

Bile Acids, Hepatic Circulation, and Clinical Application.

The bile acid pool consists of primary, secondary and tertiary bile acids. Primary bile acids, cholic and chenodeoxycholic acids, are formed in the liver from cholesterol. Primary bile acids are converted by intestinal bacteria to secondary bile acids, deoxycholic acid and lithocholic acid. A fraction of chenodeoxycholic acid is transformed into the tertiary bile acid ursodeoxycholic acid via 7-ketolithocholic acid. All bile acids secreted by the liver are conjugated either with glycine or with taurine. The bile acid pool re-circulates within the enterohepatic circulation via two physical pumps, the gallbladder and the small intestine, two chemical pumps, the transport system of the hepatocyte and the terminal ileal enterocyte, and two sphincters, the sphincter of Oddi and the ileocecal value. The physical pumps move bile acids independently of their chemical structure, whereas the chemical pumps and the absorptive epithelium discriminates between the different bile acid species. Active transport by the liver and the ileum is more efficient for a trihydroxy bile acid, such as cholic acid, than for a dihydroxy bile acid, such as chenodeoxycholic acid, and is more efficient for conjugated bile acids than for unconjugated bile acids.

The bile acid pool is almost completely confined within the enterohepatic circulation, with less than 1% of the pool present in the peripheral blood. Serum bile acid levels at any moment are determined by the instantaneous balance between intestine absorption and hepatic elimination of bile acids. Input of bile acids from the intestine into the systemic circulation occurs from the hepatic circulation or from portal-systemic shunts, a process which is associated with certain disease states. Therefore, elevated serum bile acid concentration has been shown to be a sensitive maker of hepatic dysfunction.(30) An increase of total serum bile acids usually precedes an elevation of bilirubin in the early onset of liver damage.(31) Although a rise in total serum bile acid can indicate the presence of liver disease, it does not aid in the diagnosis of the type of liver disease.

Cycling of bile acids in the enterohepatic circulation is discontinuous and the determination of the pattern of individual bile acids or the ratio of the primary bile acids (cholic acid to chenodeoxycholic acid) may indicate the type of liver disease.(30) The metabolism of i.v. injected $^{14}C$-cholic acid in patients with cirrhosis showed that the removal of circulating cholic acid in patients with cirrhosis is significantly depressed compared to healthy subjects. Labeled cholic acid was measured in systemic plasma in cirrhosis patients for up to 14 days, compared to near complete clearance of label after only six hours in normal subjects. Similar findings were also obtained by measuring the kinetic clearance of orally administrated $^{14}C$-cholic acid and $^{14}C$-chenodeoxycholic acid in healthy subjects and in patients with cirrhosis. In addition, clinical scoring of the severity of cirrhosis shows that cholic acid synthesis is markedly reduced in early stages of cirrhosis and decreases continuously with the advancement of the liver disease.(32) Therefore, an inverse correlation between synthesis of cholic acid and the severity of cirrhosis was found. In contrast, chenodeoxycholic acid synthesis was shown to be relatively unaffected by cirrhosis. These findings were attributed to a deficiency of one or more enzymes regulating the formation of precursors of cholic acid in patients with cirrhosis. Given current limitations placed on the use of radiolabeled probes, clearance studies of this nature are seldom used in routine clinical practice.

Liver dysfunction after liver transplantation is common during the early post-transplant period. However, it is often difficult to differentiate primary graft dysfunction, preservation injury, rejection, infection, and drug toxicity as the cause of liver cell damage within the graft. It has recently been shown (30) that biliary bile acids reflect graft dysfunction in pediatric liver recipients after liver transplantation. In particular, liver cell damage as a result of preservation injury or rejection lead to a reduction of biliary cholic acid, resulting in a decrease of total biliary bile acids and a decrease in the cholic-to-chenodeoxycholic acid ratio. The cholic-to-chenodeoxycholic acid ratio may be a useful additional parameter in detecting allograft rejection. In this study, cholic acid and chenodeoxycholic acid concentrations in collected bile samples were measured by reversed phase high pressure liquid chromatography which involved labor intensive and expensive laboratory procedures.(30) Therefore, the development of simpler, easier-to-use, and more cost effective methods of measuring and tracking bile acid transport and biotransformation can aid liver transplant research.

Malabsorption of bile acids is found in a wide variety of clinical conditions and is therefore an important functional parameter to monitor. The more commonly found dihydroxy bile salts have a direct effect on the role of sodium absorption and water secretion by the colonic mucosa.(33) Thus, an abnormally high concentration of bile salts in the colon will cause diarrhea, while abnormally low concentration will result in constipation. The diarrhea of severe bile acid malabsorption is a debilitating condition, and patients with even mild cases suffer considerable discomfort and inconvenience. The prevalence of bile acid malabsorption exceeds 1 per 100,000 of the adult population.(34) Despite the fact that effective treatments are available, this condition is substantially under-diagnosed.

Methods to Measure Bile Acids and Bile Acid Kinetics.

Uptake, biliary secretion and potential biotransformation of bile acids are important hepatic functions that play a major role in the digestion and absorption of triglycerides. However, research in this area, as well as clinical treatment by implantation, have been hampered by lack of simple and reliable methods to track bile acid transport.(35)

Current methods to measure bile acid concentrations in collected samples involve cumbersome and expensive laboratory procedures.(30) A first set of these procedures rely on high pressure liquid chromatography (HPLC) techniques to isolate and then measure specific bile acids of interest in collected samples. Given the complexity of HPLC analysis, this approach is not suited for routine clinical screening.

A second approach is to use radioactive labels to evaluate bile acid transport. Radiolabeled bile acids, such as [24-$^{14}$C]-cholic acid taurine ($^{14}$C-CAT),(21,34) and radiolabeled bile acid derivatives, such as $^{75}$Se-homocholic acid taurine ($^{75}$Se-HCAT) which is not currently available in the United States, (36–38) have simplified laboratory procedures permitting the detection of bile acid and its derivatives in biological samples without the need for complex chemical measurement, purification or both.

However, one problem with the use of radiaoactive labeled bile acids is their expense. Not including the costs associated with the assay and radiation disposal, purchase of a radiolabeled bile acid, such as $^{14}$C-cholic acid, can range from $100–250 per test, and the cost for the bile acid derivative $^{75}$Se-homocholic acid taurine ($^{75}$Se-HCAT) can exceed $5,000. Radioactive waste disposal further adds to the cost of using radioactive tags. Although use of these markers is less labor-intensive within the hospital setting, requiring less laboratory preparation before administration and reduced workup after clinical application, the inconvenience of radioactive agents includes the need for special licensing, and compliance with procedures for handling, storage and disposal of contaminated wastes. Moreover, safety issues further restrict their use in certain patient subgroups, such as pregnant woman and young children, and restrict frequency of their use in other subjects to monitor hepatic dysfunction and therapeutic intervention over the time course of the disease. Economic issues also restrict the use of radioactive assays to large facilities able to afford license fees associated with handling radioactive substances. These same barriers also restrict researchers from measuring physiological parameters in experimental models.

A third approach to measuring bile acids concentrations in collected samples relies upon optically-labeled bile acid analogues, such as cholyl-lysyl-fluorescein.(39) Optically-labeled bile acids are as expensive as $^{14}$C-labeled products, however the cost of processing samples adds significantly to the overall cost of the assay since these methods are labor intensive requiring specialized equipment and trained laboratory personnel. In addition, sensitivity and toxicity issues have limited the in vivo application of many of these optically-labeled probes, particularly in humans.

The development of reliable diagnostics to measure bile acid malabsorption and to track bile acid transport and biotransformation in experimental subjects that are cost-effective, easy-to-use and can be safely repeated in patients and research subjects to monitor their response to therapeutic intervention is thus motivated by a set of clear advantages to previous methods. The invention includes a hepatic assay kit comprising one or more bile acids that are each separately labeled with a nonradioactive isotope. Collected samples (tissue biopsies, fecal, and blood samples) are sent for neutron activation, to measure the concentration of each stable isotope labeled bile acid, eliminating the need for the provider to maintain an in-house assay service. For the researcher/clinician, this approach is nonradioactive, and the kit is provided in an off-the-shelf ready-to-use form, thereby freeing the provider from needing special licensing or clinical pharmacy support The results of the assay can be obtained within 24–48 hours. Any clinic, having trained personnel capable of collecting serum and/or fecal samples, can provide this assay service. A hospital setting or specialized department is not needed. Therefore, the kits and assay service can be offered in areas of the country and the world that currently are underserved. In various embodiments, the invention provides a nonradioactive method to directly measure multiply labeled bile acid concentrations in biological material, such as serum and fecal samples, and therefore provides a nontoxic method to measure bile acid transport in research subjects and in humans. Overall, the embodiments of the invention are less labor intensive and less expensive compared to current techniques.

Application of Stable-Isotope Labeling and Neutron Activation to Measurement of Hepatic Receptor Activity.

The inability of current diagnostic techniques to predict liver failure or regeneration has been discussed at length. (40) Functional evaluation of residual hepatocytes is currently done by three types of commonly available tests: (i) Quantitation of serum concentration of substances produced by hepatocytes. (ii) Quantitation of substances released by damaged hepatocytes. (iii) Assessment of hepatic metabolic activity.

Examples of tests in the first category are measurement of serum albumin and measurement of the prothrombin time. Both of these tests are limited because they depend not only on hepatic synthesis of these proteins, but also non-hepatic degradation of the products.

In the second category, the most frequently used assays are those for alanine aminotransferase (ALT) and for aspartate aminotransferase (AST). These serum enzymes are often used as indices for liver cell damage. Although these enzymes are clearly released during hepatocyte damage, the degree of elevation is of little prognostic value.

In the third category are a wide variety of tests used to evaluate hepatic clearance and metabolic function. For example, $^{14}$C-galactose and $^{14}$C-aminopyrine have been used to assess hepatic metabolic reserve. These tests involve measurement of clearance of an exogenously administered radioactive substance. Of particular interest are studies on clearance of endogenous substances such as asialoglycoproteins. These studies reflect the liver's established ability to remove natural asialoglycoproteins from the circulation. In a variety of liver disease states, asialoglycoprotein levels have been shown to be elevated, indicating a decrease in asialoglycoprotein receptor activity.(41) However, changes in synthetic rates of these proteins must also be determined, in order to interpret actual clearance values, making these parameters cumbersome to use as a measure of hepatic function. A final undesirable aspect of these tests is that they involve exposure of the subject patient to radioactivity. The use of radioactivity also makes the tests more labor intensive to perform than non-radioactive tests. Finally, only single measurements can be made at a time without involving tedious separation of multiple $^{14}$C labeled compounds.

Although these currently available tests can provide useful information, all share common weaknesses. Hepatic failure is ultimately dependent on the number of functional hepatocytes present in a given disease state. Current testing methodology is based upon indirect measurements of hepatocyte viability. Direct measurement of hepatocyte activity based upon biological activities such as receptor activity are not commercially available. A hepatocyte directed agent using stable isotope labeling and neutron activation that is an embodiment of the invention, offers the prospect of overcoming this limitation of current diagnostic procedures.

Liver Receptors and Liver Receptor Based Agents.

Much of the technology associated with receptor based diagnostic agents has been in fields associated with MR and SPEC imaging. This technology was developed to measure the distribution of agents that reflect organ function. However, an agent to measure passive distribution in the extracellular space would be desirable for detection of liver lesions.

One class of such compounds are iron chelates that appear to be absorbed by hepatocytes by an unknown biochemical mechanism. An iron derivative has been reported to achieve significant MR signal changes in liver tissue in dogs and rats.(42) However, application of FE-EHPG as a liver contrast agent suffers from two problems. (i) Uptake into liver is inefficient, as only 6% of an administered dose is adsorbed by the liver. (ii) The dose per kilogram of Fe-EHPG needed to achieve liver contrast in rats is 4 to 5 times greater than the currently established level which is an upper limit for its use in humans.(42)

Another class of MR agent, gadolinium-EOB-DTPA, has been used to measure the kinetics of hepatic uptake and biliary excretion. Liver accumulation results from its fast transport into hepatocytes and rate-limited slower transport into bile. Accumulation against a strong concentration gradient suggests an energy dependent transport into hepatocytes, although its mechanism of transport has not been determined.(43)

Ferrite particles have been used as a contrast agent for liver imaging.(44) These commercially available micron sized particles are taken up by the Kupffer cells of liver, and produce effective signal modulation. In recognition that the Kupffer cell may not be the optimal target for hepatic contrast agents, however, a variety of asialoglycoprotein receptor-specific agents (ASGP-R) agents have been developed.

Other assays of liver health and regeneration have been based on epidermal growth factor receptor,(45) LDL receptor gene,(46) laminin-hepatocyte affinity,(47) insulin-like growth factor-II/mannose 6-phosphate receptor,(48) and atrial natiuretic hormone receptor.(49) These preliminary reports require confirmation and further development before use in humans.

Targeting Materials into Hepatocytes Via the Asialoglycoprotein Receptor (ASGP-R).

Receptor-mediated endocytosis via the ASGR-R can rapidly remove from circulation a variety of macromolecules that have a terminal galactose. When such a galactose containing macromolecule is coupled to another moiety of widely differing chemical properties and molecular weight, such a product can rapidly enter hepatocytes via the ASGP-R. These moieties include radioactive isotopes such as technetium 101, and iodine drugs, N-acetyl cysteine, araAMP, and DNA.(50).

ASGP-R have the ability to take up galactose terminated, protein coated ferrite particles in vivo.(51) These particles are taken up preferentially by hepatocytes (70%) and largely avoid uptake by the reticulo-endothelial system (RES). After uptake by hepatocytes, vesicles containing ferrite are magnetically isolated and the proteins of the vesicles are analyzed. For crystal based ferrite material to bind the ASGP-R of hepatocytes, it must penetrate pores of the 100 nm fenestrae characteristic of endothelial cells that lie between the hepatocyte and the circulatory compartment. Particles smaller than 100 nm are needed to serve as hepatocyte directed diagnostic agents.

Josephson et al. synthesized a functionalized superparamagnetic iron oxide colloid (~50 nm) coated with the polygalactosylated polysaccharide arabinogalactan. This colloid is rapidly cleared from the vascular system, and clearance is inhibited by asialofetuin but not by fetuin. The particles are taken up by hepatocytes to an extent greater than 90%. This agent was used as an effective magnetic resonance imaging agent based on its receptor mediated endocytosis through the ASGP-R. Imaging studies using this agent clearly distinguished between normal liver tissue (where the agent was taken up) and liver tumors (where the agent was not taken up; 52, 60). Leveille-Webster et al. used this agent to measure changes in ASGP-R biology during liver regeneration and endotoxemia in rats.(53)

Vera et al. synthesized a gadolinium complex of polydiethylenetriamine pentaacetic acid polyneogalactosyl polylysine which was tested as a paramagnetic contrast agent for MRI of the liver.(54) The agent performed similarly to the arabinogalactan coated superparamagnetic iron oxide of Josephson et al.(60) No further reports of the Vera agent have appeared.

Receptor studies that rely on MR contrast agents are of limited general usefulness because MR imagers are expensive and only a few are available, and application of colloidal MR contrast agents in clinical practice and radiology has not been widely accepted due to cost factors. Further, there is a general perception that colloidal materials used at the concentrations needed for MR imaging elicit adverse reactions in humans.

The most thoroughly studied class of receptor directed agents comprise galactosylated albumin (NGA) labeled with $^{99m}$Tc. A radioactive hepatocyte directed contrast agent was developed (54) that differs from previous colloidal liver contrast agents in that it is taken up specifically by hepatocytes via the ASGPR. The agent has galactose groups attached to albumin, and the glycoprotein is labeled with radioactive technetium. The resulting material is technetium labeled neoglycoalbumin or $^{99m}$Tc-NGA. Technetium sulfur colloid and $^{99m}$Tc-NGA provide different images of the liver using scintigraphic techniques.(54) $^{99m}$Tc-NGA has been used also to study blood clearance and hepatic uptake in normal rats and rats with chloroform induced chronic injury; a quantitative model has been developed in normal humans and patients with cirrhosis, to assess hepatic blood flow and hepatic receptor binding; the utility of $^{99m}$Tc-NGA for assessing functioning mass of the liver has been studied.(55) Other investigators using a combination of blood studies and scintigraphy have reported similar findings with $^{99m}$Tc-NGA.(55, 56)

However, use of $^{99m}$Tc-NGA in the study of liver biology in the research laboratory and the clinic is limited. In research, many investigators have little access to molybdenum/technetium generators, and avoid the use of radioactivity. In the clinic, radioactivity presents a potential hazard to the patient and medical personnel. Scintigraphy relies upon expensive instrumentation, long times of contact between patients and health care workers, and high expense. Use of a single radioactive labeled receptor directed compound such as $^{99m}$Tc-NGA does not permit multiple and simultaneous measurements of a plurality of activities of different receptors.

Better methods to measure hepatic receptor function can aid clinical hepatology both for diagnostic or for prognostic purposes. The development of reliable diagnostic agents and methods to measure functions of receptors in experimental subjects that are cost effective, easy to use and can be safely repeated in patients and research subjects to monitor their response to therapeutic intervention, will have clear advantages over existing methods. Embodiments of the invention provide nonradioactive methods to directly measure single or multiple hepatic receptor activities in research subjects and in humans, an approach will be less labor intensive and less expensive compared to current techniques.

Stable isotope labeling offers a cost effective and technologically feasible approach to dealing with medical needs for multiple receptor measurements and is a current technically feasible solution. Non-radioactive, nontoxic agents, directed to the asialoglycoprotein receptor of hepatocytes by galactose, can be rapidly and specifically removed from the blood as a function of the number of active receptors in the liver. Kinetic modeling of blood depletion of these agents can estimate the number of functioning receptors in the liver. Receptor targeted diagnostic agents, combined with stable isotope labeling and neutron activation, represent a technologically novel general approach to design of agents to measure receptor function in the liver and other organs. Most importantly, stable isotope labeling offers an opportunity to measure multiple receptor activities simultaneously. Other important examples of receptor mediated endocytosis include the transferrin receptor, the low density lipoprotein (LDL) receptor, the mannose 6-phosphate receptor and the mannose receptor.

Application of Stable Isotope Labeling and Neutron Activation to Simultaneous Measurement of Multiple Activities.

Simultaneous measurement of multiple receptor directed agents using stable isotopes and neutron activation is potentiated by diagnostic agents provided herein, biodistribution of which is determined by the ability of these agents to bind to cell surface receptors. This approach applied to measuring liver function and health is described above. The application to measuring other organ receptor activities, and simultaneous measuring receptors from multiple organ systems can be achieved using the concepts presented above for hepatocytes.

Application of Stable-Isotope Labeling and Neutron Activation to the Measurement of Other In Vivo Tests.

Three classes of stable isotope labeled compounds illustrate this technique for measurement of biological functions: (i) low molecular weight compounds (<5000 kDa) represented by chelates of rare earth atoms and chelates of bile acids; (ii) high molecular weight compounds (>5000 kDa) represented by chelates of polysaccharides and proteins; and (iii) colloids. Proteins used herein can be pegylated, i.e., chemically modified by addition of polyethylene glycol (PEG) molecules, to improve characteristics such as stability. PEG addition produces proteins that remain non-toxic and are amphophilic, soluble in water and most organic solvents. Pegylation is achieved via stable covalent bonds between an amino or sulphydryl group of the protein, and a chemically reactive group on the PEG. The reaction can be controlled by procedures known to one of ordinary skill in the art of protein chemistry, giving proteins with a chosen extent of pegylation. Examples of these compounds are presented herein for measuring renal and hepatic function. The application of this technique is not limited by use of a single isotope nor is it limited by the use of labeled compounds of similar molecular weight. A plurality of labeled compounds of varying molecular weight may be combined for administration to a subject, to obtain information simultaneously about multiple organ functions and multiple functions within a single organ. The examples of these compounds in the examples below are for purposes of illustration and specific teaching, and should not be construed to limit application of such compounds or other compounds of similar nature and molecular weight. Examples of the application of this technology for the measurement of biological functions are listed in Table 2.

TABLE 2

Applications of neutron activation and stable isotope labeling for the detection of xenobiotic compounds for measurement of physiological functions and compound biodistribution.

| Organ system and function | Typical compound |
|---|---|
| Renal | |
| Glomerular filtration rate | Sm-DTPA, iohexol |
| Glomerular integrity rate | Sm Ficoll |
| Hepatic | |
| Bile acids | Lu-chelate of cholic acid |
| Low density lipoprotein | SCN-Bz-DOTA-chelate of La—low density lipoprotein |
| Transferrin biodistribution | $^{58}$Fe-transferrin |
| Transferrin receptor activity | $^{58}$Fe-transferrin |
| Asialoglycoprotein receptor activity | Arabinogalactan coated gold colloid |
| Ferritin | $^{58}$Fe-ferritin |
| Pulmonary | |
| Transpulmonary drug delivery | SCN-Bz-DOTA-chelate of La peptide |
| Intestinal transfer | |
| Intestinal transit | Albumin coated gold colloid |
| Intestinal-blood transit | Sm-oxide colloid coated with silane |
| Lymphatics | $^{58}$Fe-labeled iron oxide colloid |
| Measurement of fluid volumes in different body fluid compartments | |
| Application of the indicator-dilution principle | SCN-Bz-DOTA-chelate of La—albumin |
| Extracellular fluid volume | Na, Cl, Br |
| Plasma volume | Human-DTPA-Sm Albumin |

Embodiments of the invention are further illustrated by the following Examples. In one example, a method of determining the glomerular filtration rate of a subject comprises [1] obtaining a serum sample $S_{pre}$ and a urine sample $U_{pre}$ from a subject; [2] administering to the subject an amount of a stable-isotope labeled substance that is filtered by the kidneys and is readily detectable by neutron activation in serum and urine; [3] allowing for the concentration of the substance to equilibrate between the blood and the extravascular spaces; [4] separating an aliquot of the urine sample $v_A$ and obtaining a serum sample from the subject at the time $t_A$; [5] calculating a urine rate $(v/a)_A$ from the formula $(v/a)_A = V_A/a_A$; [6] measuring the concentrations of stable isotope in the serum and urine samples by neutron activation analysis; and [7] calculating GFR from the formula $$GFR = \sum_{i=1}^{p} 2 \times [SI]_{U_{i+1}} \times v_{i+1} / ([SI]_{S_i} + [SI]_{S_{i+1}}) / p$$

Methods are also presented for measuring bile acid movement throughout the body and for measuring receptor activity.

More generally, methods are presented wherein the concentration of multiple stable-isotope labeled compounds may be determined simultaneously in living subjects and their excretory products by in vitro measurements using neutron activation. Compositions containing single or multiple normal-abundance stable-isotope labeled compounds, and compositions containing single or multiple enriched stable isotope labeled compounds and compositions are described.

These compositions may be determined individually or simultaneously in living subjects and their excretory products, by in vitro measurements using neutron activation. In embodiments, the invention provides a method for in vitro evaluation of the clearance rate or concentration of either naturally occurring compounds which contain certain stable-isotopes, or xenobiotics bearing certain stable-isotopes administered to and subsequently assayed in samples obtained from a living subject, thereby providing a noninvasive method for determining parameters exemplified by [1] the blood volume, [2] the status of the excretory organs of the subject, and [3] a proper dosing regimen of a pharmacologically active compound to be administered to the subject.

The invention having now been fully described, the examples below are presented to illustrate various embodiments in detail, and do not to limit the scope of the invention. References cited are hereby incorporated by reference herein.

EXAMPLES

General Procedure of Measuring Blood Clearance

The method of the invention may be used to monitor the blood clearance mechanisms mediated by, for example, liver receptors and kidney function of a subject/patient and thereby provide information regarding the functioning of these mechanisms. Test substances designed to assess organ function, each labeled with a stable isotope may be injected into a subject either as a bolus or a constant infusion. In general, the expected relationships between test substance blood concentration as a function of time are shown in FIGS. 3 (bolus injection) and 4 (constant infusion). FIG. 3 illustrates that, following a bolus injection of the test compound, the blood concentration of the test compound increases sharply, and then decreases over time until reaching its preinjection concentration in a normal subject. When organ impairment (e.g. kidney failure) occurs, the blood concentration of the test compound will decrease more slowly and take a longer time to reach preinjection levels than with normal organ function. In rare cases, organ function may be increased compared to normal function, in which case test substance blood concentration will decline more rapidly than in a normal subject.

FIG. 4 illustrates that, following a constant infusion of the test compound, the measured blood concentration of the test compound increases sharply, and then becomes constant for a normal patient at steady state where the excretion rate equals the rate of infusion. When organ impairment (e.g. kidney failure) occurs, the value of test compound will continue to increase over time.

Having now generally described applications that are embodiments of this invention, embodiments will be better understood by reference to certain specific examples, which are included herein for purposes of illustration only and are not intended to be limiting of any embodiment thereof, unless so specified.

Examples 1–6 show the addition of stable isotope to sample tubes for monitoring and correcting for neutron flux variation in each sample tube. Example 6 demonstrates chemical bar coding, used to assign lot numbers to sample tubes.

Examples 7–36 relate to the measurement of glomerular filtration rate (GFR) using stable isotopes. Examples 7 through 25 illustrate the formation of various chelates of natural abundance stable isotope metals. The examples show two chelates and three stable isotopes.

Examples are presented to demonstrate that gadolinium chelates detected by NMR properties or atomic absorbance, and various stable isotope chelates detectable by neutron activation, have nearly identical properties with respect to: chelate formation (Examples 20–21; 26–27); stability (Examples 20–21; 26–27); charge as reflected by their chromatography on a cation chromatographic support (Examples 16–19; 24–25); and biological properties as indicated by blood excretion and urine accumulation (Examples 29–30).

Example 28 illustrates the formation of various chelates of stable isotope metals using enriched abundance of the stable isotopes of the various elements. The similarity of chelate formation, chromatography and stability between corresponding pairs of natural and enriched abundance can be seen by comparing respective data from corresponding Examples. The only difference between the pairs of chelates is that the enriched isotope member is proportionately more detectable based on the increased proportion of the stable isotope.

Examples 29 through 33 show the kinetics of blood depletion and urine accumulation of stable isotope labeled chelates in the rat. The results show the near identical properties of gadolinium chelates detected by NMR properties or atomic absorbance and various stable isotope chelates detectable by neutron activation. The similarity of the two types of chelates regarding formation of chelates, stability of chelates, and chromatography (i.e., based on charge) of the chelates is shown.

Example 36 represents the results of a study measuring the GFR in a rabbit model using iohexol as the low molecular weight compound bearing a stable isotope, in this case $^{127}$I. The results are consistent with previous reports using a variety of other methods and compounds to measure GFR.

Example 37 represents the results of a hypothetical study in humans, comparing GFR measured using Sm-DTPA (determined by neutron activation) with two other methods ($^{99m}$Tc-DTPA and Gd-DTPA). Based on the near identical physical, chemical and biological properties of the three chelates, identical GFR measurements for the three compounds in humans are expected.

The following examples provide data on human glomerular filtration rates (GFR) obtained by practicing a method of this invention that relies on the measurement of the clearance of Sm-DTPA and Gd-DTPA (Magnevist, Berlex Laboratories) from the serum and urine of a patient. Results obtained from 35 patients show good correlation with GFR rates determined by prior art methods such as the $^{99m}$Tc-DTPA clearance test.

Examples 38–51 relate to Glomenilar Sieving Assays (Glomerular Integrity Rate). Examples are presented for Ficoll, and similar chemistry can be effected using other polysaccharides, such as dextran and pullulan. Examples are also presented for protein labeling with stable isotopes for applications in Glomerular Sieving Assays.

Examples 52–55 show assays of formation of stable isotope labeled chelate and stability of labeled Ficoll and inulin.

Example 56 illustrates the use of multiple stable isotope labeled compounds to perform multiple bioassays simultaneously.

Examples 57 through 62 illustrate labeling of low molecular weight molecules with stable isotope metals. The examples demonstrate the application of bile acids for measuring liver function. The examples are presented merely to exemplify labeling low molecular weight compounds for measuring biological functions, and are in no way intended to limit the scope of the present claims.

Example 63 shows the results of a hypothetical study in humans comparing the clearance rate of stable isotope labeled Sm-cholic acid and radiolabeled cholic acid in patients with Laennec's cirrhosis and in healthy subjects. Based on the similar physical, chemical and biological properties of these agents, data showing identical clearance rates in humans are expected. The example provides data on human bile acid clearance rates obtained by practicing a method that is an embodiment of this invention that relies on measurement of the clearance of Sm-cholic acid from the serum of patients. Results obtained from 16 patients show good correlation with clearance rates determined by prior art methods such as $^{14}$C-cholic acid clearance test.

Example 64 shows the results of a hypothetical study in humans comparing the clearance rate of Sm-taurocholic acid (Sm-TCA) and radiolabeled $^{75}$Se-homocholic acid taurine ($_{75}$SeHCAT), a synthetic analog of taurocholic acid, in patients with diarrhea of unknown cause. Based on the similar physical, chemical and biological properties of these agents, observation of identical clearance rates in humans is expected. The following examples provide data on human bile acid clearance rates obtained by practicing the method of this invention that relies on the measurement of the clearance of Sm-TCA from the stool of patients. Results obtained from 20 patients show good correlation with clearance rates determined by prior art methods, such as $^{75}$SeHCAT assayes.

Examples 65–68 illustrate the synthesis of colloids labeled with stable isotopes. Results similar to Examples 65 and 66 may be obtained by substituting other polysaccharides such as dextran, starch, hydroxyethyl starch, pullulan and other similar polymers for arabinogalactan, whereby one can obtain colloids labeled with stable isotopes and having different surface properties.

Example 69 shows the measurement of receptor activity using colloidal gold coated with a plurality of galactose moities.

Example 1

Post Labeling Sample Tubes with Monitor (Use of an Internal Standard to Correct for Neutron Flux Variation Between Samples)

This example illustrates the procedure for the use of an internal monitor to correct for neutron flux variation between sample tubes.

Tubes containing samples of samarium (10 µg), lutetium (10 µg), gold (10 µg) and arsenic (1 µg) for neutron activation were prepared by pipetting 100 µl of an aqueous solution of samarium, lutetium, and gold chloride and 25 µl of lithium arsenate-hexafluride into the bottom of each tube. The water was removed by heating the tubes at 70° C. for 12 hours. The tubes were exposed to a 2 megawatt neutron flux for 15 minutes. Five days later the tubes were counted for three minutes. Column 1 and 2 of Table 3 show the disintegrations per minute (dpm) and the correction factor calculated for the arsenic monitor. Since identical amounts of arsenic were added to each tube, all counts should be identical except for variation in neutron flux between tubes. An ideal count rate of 27984 was assumed and the correction factor (Column 2) is obtained by dividing each dpm of column 1 into 27984. Columns 3 through 8 show the dpm measured for 20 identical samarium, lutetium, and gold samples, respectively, before and after correction for neutron flux. For instance, column 4 is obtained by multiplying Column 3 by the factor in Column 2. The standard deviation and coefficient of variation for each set of data are shown at the bottom of each Column. Significant improvement in the between sample dpm values for tubes corrected for neutron flux was observed.

TABLE 3

Use of an arsenic monitor as an internal standard (in dpm except for correction factor)

| Arsenic monitor | Correction factor | Samarium | | Gold | | Lutetium | |
|---|---|---|---|---|---|---|---|
| | | Uncorrected | Corrected | Uncorrected | Corrected | Uncorrected | Corrected |
| 27984 | 1.000 | 1836720.0 | 1836720.0 | 2222340.0 | 2222340.0 | 716520.0 | 716520.0 |
| 30530 | 0.917 | 2057460.0 | 1885881.4 | 2508480.0 | 2299289.4 | 813180.0 | 745366.2 |
| 27346 | 1.023 | 1803420.0 | 1845495.0 | 2178900.0 | 2229735.2 | 715200.0 | 731886.1 |
| 33311 | 0.840 | 2141880.0 | 1799356.7 | 2669520.0 | 2242618.0 | 839100.0 | 704913.5 |
| 20189 | 1.386 | 1325460.0 | 1837221.9 | 1578960.0 | 2188598.6 | 503490.0 | 697888.2 |
| 35077 | 0.798 | 2339040.0 | 1866057.4 | 2841840.0 | 2267185.1 | 913020.0 | 728396.1 |
| 41825 | 0.669 | 2787780.0 | 1865229.8 | 3412560.0 | 2283253.5 | 1075080.0 | 719307.6 |
| 32157 | 0.870 | 2110380.0 | 1836516.9 | 2553420.0 | 2222063.8 | 825780.0 | 718618.9 |
| 29882 | 0.936 | 2000640.0 | 1873566.4 | 2426640.0 | 2272508.3 | 790140.0 | 739953.1 |
| 49091 | 0.001 | 3242220.0 | 1848206.1 | 4031100.0 | 2297901.9 | 1233480.0 | 703137.1 |
| 42308 | 0.661 | 2797320.0 | 1850245.9 | 3421800.0 | 2263298.9 | 1110540.0 | 734550.2 |
| 44733 | 0.626 | 2940120.0 | 1839275.7 | 3656700.0 | 2287552.7 | 1140840.0 | 713684.9 |
| 44638 | 0.627 | 2986740.0 | 1872416.6 | 3649800.0 | 2288095.4 | 1146540.0 | 718777.2 |
| 37048 | 0.755 | 2450700.0 | 1851122.6 | 2951400.0 | 2229323.5 | 928440.0 | 701292.0 |
| 42363 | 0.661 | 2895300.0 | 1912567.0 | 3343320.0 | 2208518.4 | 1118160.0 | 738630.2 |
| 49074 | 0.570 | 3309240.0 | 1887063.0 | 4076460.0 | 2324564.1 | 1261620.0 | 719427.3 |
| 33246 | 0.842 | 2358240.0 | 1984990.3 | 2797860.0 | 2355029.6 | 953160.0 | 802298.9 |
| 42209 | 0.663 | 2845260.0 | 1886369.2 | 3400980.0 | 2254804.1 | 1072500.0 | 711053.1 |
| 45029 | 0.621 | 2980260.0 | 1852130.8 | 3687000.0 | 2291345.8 | 1106820.0 | 687851.2 |
| 45244 | 0.619 | 2965800.0 | 1834385.7 | 3685020.0 | 2279232.6 | 1196220.0 | 739877.6 |
| 45676 | 0.613 | 3025320.0 | 1853501.9 | 3673080.0 | 2250360.6 | 1140780.0 | 698913.8 |

TABLE 3-continued

Use of an arsenic monitor as an internal standard (in dpm except for correction factor)

| Arsenic monitor | Correction factor | Samarium | | Gold | | Lutetium | |
|---|---|---|---|---|---|---|---|
| | | Uncorrected | Corrected | Uncorrected | Corrected | Uncorrected | Corrected |
| | | 2533300.0 | 1862777.2 | 3084151.4 | 2264648.5 | 980981.4 | 722492.5 |
| | | 528328.8 | 36336.3 | 661646.1 | 39201.1 | 197789.8 | 23719.8 |
| | | 20.85 | 1.95 | 21.45 | 1.73 | 20.16 | 3.28 |

Example 2

Effect of Placement of Monitor in Various Locations within the Sample Tube when Used to Correct for Sample Count Rate This example illustrates the importance of locating neutron flux monitor in identical positions within each tube, and counting each tube with the same geometry.

A sample of 100 µl of arsenic monitor containing, for example, 10 µg As is added to each of three tubes, at the bottom of the tube (tube 1), the middle of the tube (tube 2), or in the cap of the tube (tube 3). The water is removed by heating at 70° C. allowing the monitor to be deposited as a dry film. Next, 100 µl of samarium (10 ng) is added to the bottom of each tube without disturbing the monitor and the water is removed by heating. Samarium and arsenic solutions are prepared as in Example 1. The three tubes are taped together and exposed to a 1 megawatt neutron flux for 15 minutes. Since the sample tubes are close enough together to assure that neutron flux is experimentally constant across the three tubes, all tubes receive the same level of neutron flux. Three days later the tubes are counted for three minutes by placing the bottom of each tube on the surface of the detector face. Results are shown in Table 4.

The correction factor (Column 2 and its application to Column 3 to yield Column 4 are obtained as described in Example 1.

TABLE 4

Effect of locating neutron flux monitor in the different position within sample tubes on the apparent dpm produced by a constant amount of samarium located in the same position in the sample tubes. The experiment was performed as described in Example 2.

| Arsenic Monitor (location) dpm | Correction factor | Samarium uncorrected for neutron flux Dpm | Samarium corrected for neutron flux dpm |
|---|---|---|---|
| 1152 (bottom) | 0.868 | 5625 | 4882 |
| 853 (middle) | 1.172 | 5657 | 6630 |
| 647 (top) | 1.546 | 5583 | 8631 |

Example 3

Pre-Labeling Sample Tubes with Arsenic Monitor (Internal Standard to Correct for Neutron Flux Variation Between Samples)

This example illustrates the technical advantage obtained by placing monitor in the sample tube before placing sample in the tube. This assures that the monitor is located in the same position within each tube. Second, the monitor is placed in the tube before the tube is supplied to the customer reducing the need to handle sample tubes upon receiving them for neutron activation.

Sample tubes were labeled with arsenic (an example of an stable isotope that can serve as an internal monitor) by dissolving 10 mg of lithium hexafluoroarsenate in 100 ml of water soluble polyurethane and pipetting 50 µl of the mixture into each tube. The contents were added to each tube to assure location at the bottom of the tube. The tube contents were solidified by air drying at room temperature for five days.

Example 4

Pre-Labeling Sample Tubes with Samarium Monitor (Internal Standard to Correct for Neutron Flux Variation Between Samples)

Sample tubes are labeled with samarium (an example of an stable isotope that can serve as an internal monitor) by dissolving 5 mg of samarium-DTPA in 100 ml of water soluble polyurethane and pipetting 50 µl of the mixture into each tube. The contents are added to or provided in each tube such that maintaining the contents at a location at the bottom of the tube is assured. The tube contents are solidified by air drying at room temperature for five days.

Example 5

Pre-Labeling Sample Tubes with Iridium Monitor (Internal Standard to Correct for Neutron Flux Variation Between Samples)

Sample tubes are labeled with iridium (an example of an stable isotope that can serve as an internal monitor) by dissolving 10 mg of iridium-DTPA in 100 ml of 0.1% aqueous polyvinyl alcohol and pipetting 50 µl of the mixture into the cap of each tube. The contents are added to or provided in each tube such that maintaining the contents at a location at the top of the tube is assured. The tube contents are solidified by drying at 80° C. for 8 hours.

Example 6

Chemical Bar Coding Using Stable Isotopes

In this illustrative example sample tubes are pre-labeled with arsenic (as internal monitor) and varying amounts of bromine and lanthanum to represent 10 lots of tubes. As can be seen in Table 5, each lot allows discreet identification of the ten sets of tubes by measuring the dpm of the three elements. By increasing the range of dpms for bromine and lanthanum and by the addition of a fourth element such as ytterbium, it is seen that a very large number of tube lot labeling combinations can be established. Tubes may be labeled with the various elements using methods described in Examples 3–5.

TABLE 5

Identification of tubes by chemical bar coding using multiple stable isotope.

| Lot # | Arsenic | Bromine Dpm | Lanthanum | Ytterbium |
|---|---|---|---|---|
| 1 | 1000 | 500 | 1000 | 0 |
| 2 | 1000 | 1000 | 1000 | 0 |
| 3 | 1000 | 1500 | 1000 | 0 |
| 4 | 1000 | 2000 | 1000 | 0 |
| 5 | 1000 | 2500 | 1000 | 0 |
| 6 | 1000 | 500 | 2000 | 0 |
| 7 | 1000 | 1000 | 2000 | 0 |
| 8 | 1000 | 1500 | 2000 | 0 |
| 9 | 1000 | 2000 | 2000 | 0 |
| 10 | 1000 | 2500 | 2000 | 0 |

Example 7

Preparation of Reagents

Reagents were prepared as indicated in Table 6.

TABLE 6

Preparation of reagents

| Reagent | Compound | Source | Amount | Fill to final volume with deionized water, ml | Adjust pH to with |
|---|---|---|---|---|---|
| 0.01 MDTPA | DTPA[a] | SIGMA | 393.5 mg | 10 | pH to 6.95 with LiOH |
| 0.1 M DOTA | DOTA[b] | Macrocyli cs | 481 mg | 10 | pH to 7.8 with LiOH |
| | CM[c] sephadex | SIGMA | 12 g | 100 | |
| 1 M SaCl$_3$ | Samarium chloride hexahydrate | Aldrich | 3.6 g | 10 | 6N HCl to dissolve |
| 1 M LaCl$_3$ | Lanthanum chloride, heptahydrate | Aldrich | 3.7 g | 10 | |
| 1 M EuCl$_3$. | Europium chloride hexahydrate | Aldrich | 3.7 g | 10 | |
| 1 M GdCl$_3$ | Gadolinium chloride | Aldrich | | | |
| 1 M Tris buffer | Trizma base | SIGMA | 12.11 g | 100 | 7.5 with 12 N HCl |
| 0.01 M Tris buffer | 1 M Tris buffer | | 1 ml | 99 | |

[a]DTPA stands for diethylenetriamine pentaacetic acid.
[b]DOTA stands for tetraazacyclododecanetetraacetic acid.
[c]CM stands for carboxymethyl.

Example 8

Preparation of 1 mM Gd-DTPA Chelate and 1 mM GdCl$_3$

Preparation of chelate of gadolinium and DTPA. To a 15 ml plastic centrifuge tube add in the following order: 1 ml of 1M Tris buffer pH 7.5, 0.11 ml of 0.1 M DTPA (pH 6.5), 0.01 ml of 1 M GdCl$_3$ and 9 ml deionized water. Contents are mixed, and incubated about 5 to about 45 minutes (for example, about 30 minutes) at room temperature. The pH of the solution was 7.52.

Preparation of Gadolinium chloride solution. To a 15 ml plastic centrifuge tube add the following order: 1 ml of 1M Tris buffer pH 7.5, 0.01 ml of 1M GdCl$_3$ and 9 ml water. Contents are mixed, and incubated 30 to 45 minutes at room temperature. The pH of the solution was 7.54.

Example 9

Preparation of 1 mM Sm-DTPA Chelate and 1 mM SmCl$_3$

Preparation of chelate of samarium and DTPA. To a 15 ml plastic centrifuge tube reagents were added in the following order: 1 ml of 1M Tris buffer pH 7.5, 0.11 ml of 0.1 M DTPA (pH 6.5), 0.01 ml of 1 M SmCl$_3$ and 9 ml deionized water. Contents are mixed, and incubated 5 to 45 minutes (for example, 30 minutes) at room temperature. The pH of the solution was 7.52.

Preparation of samarium chloride solution. To a 15 ml plastic centrifuge tube reagents were added in the following order: 1 ml of 1M Tris buffer pH 7.5, 0.01 ml of 1M SmCl$_3$ and 9 ml water. Contents are mixed, and incubated 30 to 45 minutes at room temperature. The pH of the solution was 7.54.

Example 10

Preparation of 1 mM La-DTPA Chelate and 1 mM LaCl$_3$

Preparation of chelate of lanthanum and DTPA. To a 15 ml plastic centrifuge tube reagents were added in the following order: 1 ml of 1M Tris buffer pH 7.5, 0.11 ml of 0.1 M DTPA (pH 6.5), 0.01 ml of 1 M LaCl$_3$ and 9 ml deionized water. Contents are mixed, and incubated 5 to 45 minutes (for example, 30 minutes) at room temperature. The pH of the solution was 7.52.

Preparation of lanthanum chloride solution. To a 15 ml plastic centrifuge tube were added in the following order: 1 ml of 1M Tris buffer pH 7.5, 0.01 ml of 1M LaCl$_3$ and 9 ml water. Contents are mixed, and incubated 30 to 45 minutes at room temperature. The pH of the solution was 7.5.

Example 11

Preparation of 1 mM EU-DTPA Chelate and 1 mM EuCl$_3$

Preparation of chelate of europium and DTPA. To a 15 ml plastic centrifuge tube reagents were added in the following order: 1 ml of 1M Tris buffer pH 7.5, 0.11 ml of 0.1 M DTPA (pH 6.5), 0.01 ml of 1 M EuCl$_3$ and 9 ml deionized water. Contents are mixed, and incubated 5 to 45 minutes (for example, 30 minutes) at room temperature. The pH of the solution was 7.52.

Preparation of europium chloride solution. To a 15 ml plastic centrifuge tube reagents were added in the following order: 1 ml of 1M Tris buffer pH 7.5, 0.01 ml of 1M EuCl$_3$ and 9 ml water. Contents are mixed, and incubated 30 to 45 minutes at room temperature. The pH of the solution was 7.5.

Example 12

Preparation of 1 mM Gd-DOTA Chelate

Preparation of chelate of gadolinium and DOTA. To a 15 ml plastic centrifuge tube reagents were added in the following order: 1 ml of 1M Tris buffer pH 7.5, 0.11 ml of 0.1 M DOTA (pH 7.8), 0.01 ml of 1 M GdCl$_3$ and 9 ml deionized water. Contents are mixed, and incubated 5 to 45 minutes (for example, 30 minutes) at room temperature. The pH of the solution was 7.5.

Example 13

Preparation of 1 mM Sm-DOTA Chelate

Preparation of chelate of samarium and DOTA. To a 15 ml plastic centrifuge tube reagents were added in the following order: 1 ml of 1M Tris buffer pH 7.5, 0.11 ml of 0.1 M DOTA (pH 7.8), 0.01 ml of 1 M SmCl$_3$ and 9 ml deionized water. Contents are mixed, and incubated 5 to 45 minutes (for example, 30 minutes) at room temperature. The pH of the solution was 7.5.

Example 14

Preparation of 1 mM La-DOTA Chelate

Preparation of chelate of lanthanum and DOTA. To a 15 ml plastic centrifuge tube reagents were added in the following order: 1 ml of 1M Tris buffer pH 7.5, 0.11 ml of 0.1 M DOTA (pH 7.8), 0.01 ml of 1 M LaCl$_3$ and 9 ml deionized water. Contents are mixed, and incubated 5 to 45 minutes (for example, 30 minutes) at room temperature. The pH of the solution was 7.5.

Example 15

Preparation of 1 mM Eu-DOTA Chelate

Preparation of chelate of europium and DOTA. To a 15 ml plastic centrifuge tube reagents were added in the following order: 1 ml of 1M Tris buffer pH 7.5, 0.11 ml of 0.1 M DOTA (pH 7.8), 0.01 ml of 1 M EuCl$_3$ and 9 ml deionized water. Contents are mixed, and incubated 5 to 45 minutes (for example, 30 minutes) at room temperature. The pH of the solution was 7.5.

Example 16

Assay of Gd-DTPA Chelate

Preparation of carboxymethyl sephadex column. To two 10 ml plastic pipets cut off at the 3 ml mark and plugged with glass wool at the bottom add enough slurry to form a 2 ml volume of the CM sephadex. Wash the packed resin with 6 ml of 1 M Tris buffer pH 7.5, and 6 ml of 0.01M Tris buffer pH 7.5. Dilute samples (1:10) (gadolinium-DTPA or gadolinium chloride) from Example 8 with distilled water (0.2 ml to 2 ml). Collect the eluants of fractions as follows. Fraction 1. 3 ml of 0.01 M Tris buffer pH 7.5 and allow to drain into column. Fraction 2. 1 ml of sample (gadolinium-DTPA or gadolinium chloride) and allow to drain into column. Apply 3 ml of 0.01 M Tris buffer pH 7.5 and allow to drain into column. Fraction 3. 3 ml of 0.01M Tris buffer pH 7.5 and allow to drain into column. Dry all fractions at 70° C. for 76 hours, dissolve in 1 ml of 1 mM HCl and assay by atomic absorption.

TABLE 7

| Assay of Gd-DTPA chelate | | |
| --- | --- | --- |
| Gadolinium-DTPA from Example 8 | | |
| Fraction # | Fraction description | % of total |
| 1 | 3 ml of 0.01M Tris buffer pH 7.5 | 0 |
| 2 | 1 ml of diluted Gd-DTPA from Example 8 diluted 1:10 followed by 3 ml of 0.01M Tris buffer pH 7.5 | 100 |
| 3 | 3 ml of 0.01M Tris buffer pH 7.5 | 0 |
| Gadolinium chloride from Example 8 | | |
| Fraction # | Fraction description | % of total |
| 1 | 3 ml of 0.01M Tris buffer pH 7.5 | 0 |
| 2 | 1 ml of GdCl$_3$ from Example 8 diluted 1:10 followed by 3 ml of 0.01M Tris buffer pH 7.5 | 0 |
| 3 | 3 ml of 0.01M Tris buffer pH 7.5 | 0 |

Results: Table 7 shows that 100% of Gd-DTPA is eluted from the CM-Sephadex column as expected for a negatively charged molecule. In contrast, 100% of unchelated Gd$^{+3}$ is retained on the column as expected for a positive ion. These results demonstrate that the DTPA chelate of Gd$^{+3}$ forms within 5 minutes, and that this method can be used to ascertain the formation of metal DTPA chelates.

Example 17

Assay of Sm-DTPA Chelate

Preparation of carboxymethyl Sephadex column. To two 10 ml plastic pipets which had been cut off at the 3 ml mark and plugged with glass wool at the bottom, enough slurry was added to form a 2 ml volume of the CM Sephadex. The packed resin was wash with 6 ml of 1 M Tris buffer pH 7.5, and 6 ml of 0.01M Tris buffer pH 7.5. The samples prepared in Example 9 (samarium-DTPA or samarium chloride) were diluted 1:10 with distilled water (0.2 ml to 2 ml). Fractions were applied as follows. Fraction 1. Three ml of 0.01 M Tris buffer pH 7.5 and allow to drain into column. Fraction 2. One ml of sample (samarium-DTPA or samarium chloride) and allow to drain into column. Apply 3 ml of 0.01 M Tris buffer pH 7.5 and allow to drain into column. Fraction 3. Three ml of 0.01M Tris buffer pH 7.5 and allow to drain into column. Collect the eluant of fractions 1 through 3. Fraction 4. Column and contents. All fractions were dried at 70° C.

for 76 hours and 25 μl of arsenic internal standard was added. Samples were activated by exposure to a neutron flux in a 2 megawatt reactor for 15 minutes. After three days each sample was counted for 3 minutes.

TABLE 8

Assay of Sm-DTPA chelate

Samarium-DTPA from Example 9

| Fraction # | Fraction description | dpm | % of total |
|---|---|---|---|
| 1 | 3 ml of 0.01M Tris buffer pH 7.5 | 0 | 0 |
| 2 | 1 ml of diluted Sm-DTPA from Example 9 diluted 1:10 followed by 3 ml of 0.01M Tris buffer pH 7.5 | 148208 | 97 |
| 3 | 3 ml of 0.01M Tris buffer pH 7.5 | 19089 | 1 |
| 4 | Column and contents | 24257 | 2 |

Samarium chloride from Example 9

| Fraction # | Sample description | dpm | % of total |
|---|---|---|---|
| 1 | 3 ml of 0.01M Tris buffer pH 7.5 | 0 | 0 |
| 2 | 1 ml of SmCl$_3$ from Example 9 diluted 1:10 followed by 3 ml of 0.01M Tris buffer pH 7.5 | 0 | 0 |
| 3 | 3 ml of 0.01M Tris buffer pH 7.5 | 0 | 0 |
| 4 | Column and contents | 1128598 | 100 |

Results: Table 8 shows that 98% of Sm-DTPA is eluted from the CM-Sephadex column as expected for a negatively charged molecule. In contrast 100% of unchelated $Sm^{+3}$ is retained on the column as expected for a positive ion. These results demonstrate that the DTPA chelate of $Sm^{+3}$ forms within 5 minutes, and that this method can be used to ascertain the formation of metal DTPA chelates. These examples show that the DTPA chelate of samarium and the DTPA chelate of gadolinium have identical chromatographic behavior.

Example 18

Assay of La-DTPA Chelate

Preparation of carboxymethyl Sephadex column. To two 10 ml plastic pipets which were cut off at the 3 ml mark and plugged with glass wool at the bottom, enough slurry was added to form a 2 ml volume of the CM Sephadex. The packed resin was washed with 6 ml of 1 M Tris buffer pH 7.5, and 6 ml of 0.01M Tris buffer pH 7.5. The samples prepared in Example 10 (lanthanum-DTPA or lanthanum chloride) were diluted 1:O with distilled water (0.2 ml to 2 ml). Fractions were applied as follows. Fraction 1. Three ml of 0.01 M Tris buffer pH 7.5 and allow to drain into column. Fraction 2. One ml of sample (lanthanum-DTPA or lanthanum chloride) and allow to drain into column. Apply 3 ml of 0.01 M Tris buffer pH 7.5 and allow to drain into column. Fraction 3. Three ml of 0.01M Tris buffer pH 7.5 and allow to drain into column. Collect the eluant of fractions 1 through 3. Fraction 4. Column and contents. All fractions were dried at 70° C. for 76 hours, and 25 μl of arsenic internal standard was added. Samples were activated by exposure to a neutron flux in a 2 megawatt reactor for 15 minutes. After three days, each sample was counted for 3 minutes.

TABLE 9

Assay of La-DTPA chelate

Lanthanum-DTPA from Example 10

| Fraction # | Sample description | dpm | % of total |
|---|---|---|---|
| 1 | 3 ml of 0.01M Tris buffer pH 7.5 | 0 | 0 |
| 2 | 1 ml of La-DTPA from Example 10 diluted 1:10 followed by 3 ml of 0.01M Tris buffer pH 7.5 | 489692 | 100 |
| 3 | 3 ml of 0.01M Tris buffer pH 7.5 | 0 | 0 |
| 4 | Column and contents | 0 | 0 |

Lanthanum chloride from Example 10

| Fraction # | Sample description | DPM | % of total |
|---|---|---|---|
| 1 | 3 ml of 0.01M Tris buffer pH 7.5 | 0 | 0 |
| 2 | 1 ml of LaCl$_3$ from Example 10 diluted 1:10 followed by 3 ml of 0.01M Tris buffer pH 7.5 | 0 | 0 |
| 3 | 3 ml of 0.01M Tris buffer pH 7.5 | 0 | 0 |
| 4 | Column and contents | 254172 | 100 |

Results: Table 9 shows that 100% of La-DTPA is eluted from the CM-Sephadex column as expected for a negatively charged molecule. In contrast, 100% of unchelated $La^{+3}$ is retained on the column as expected for a positive ion. These results demonstrate that the DTPA chelate of $La^{+3}$ forms within 5 minutes. These examples show that the DTPA chelate of lanthanum and the DTPA chelate of gadolinium have identical chromatographic behavior.

Example 19

Assay of Eu-DTPA Chelate

Preparation of carboxymethyl Sephadex column. To two 10 ml plastic pipets which were cut off at the 3 ml mark and plugged with glass wool at the bottom, enough slurry was added to form a 2 ml volume of the CM Sephadex. The packed resin was washed with 6 ml of 1 M Tris buffer pH 7.5, and 6 ml of 0.01M Tris buffer pH 7.5. The samples prepared in Example 11 (europium-DTPA or Europium chloride) were dilute 1:10 with distilled water (0.2 ml to 2 ml). Fractions were applied as follows. Fraction 1. Three ml of 0.01 M Tris buffer pH 7.5 and allow to drain into column. Fraction 2. One ml of sample (Europium-DTPA or Europium chloride) and allow to drain into column. Apply 3 ml of 0.01 M Tris buffer pH 7.5 and allow to drain into column. Fraction 3. Three ml of 0.01M Tris buffer pH 7.5 and allow to drain into column. Collect the eluant of fractions 1 through 3. Fraction 4. Column and contents. All fractions were dried at 70° C. for 76 hours and 25 μl of arsenic internal standard was added. Samples were activated by exposure to a neutron flux in a 2 megawatt reactor for 15 minutes. After three days each sample was counted for 3 minutes.

TABLE 10

Assay of Eu-DTPA chelate

Europium-DTPA from Example 11

| Fraction # | Sample description | dpm | % of total |
|---|---|---|---|
| 1 | 3 ml of 0.01M Tris buffer pH 7.5 | 0 | 0 |
| 2 | 1 ml of Eu-DTPA from Example 11 diluted 1:10 followed by 3 ml of 0.01M Tris buffer pH 7.5 | 22115 | 100 |

TABLE 10-continued

Assay of Eu-DTPA chelate

| | | dpm | % of total |
|---|---|---|---|
| 3 | 3 ml of 0.01M Tris buffer pH 7.5 | 0 | 0 |
| 4 | Column and contents | 0 | 0 |

Europium chloride from Example 11

| Fraction # | Sample description | dpm | % of total |
|---|---|---|---|
| 1 | 3 ml of 0.01M Tris buffer pH 7.5 | 0 | 0 |
| 2 | 1 ml of EuCl$_3$ from Example 11 diluted 1:10 followed by 3 ml of 0.01M Tris buffer pH 7.5 | 0 | 0 |
| 3 | 3 ml of 0.01M Tris buffer pH 7.5 | 0 | 0 |
| 4 | Column and contents | 21244 | 100 |

Results: Table 10 shows that 100% of Eu-DTPA is eluted from CM-Sephadex column as expected for a negatively charged molecule. In contrast 100% of unchelated Eu$^{+3}$ is retained on the column as expected for a positive ion. These results demonstrate that the DTPA chelate of Eu$^{+3}$ forms within 5 minutes. These data show that the DTPA chelate of europium and the DTPA chelate of gadolinium have identical chromatographic behavior.

Example 20

Stability of Gd-DTPA

The stability of gadolinium-DTPA to autoclaving is demonstrated by properties of the pharmaceutical product known as Magnevist®.

Example 21

Stability of Sm-DTPA, La-DTPA, and Eu-DTPA to Autoclaving

A sample comprising 5 ml of Sm-DTPA, La-DTPA, and Eu-DTPA prepared in Examples 9, 10, and 11 were placed in 10 ml glass bottles, each capped with a grey butyl rubber cap, and the caps were crimped. Samples were autoclaved for 30 minutes at 121° C. Samples were allowed to cool to room temperature and were assayed as described in Examples 17, 18, and 19.

TABLE 11

Assay of autoclaved Sm-DTPA chelate, La-DTPA chelate, and Eu-DTPA chelate

Samarium-DTPA AUTOCLAVED

| Fraction # | Sample description | dpm | % of total |
|---|---|---|---|
| 1 | 5 ml of Sm-DTPA Example 9 was autoclaved, 0.1 ml was diluted 1:10 and applied to the CM-Sephadex column followed by 3 ml of 0.01M Tris buffer pH 7.5 | 1128928 | 98 |
| 2 | 3 ml of 0.01M Tris buffer pH 7.5 | 26387 | 2 |
| 3 | Column and contents | 1867 | 0 |

Lanthanum-DTPA AUTOCLAVED

| Fraction # | Sample description | dpm | % of total |
|---|---|---|---|
| 1 | 5 ml of La-DTPA from Example 10 was autoclaved, 0.1 ml was diluted 1:10 and applied to a CM-Sephadex | 411400 | 97 |

TABLE 11-continued

Assay of autoclaved Sm-DTPA chelate, La-DTPA chelate, and Eu-DTPA chelate

| | | dpm | % of total |
|---|---|---|---|
| | column followed by 3 ml of 0.01M Tris buffer pH 7.5 | | |
| 2 | 3 ml of 0.01M Tris buffer pH 7.5 | 12180 | 3 |
| 3 | Column and contents | 0 | 0 |

Europium-DTPA AUTOCLAVED

| Fraction # | Sample description | dpm | % of total |
|---|---|---|---|
| 1 | 5 ml of Eu-DTPA from Example 11 was autoclaved, 0.1 ml was diluted 1:10 and applied to a CM-Sephadex column followed by 2 ml of 0.01M Tris buffer pH 7.5 | 380954 | 97 |
| 2 | 3 ml of 0.01M Tris buffer pH 7.5 | 13226 | 3 |
| 3 | Column and contents | 0 | 0 |

Results: Table 11 shows that following autoclaving 100% of Sm-DTPA, 100% La-DTPA, and 100% Eu-DTPA was eluted from each of their respective CM-Sephadex columns, as is expected for a negatively charged chelate of the three respective lanthamides. In contrast 100% of unchelated Sm$^{+3}$, La$^{+3}$, and Eu$^{+3}$ is retained on the column as expected for a positive ion (Examples 9, 10, and 11). Thus no free Sm$^{+3}$, La$^{+3}$, or Eu$^{+3}$ is generated during autoclaving. These results demonstrate that the DTPA chelates of Sm$^{+3}$, La$^{+3}$, and Eu$^{+3}$ are stable to autoclaving. The DTPA chelate of samarium, lanthanum and europium and the DTPA chelate of gadolinium are all stable to the process of autoclaving. As autoclaving is a method of first choice for providing sterility, the stability of those chelates to autoclaving enables a rapid, large scale and economical method for sterilization.

Example 22

Stability of Sm-DTPA, La-DTPA, and Eu-DTPA in rat serum

To 0.45 ml of rat serum was added 50 μl of 1 mM Sm-DTPA, La-DTPA or Eu-DTPA. To 0.45 ml of rat serum was added 50 μl of 1 mM Sm, La or Eu chloride. The six respective solutions sat at room temperature for 24 hours. Samples from all six solutions were assayed as described in Examples 17, 18, and 19, except that 0.2 ml of sample was applied to column and samples were not diluted. Fractions were collected as indicated in Table 12. All fractions were dried at 70° C. for 76 hours, and 25 μl of arsenic internal standard was added. Samples were activated by exposure to a neutron flux in a 2 megawatt reactor for 15 minutes. After three days each sample was counted for 3 minutes.

Results: Table 12 shows that 100% of the DTPA chelates of Sm, La, and Eu elute from CM Sephadex columns while approximately 50% of their respective salts are bound to the column. The portion of unchelated salts eluting from the column was a result of the free metal ions binding to serum components. Based on the minimum number of dpms detectable, one can conclude that less than 2% of the chelated samples was dissociated from DTPA. We conclude that the DTPA chelates of Sm, La, and Eu are stable in rat seum.

TABLE 12

Stability of Sm-DTPA, La-DTPA, and Eu-DTPA in rat serum

Samarium-DTPA STABILITY IN RAT SERUM

| Fraction # | Sample description | dpm | % of total |
|---|---|---|---|
| 1 | Apply 0.2 ml of Sm-DTPA from sample incubated in rat serum, allow sample to drain into column followed by 2 ml of 0.01M Tris buffer pH 7.5 | 287916 | 96 |
| 2 | 3 ml of 0.01M Tris buffer pH 7.5 | 12133 | 4 |
| 3 | Column and contents | 0 | 0 |

Samarium chloride STABILITY IN RAT SERUM

| Fraction # | Sample description | dpm | % of total |
|---|---|---|---|
| 1 | Apply 0.2 ml of $SmCl_3$ from sample incubated in rat serum, allow sample to drain into column followed by 2 ml of 0.01M Tris buffer pH 7.5 | 104992 | 48 |
| 2 | 3 ml of 0.01M Tris buffer pH 7.5 | 5702 | 3 |
| 3 | Column and contents | 108299 | 49 |

Lanthanum-DTPA STABILITY IN RAT SERUM

| Fraction # | Sample description | dpm | % of total |
|---|---|---|---|
| 1 | Apply 0.2 ml of La-DTPA from sample incubated in rat serum, allow sample to drain into column followed by 2 ml of 0.01M Tris buffer pH 7.5 | 82912 | 93 |
| 2 | 3 ml of 0.01M Tris buffer pH 7.5 | 6167 | 7 |
| 3 | Column and contents | 0 | 0 |

Lanthanum chloride STABILITY IN RAT SERUM

| Fraction # | Sample description | dpm | % of total |
|---|---|---|---|
| 1 | Apply 0.2 ml of $LaCl_3$ from sample incubated in rat serum, allow sample to drain into column followed by 2 ml of 0.01M Tris buffer pH 7.5 | 51651 | 49 |
| 2 | 3 ml of 0.01M Tris buffer pH 7.5 | 6586 | 6 |
| 3 | Column and contents | 46450 | 44 |

Europium-DTPA STABILITY IN RAT SERUM

| Fraction # | Sample description | dpm | % of total |
|---|---|---|---|
| 1 | Apply 0.2 ml of Eu-DTPA from sample incubated in rat serum, allow sample to drain into column followed by 2 ml of 0.01M Tris buffer pH 7.5 | 4763 | 91 |
| 2 | 3 ml of 0.01M Tris buffer pH 7.5 | 499 | 9 |
| 3 | Column and contents | 0 | 0 |

Europium chloride STABILITY IN RAT SERUM

| Fraction # | Sample description | dpm | % of total |
|---|---|---|---|
| 1 | Apply 0.2 ml of $EuCll_3$ from sample incubated in rat serum, allow sample to drain into column followed by 2 ml of 0.01M Tris buffer pH 7.5 | 2378 | 42 |
| 2 | 3 ml of 0.01M Tris buffer pH 7.5 | 291 | 5 |
| 3 | Column and contents | 2940 | 52 |

Example 23

Effect of Dilution on the Stability of Sm-DTPA

Sm-DTPA (1 mM) was prepared as described in Example 9. The solution was further diluted with 0.01 M Tris buffer pH 7.51:10, 1:100, 1:1000, and 1:10000 and allowed to stand at room temperature for 24 hours. The four samples were then assayed for stability of the Sm-DTPA complex as described in Example 17. All samples were found to be stable, as shown in Table 13. Thus Sm-DTPA forms a stable complex within the concentration limits of 1 mM to 0.1 µM.

TABLE 13

Effect of dilution on the stability of Sm-DTPA

Samarium-DTPA, 1 mM

| Fraction # | Sample description | Dpm | % of total |
|---|---|---|---|
| 1 | 3 ml of 0.01M Tris buffer pH 7.5 | 0 | 0 |
| 2 | 1 ml of Sm-DTPA from Example 9 diluted 1:10 followed by 3 ml of 0.01M Tris buffer pH 7.5 | 1482087 | 97 |
| 3 | 3 ml of 0.01M Tris buffer pH 7.5 | 19089 | 1 |
| 4 | Column and contents | 24257 | 2 |

Samarium-DTPA, 100 uM

| Fraction # | Sample description | Dpm | % of total |
|---|---|---|---|
| 1 | 3 ml of 0.01M Tris buffer pH 7.5 | 0 | 0 |
| 2 | 1 ml of Sm-DTPA (100 uM) diluted 1:10 followed by 3 ml of 0.01M Tris buffer pH 7.5 | 162208 | 98 |
| 3 | 3 ml of 0.01M Tris buffer pH 7.5 | 1308 | <1 |
| 4 | Column and contents | 2121 | 2 |

Samarium-DTPA, 10 µM

| Fraction # | Sample description | Dpm | % of total |
|---|---|---|---|
| 1 | 3 ml of 0.01M Tris buffer pH 7.5 | 0 | 0 |
| 2 | 1 ml of diluted Sm-DTPA (10 µM) diluted 1:10 followed by 3 ml of 0.01M Tris buffer pH 7.5 | 15685 | 100 |
| 3 | 3 ml of 0.01M Tris buffer pH 7.5 | 19 | <1 |
| 4 | Column and contents | 0 | 0 |

Samarium-DTPA, 1 µM

| Fraction # | Sample description | Dpm | % of total |
|---|---|---|---|
| 1 | 3 ml of 0.01M Tris buffer pH 7.5 | 0 | 0 |
| 2 | 1 ml of diluted $SmCl_3$ plus DTPA (1 µM) diluted 1:10 followed by 3 ml of 0.01M Tris buffer pH 7.5 | 1386 | 96 |
| 3 | 3 ml of 0.01M Tris buffer pH 7.5 | 29 | 2 |
| 4 | Column and contents | 21 | 2 |

Samarium-DTPA, 0.1 µM

| Fraction # | Sample description | Dpm | % of total |
|---|---|---|---|
| 1 | 3 ml of 0.01M Tris buffer pH 7.5 | 0 | 0 |
| 2 | 1 ml of diluted Sm-DTPA (0.1 µM) diluted 1:10 followed by 3 ml of 0.01M Tris buffer pH 7.5 | 192 | 99 |
| 3 | 3 ml of 0.01M Tris buffer pH 7.5 | 1 | 1 |
| 4 | Column and contents | 0 | 0 |

Results: Table 13 shows that 100% of the DTPA chelate of Sm elutes from CM Sephadex columns within a concentration range of 0.1 µM to 1 mM, indicating that the DTPA chelate of Sm is stable within this concentration range.

Example 24

Assay of Gd-DOTA

Preparation of carboxymethyl sephadex column. To a 10 ml plastic pipet cut off at the 3 ml mark and plugged with glass wool at the bottom, add enough slurry to form a 2 ml volume of the CM sephadex. Wash the packed resin with 6 ml of 1 M Tris buffer pH 7.5, and 6 ml of 0.01M Tris buffer pH 7.5. Dilute sample (Gadolinium-DOTA from Example 12) 1:10 with distilled water (0.2 ml to 2 ml). Apply fractions as follows. Fraction 1. One ml of sample A and allow to drain into column. Apply 3 ml of 0.01 M Tris buffer pH 7.5 and allow to drain into column. Fraction 2. Three ml of 0.01M Tris buffer pH 7.5 and allow to drain into column. Collect the eluant of fractions 1 and 2. Dry all fractions at 70° C. for 76 hours, dissolve in 1 ml of 1 mM HCl and assay by atomic absorption for Gadolinium.

TABLE 14

Assay of Gd-DOTA

Gadolinium-DOTA from Example 12

| Fraction # | Sample description | Gd umol | % of total |
|---|---|---|---|
| 1 | 1 ml of diluted GdCl$_3$ plus DOTA from Example 12 diluted 1:10 followed by 3 ml of 0.01M Tris buffer pH 7.5 | 0.1 | 100 |
| 2 | 3 ml of 0.01M Tris buffer pH 7.5 | 0 | 0 |

Results: Table 14 shows that 100% of Gd-DOTA is eluted from CM-Sephadex column as expected for a negatively charged molecule. In contrast 100% of unchelated Gd$^{+3}$ is retained on the column as expected for a positive ion (see Example 16). These results demonstrate that the DOTA chelate of Gd$^{+3}$ forms within 5 minutes, and that this method can be used to ascertain the formation of metal DOTA chelates.

Example 25

Assay of Sm-DOTA, La-DOTA, and Eu-DOTA

Preparation of carboxymethyl sephadex column. To a 10 ml plastic pipet cut off at the 3 ml mark and plugged with glass wool at the bottom, enough slurry was added to form a 2 ml volume of the CM sephadex. The packed resin was washed with 6 ml of 1 M Tris buffer pH 7.5, and 6 ml of 0.01M Tris buffer pH 7.5. Samples from Examples 13, 14, and 15 were diluted 1:10 with distilled water (0.2 ml to 2 ml). Fractions were applied as follows. Fraction 1. One ml of sample (Sm-DOTA, La-DOTA, and Eu-DOTA) to individual CM-sephadex columns and allow to drain into column. Apply 3 ml of 0.01 M Tris buffer pH 7.5 and allow to drain into column. Fraction 2. Three ml of 0.01M Tris buffer pH 7.5 and allow to drain into column. Collect the eluant of Fractions 1 and 2. Fraction 3. Column and contents. Fractions were dried at 70° C. for 76 hours and 25 μl of arsenic internal standard was added. Samples were activated by exposure to a neutron flux in a 2 megawatt reactor for 15 minutes. After three days each sample was counted for 3 minutes.

TABLE 15

Assay of Sm-DOTA, La-DOTA, and Eu-DOTA

Samarium chloride and DOTA from Example 13

| Fraction # | Sample description | dpm | % of total |
|---|---|---|---|
| 1 | 1 ml of diluted Sm-DOTA from Example 13 diluted 1:10 followed by 3 ml of 0.01M Tris buffer pH 7.5 | 1429326 | 98 |
| 2 | 3 ml of 0.01M Tris buffer pH 7.5 | 28850 | 2 |
| 3 | Column and contents | 0 | 0 |

Lanthanum-DOTA from Example 14

| Fraction # | Sample description | dpm | % of total |
|---|---|---|---|

TABLE 15-continued

Assay of Sm-DOTA, La-DOTA, and Eu-DOTA

| 1 | 1 ml of diluted Sm-DOTA from Example 14 diluted 1:10 followed by 3 ml of 0.01M Tris buffer pH 7.5 | 410040 | 97 |
|---|---|---|---|
| 2 | 3 ml of 0.01M Tris buffer pH 7.5 | 11681 | 3 |
| 3 | Column and contents | 0 | 0 |

Europium-DOTA from Example 15

| Fraction # | Sample description | Dpm | % of total |
|---|---|---|---|
| 1 | 1 ml of diluted Sm-DOTA from Example 15 diluted 1:10 followed by 3 ml of 0.01M Tris buffer pH 7.5 | 391454 | 100 |
| 2 | 3 ml of 0.01M Tris buffer pH 7.5 | 132 | <1 |
| 3 | Column and contents | 0 | 0 |

Results: Table 15 shows that 100% of Sm-DOTA, La-DOTA, or Eu-DOTA is eluted from CM-Sephadex columns A, B, and C, respectively, as expected for a negatively charged molecule. In contrast, 100% of unchelated Sm$^{+3}$, La$^{+3}$, and Eu$^{+3}$ is retained on their corresponding columns (cf Examples 11, 12, and 13) as expected for a positive ion. These results demonstrate that the DOTA chelates of Sm$^{+3}$, La$^{+3}$, and Eu$^{+3}$ forms within 5 minutes, and that this method can be used to ascertain the formation of metal DOTA chelates. The DOTA chelate of samarium, lanthanum, and europium and the DOTA chelate of gadolinium have identical chromatographic behavior.

Example 26

Stability of Gd-DOTA

Gadolinium-DOTA is stable to autoclaving as demonstrated by properties of the pharmaceutical product known as DOTAREM®.

Example 27

Stability of Sm-DOTA, La-DOTA, and EU-DOTA to Autoclaving

Five ml of each of Sm-DOTA, La-DOTA, and Eu-DOTA prepared in Examples 13, 14, and 15 were placed in 10 ml glass bottles capped with a grey butyl rubber cap and crimped. Samples were autoclaved for 30 minutes at 121° C. Samples were allowed to cool to room temperature and were assayed as described in Examples 25.

TABLE 16

Stability of Sm-DOTA, La-DOTA, and Eu-DOTA to autoclaving

Samarium-DOTA AUTOCLAVED

| Fraction # | Sample description | dpm | % of total |
|---|---|---|---|
| 1 | 5 ml of Sm-DOTA Example 13 was autoclaved, 0.1 ml was diluted 1:10 and applied to the CM-Sephadex column followed by 2 ml of 0.01M Tris buffer pH 7.5 | 1439622 | 98 |
| 2 | 3 ml of 0.01M Tris buffer pH 7.5 | 27521 | 2 |
| 3 | Column and contents | 0 | 0 |

Lanthanum-DOTA AUTOCLAVED      dpm      % of total

TABLE 16-continued

Stability of Sm-DOTA, La-DOTA, and Eu-DOTA to autoclaving

| | | | |
|---|---|---|---|
| 1 | 5 ml of La-DOTA from Example 14 was autoclaved, 0.1 ml was diluted 1:10 and applied to a CM-Sephadex column followed by 2 ml of 0.01M Tris buffer pH 7.5 | 400045 | 100 |
| 2 | 3 ml of 0.01M Tris buffer pH 7.5 | 11 | <1 |
| 3 | Column and contents | 0 | 0 |

| Europium-DOTA AUTOCLAVED | dpm | % of total |
|---|---|---|
| 1  5 ml of Eu-DOTA from Example 15 was autoclaved, 0.1 ml was diluted 1:10 and applied to a CM-Sephadex column followed by 2 ml of 0.01M Tris buffer pH 7.5 | 366651 | 100 |
| 2  3 ml of 0.01M Tris buffer pH 7.5 | 1226 | <1 |
| 3  Column and contents | 0 | 0 |

Results: Table 16 shows that following autoclaving, 100% of Sm-DOTA leads to an unstable product producing a mixture of Sm-DOTA and unchelated $Sm^{+3}$. However, 100% of La-DOTA, and Eu-DOTA is eluted from their respective CM-Sephadex columns as expected for a negatively charged molecule. In contrast 100% of unchelated $Sm^{+3}$, $La^{+3}$, and $Eu^{+3}$ is retailed on their corresponding columns (cf Examples 11, 12, and 13) as expected for a positive ion. These results demonstrate that the DOTA chelate of $La^{+3}$, and $Eu^{+3}$ are stable to autoclaving. The DOTA chelates of each of lanthanum, europium, and gadolinium are stable to autoclaving.

Example 28

Formation and Assay of Chelates Using Enriched Stable Isotope Metals

Chelates of DTPA and DOTA are formed as described in Examples 9–11 (for DTPA chelates) and 13–15 (for DOTA chelates), except that enriched isotope preparations of the respective chloride salts of each element are used. Chelate formation is assayed as described in Examples 17–19 for (DTPA chelates) and 25 (for DOTA chelates). Results obtained with natural abundance isotopes and enriched isotopes are identical within experimental error. Table 17 illustrates the gain in sensitivity obtained using enriched stable isotopes over natural abundance isotopes.

TABLE 17

Comparison of potency of natural abundance and enriched stable isotope preparations in neutron activation analysis. Enriched isotopes preparations were obtained from the Department of Energy.

| | | Abundance | | Fold increase |
|---|---|---|---|---|
| Element | Isotope | Natural | Enriched | in potency |
| Lanthanum | La-139 | 99.1 | 99.99 | 1.01 |
| Samarium | Sm-149 | 13.8 | 97.68 | 7.08 |
|  | Sm-152 | 26.7 | 99.44 | 3.72 |
| Europium | Eu-151 | 47.8 | 96.81 | 2.03 |
|  | Eu-153 | 53.2 | 98.79 | 1.86 |

Example 29

Kinetics of Blood Depletion and Urine Accumulation of Sm-DTPA in the Rat

One half ml of Sm-DTPA (0.01 mg/kg), dissolved in saline (pH 7), is injected into the tail vein of three rats. Samples of blood are obtained at 10, 30 and 60 minutes following injection and analyzed for Sm-DTPA by neutron activation. The percent of starting amount of the Sm-DTPA at each time interval is presented in Table 18 (last column on right). Similarly, the accumulation of Sm-DTPA in the rat urine at two times is shown in the last column of Table 18. Results: Table 18 show that the elimination of Sm-DTPA from rat blood and its accumulation in rat urine is independent of the presence of other chelated metals when present in low quantities (compare columns 4 and 5).

Example 30

Kinetics of Blood Depletion and Urine Accumulation of Tc-DTPA, Gd-DTPA and Sm-DTPA in the Rat One half ml of Technetium-99m-DTPA (1 millicurie), Gd-DTPA (0.05 mg/kg), and Sm-DTPA (0.01 mg/kg) are each dissolved in saline (pH 7), and are injected simultaneously into the tail vein of three rats. Samples of blood are obtained at 10, 30 and 60 minutes following injection and analyzed for $^{99m}$Tc-DTPA (gamma counting), Gd-DTPA (T1 relaxation) and Sm-DTPA (neutron activation). The percent of starting amounts of each of the three compounds at each time interval presented in Table 18 shows that each of these compounds exits the rats blood at identical rates within experimental error. The accumulation of the three compounds in the rat urine at two times also shows an identical pattern among the three compounds. Table 18 shows that Sm-DTPA exhibits identical biological properties with Gd-DTPA and $^{99m}$Tc-DTPA in the rat demonstrating its equivalence to two previously accepted compounds used for measuring glomerular filtration rate (GFR).

TABLE 18

Kinetics of blood depletion and urine accumulation of Tc-DTPA, Gd-DTPA and Sm-DTPA in the rat. Values shown in bold are obtained when $^{99m}$Tc-DTPA, Gd-DTPA and Sm-DTPA are injected simultaneously (Example 30). The values shown on the column 5 is obtained using only Sm-DTPA (Example 29). Values represent the average of three animals.

| | Percent of initial injection | | | |
|---|---|---|---|---|
| Time after | simultaneously administered | | | administered alone |
| injection, min | $^{99m}$Tc-DTPA | Gd-DTPA | Sm-DTPA | Sm-DTPA |
| Blood | | | | |
| 10 | 85 | 83 | 88 | 86 |
| 30 | 63 | 65 | 60 | 61 |
| 60 | 30 | 35 | 33 | 28 |
| Urine | | | | |
| 30 | 25 | 22 | 26 | 24 |
| 180 | 92 | 94 | 90 | 91 |

Example 31

Kinetics of Blood Depletion and Urine Accumulation of Sm-DTPA, La-DTPA and Eu-DTPA in the Rat Upon Simultaneous Administration. Independent and Identical Excretion of Stable Isotope Labeled Chelates Sm-DTPA, La-DTPA, and Eu-DTPA One half ml of Sm-DTPA, La-DTPA and Eu-DTPA (each 0.01 mg/kg), dissolved in saline (pH 7) are injected simultaneously into the tail vein of three rats. Samples of blood are obtained at 10, 30 and 60 minutes following injection and analyzed for each element by neutron activation. The percent of starting amounts of each of the three compounds at each time interval, presented in Table 19, shows that each of these compounds exits the rat's blood at identical rates, within experimental error. The accumulation of the three compounds in the rat urine at two times also shows an identical pattern among the three compounds. Table 19 shows that Sm-DTPA, La-DTPA and Eu-DTPA when administered simultaneously are eliminated independently of the other two chelates.

TABLE 19

Values shown in bold are obtained when Sm-DTPA, La-DTPA and Eu-DTPA are injected simultaneously (Example 31). The values shown on the right column is obtained using only Sm-DTPA (Example 29). Values represent the average of three animals.

| Time after injection, min | Percent of initial injection | | | |
|---|---|---|---|---|
| | simultaneously administered | | | administered alone |
| | Sm-DTPA | La-DTPA | Eu-DTPA | Sm-DTPA |
| Blood | | | | |
| 10 | 83 | 85 | 87 | 86 |
| 30 | 61 | 63 | 62 | 61 |
| 60 | 34 | 33 | 33 | 28 |
| Urine | | | | |
| 30 | 22 | 23 | 21 | 24 |
| 180 | 90 | 92 | 96 | 91 |

Example 32

Kinetics of Blood Depletion and Urine Accumulation of Sm-DTPA, La-DTPA and Eu-DTPA in Rat Following Sequential Administration of Each Chelate: Independent Excretion of Sequential Administrations of Stable Isotope Labeled Chelates Sm-DTPA, La-Eu-DTPA, and Eu-DTPA Samples of Sm-DTPA, La-DTPA and Eu-DTPA (0.5 ml; 0.01 mg/kg), each dissolved in saline (pH 7), are injected sequentially at 0, 20, and 40 minutes into the tail vein of three rats. Samples of blood are obtained at 10, 30 and 60 min following each injection and analyzed for each element by neutron activation. The percent of starting amounts of each of the three compounds at each time interval presented in Table 20 shows that each compound exits the rat's blood at identical rates within experimental error. The accumulation of the three compounds in rat urine at two times shows an identical pattern among the three compounds. Table 20 shows that Sm-DTPA, La-DTPA and Eu-DTPA administered sequentially are each eliminated independently of the other chelates, and that each chelate can be measured in the presence of the other chelates without interference.

TABLE 20

Values shown in bold are obtained when Sm-DTPA, La-DTPA and Eu-DTPA are injected sequentially (Example 32). The values shown on the right column are obtained using only Sm-DTPA (Example 32). Values represent the average of three animals.

| Time after injection, min | Percent of initial injection | | | |
|---|---|---|---|---|
| | sequentially administered | | | administered alone |
| | Sm-DTPA | La-DTPA | Eu-DTPA | Sm-DTPA |
| Blood | | | | |
| 10 | 81 | 82 | 87 | 86 |
| 30 | 59 | 62 | 64 | 61 |
| 60 | 29 | 32 | 34 | 28 |
| Urine | | | | |
| 30 | 20 | 25 | 26 | 24 |
| 180 | 89 | 95 | 97 | 91 |

Example 33

Kinetics of Blood Depletion of Gd-DTPA in the Rat Following Three Sequential Administrations of the Chelate. Lack of Independence of Sequential Administrations of Gd-DPTA In this theoretical example, three 0.5 ml samples of Gd-DTPA (0.05 mg/kg) each dissolved in saline (pH 7) are injected sequentially at 0, 20, and 40 minutes into the tail vein of a rat. Samples of blood are obtained at 10, 30 and 60 minutes following each injection and analyzed for Gd by T1 relaxation. The percent of starting amount of the first injection of Gd at each time interval presented in Table 21 shows that Gd exits the rat's blood in a complicated pattern that does not allow the calculation of its rate of elimination. This example highlights one advantage of using neutron activation over T1 relaxivity to measure pharmacological rates of elimination when using sequential injections (compare Examples 32 and 33).

TABLE 21

Values represent time of injection and percent of initial value of Gd following the first injection, the second injection, and the third injection. The cumulative total value of Gd is calculated based upon the first injection. Values represent the average of three animals.

| Time after injection, of sample min | | | Percent of initial injection | | | |
|---|---|---|---|---|---|---|
| | | | First injection | Second injection | Third injection | Cumulative total |
| 1st | 2nd | 3rd | Gd-DTPA | Gd-DTPA | Gd-DTPA | Gd-DTPA |
| 0 | | | 100 | | | 100 |
| 10 | | | 81 | | | 81 |
| 20 | 0 | | 73 | 100 | | 173 |
| 30 | 10 | | 59 | 81 | | 140 |
| 40 | 20 | 0 | 47 | 73 | 100 | 220 |
| 50 | 30 | 10 | 35 | 59 | 81 | 175 |
| 60 | 40 | 20 | 29 | 47 | 73 | 149 |
| 70 | 50 | 30 | 26 | 35 | 59 | 120 |
| 80 | 60 | 40 | 22 | 26 | 47 | 95 |
| 90 | 70 | 50 | | | | |
| 100 | 80 | 60 | 18 | 22 | 35 | 75 |

Example 34

Comparison of Sensitivity of Gd as Measured by NMR Spectroscopy, with Sm as Measured by Neutron Activation Standards of Gd-DTPA were prepared in phosphate buffered saline (pH 7.4) to the concentrations indicated in Table 22. One ml samples of the standards at each concentration were inserted into the bore of a Brucker PC120 minispectrophotometer, and the T1 relaxation was determined according to the manufacturers instructions. A plot of pre-determined Gd-DTPA concentration as a function of experimentally measured mass shows that a strong linear relationship was obtained (Table 22). A sensitivity (limit of detection) of between 1 and 10 µM Gd was determined.

To illustrate the linear range of detection of neutron activation, the following sensitivity study was undertaken using two stable-labels: samarium and lanthanum. Atomic absorption standard solutions of each element were purchased (Sigma, St. Louis, Mo.). From these standard solutions, test samples were produced which contained 0.02 µg to 50 µg of each element. Each sample was placed in a vial containing 0.1 g of bovine liver tissue, 1 ml human blood, or 5 ml human urine. A metallic monitor was added to each vial to account for neutron flux density variations during activation analysis. Samples were dried at 70° C. to remove water. All vials were irradiated for 10-minutes at a power level of one megawatt, which generated an average neutron flux density of $2 \times 10^{17}$ $m^{-2}$ $s^{-2}$. Activated vials were stored for 24-hours to allow short-lived activation productions to decay. Spectrographic analysis was then performed to measure the concentration of the resultant radioactive nuclei in each vial.

The results show a strong linear relationship when pre-determined samarium and lanthanum masses were plotted as a Function of experimentally measured masses (Table 23). Neutron activation analysis accurately assessed trace quantities of both isotopes to levels as low as 0.02 µg (0.1 mmol) with a high degree of precision. The corresponding detectable concentrations of stable isotope in liver, blood and urine were 1 µM, 0.1 µM, and 0.02 µM, respectively. Additional sensitivity may be obtained by use of increased irradiation time and use of higher neutron flux field.

Therefore, this comparative study shows that stable isotope labeling combined with neutron activation can measure small concentrations of stable labels to levels as low as 20 nM, which is a factor of 50 to 500 fold more sensitive then NMR detection of Gd-DTPA. The results with neutron activation also demonstrate that measurement results are obtained independent of the presence of different type of biological tissue.

TABLE 22

| Concentrations of Gd-DTPA standards. | | | | | | |
|---|---|---|---|---|---|---|
| Detection of Gd-DTPA by NMR in PBS | | | Detection of Sm-DTPA by neutron activation | | Detection of La-DTPA by neutron activation | |
| Concentration (µM) | T1 | 1/T1 | Concentration (µM) | Dpm | Concentration (µM) | dpm |
| 0 | 3.810 | 262.502 | 0 | 0 | 0 | 0 |
| 1 | 3.819 | 261.835 | 0.01 | 123 | 0.01 | 52 |
| 10 | 3.314 | 301.714 | 0.1 | 1398 | 0.1 | 537 |

TABLE 22-continued

Concentrations of Gd-DTPA standards.

| Detection of Gd-DTPA by NMR in PBS | | | Detection of Sm-DTPA by neutron activation | | Detection of La-DTPA by neutron activation | |
|---|---|---|---|---|---|---|
| Concentration (µM) | T1 | 1/T1 | Concentration (µM) | Dpm | Concentration (µM) | dpm |
| 25 | 2.483 | 402.739 | 1 | 10987 | 1 | 5143 |
| 50 | 2.053 | 487.211 | 10 | 123584 | 10 | 52879 |

TABLE 23

Linear regression analysis of data from Table 23.

| Samarium | y = 0.02 + 1.00x | r = 1.0 |
| Lanthanum | y = 0.03 + 0.92x | r = 0.98 |
| Gadolinium | Y = 4.69x + 262.53 | r = 0.99 |

Example 35

Effect of Matrix on the Determination of Sm-DTPA by Neutron Activation

One µg of Sm (as Sm-DTPA) was pipetted into sample tubes prelabeled with monitor. The sample tubes contained either 1 g of beef liver, 1 ml of human blood or 1 ml of human urine. All samples were dried at 70° C. for 76 hours, and 25 µl of arsenic internal standard was added to each sample. Samples were activated by exposure to a neutron flux in a 1 megawatt reactor for 15 minutes. After three days samples, were counted for 3 minutes. The results of the three samples are shown in Table 24, and indicate that neutron activation analysis of stable isotopes is independent of the matrix.

TABLE 24

Effect of matrix on the determination of Sm-DTPA by neutron activation

| Sample | Sm | Dpm |
|---|---|---|
| 1 g liver | 1 µg | 712353 |
| 1 ml blood | 1 µg | 705228 |
| 1 ml urine | 1 µg | 722241 |

Example 36

The use of Iohexol, a Stable Isotope Labeled Iodinated Compound, and Neutron Activation to Measure GFR in a Rabbit One New Zealand White male rabbit (m=2 kg) was sedated with intramuscular ketanine (35 mg/kg) and xylazine (5 mg/kg). Both the right and left ear veins were catheterized. One line was used to inject Iohexol (Omnipaque®, Nycomed, Inc., Princeton, N.J.). The injected dose (ID) was 90 mg of iodine. After the injection, the second line was used to collect blood samples at the following time points −5, 10, 15, 20, 30, 45, 60, 96, 120, 180 minutes. For each blood sample, 100 µl of serum was placed in a clean sample vial. A metallic monitor was than added to each vial to account for potential neutron flux density variations during neutron activation analysis. Neutron activation was performed in a 2 megawatt reactor for 1 min and samples were counted within 30 minutes following activation. Counts were converted into disintegrations per minute and the measured iodine concentration for each sample was plotted as a function of time of sample withdrawal. The data was fit to a two compartment exponential model using the equation: Plasma concentration=$Ae^{-(at)}+Be^{-(bt)}$. The area under the curve (AUC) from t=0 to t=180 minutes was calculated from the fit. The GFR (ml/kg/min) was than calculated as follows:

$$GFR=(ID/AUC)/m,$$

where: ID=initial dose of iohexol, AUC=(A/a+B/b), and m=minutes.

Iohexol is found to be removed from the blood as a smooth function of time (Table 25). The calculated parameters used to fit the data were for a two compartment model. The measured GFR value was 4.8, which is comparable to reported values for normal rabbits.(57–59)

| | | Iohexal | |
|---|---|---|---|
| Number | Time | dpm/ul | mg/ml |
| 1 | 180 | 605.5 | 0.01458 |
| 2 | 120 | 982.0 | 0.02365 |
| 3 | 96 | 1317.8 | 0.03174 |
| 4 | 60 | 2032.3 | 0.04894 |
| 5 | 45 | 1952.3 | 0.04702 |
| 6 | 30 | 2810.5 | 0.06769 |
| 7 | 20 | 3689.4 | 0.08885 |
| 8 | 15 | 3595.7 | 0.08660 |
| 9 | 10 | 4541.7 | 0.10938 |
| 10 | 5 | 5166.1 | 0.12442 |

Example 37

Results of a Hypothetical Study in Humans Comparing GFR Results Obtained Using Sm-DTPA (Determined by Neutron Activation) with Two Other Methods ($^{99m}$Tc-DTPA and Gd-DTPA.

Preparatory Procedures

Thirty-five patients afflicted with renal dysfunction are evaluated at the National Institutes of Health (N.I.H.) under an Institutional Review Board-Approved protocol. The following procedure is followed for all patients in the study.

The evening before the study, the patients are given a low salt, low protein diet. On the morning of the study, intravenous (i.v.) hydration is started through an i.v. line placed in the arm of each patient until an adequate urinary output was established. An initial loading dose is given of oral fluid supplemented by 5% wt dextrose in water intravenous fluid to equal approximately 20 ml/kg of body weight. The hydration is continued by the i.v. administration of 5% wt dextrose in water (Mcgaw-Kendall Co., Irvine, Calif.)

supplemented by oral hydration for approximately 3–4 hours at 300–400 ml/hour. A separate intravenous line for blood drawing is inserted in the arm of the patient and then each patient is transported to the Nuclear Medicine Department. Intravenous hydration, supplemented by oral hydration when needed, is continued for the duration of the study. Preliminary blood (S1, 10 ml) and urine (U1, 10 ml) samples are obtained prior to applying any further treatment.

Procedure for Obtaining Blood and Urine Samples

One millicurie technetium-99m-DTPA, 0.05 mg/kg Gd-DTPA, and 0.01 mg/kg Sm DTPA are simultaneously injected i.v. to each patient through the hydration line. A second blood sample (S2, 6 ml) is obtained from each patient after one hour of "equilibrium time." The equilibrium time is the time in which the compounds reach equilibrium between intra- and extra-vascular spaces. Samples of blood and urine are obtained for each of the of the three methods of measurement (gamma counting, $^{99m}$Tc; MR relaxation, Gd; and neutron activation, Sm) at each time point. This set of samples is collectively referred to as blood and urine samples in the following description.

The patient is then encouraged to void. When the patient is next able to void, usually within 20–25 minutes, a third blood sample (S3, 6 ml) and a second urine sample (U2, 10 ml) are obtained for each patient. The volume and time of the interval since the last voiding event is noted.

Each patient is then allowed to rest for another "interval," after which the patient is again encouraged to void and a fourth blood sample (S4, 6 ml) and a third urine sample (U3, 10 ml) are obtained. The volumes and times are recorded, as well.

This process is repeated once again to obtain fifth blood and fourth urine samples (S5, 6 ml and U4, 10 ml). The volume:time ratios or urine rates for the different points obtained are then compared.

If the volume:time ratios or urine rates for the three intervals are comparable, these values are utilized for the calculations and no more data are obtained for the patient. If, however, the volume:time ratios or urine rates are found to differ, further measurements were taken for the patient at additional intervals until at least three comparable volume:time ratios or urine rates are obtained. After the procedure is completed, the intravenous lines are removed and the patient remains free to move around.

Scintillation Counting of Samples

The technetium-99m-DTPA labeled samples are counted in a scintillation counter as is known in the art. A Technetium-DTPA clearance rate is calculated from these data in accordance with standard methods known in the art (Licottke, R. R. and Duarte, C. G., "Lab. Protocol and Meth. Meas. Glomer. Filter Rate and Renal Plasma Flow", in Renal Function Tests: Clinical Lab. Proc. and Diag., Duarte C. G., Ed., Little Brown, Boston, pp. 290–63 (1980)).

Relaxation Measurements of Gd

The Gd-DTPA labeled blood samples are centrifuged to separate serum and blood products. They are left in a refrigerator overnight to eliminate the radioactivity present in the blood due to the presence of $^{99m}$Tc-DTPA. The half-life of Technetium is about 6 hours and thus it has almost completely decayed in 24 hours.

Serum and urine samples are then measured using a Praxis 10 MHz spectrometer with a 90-tau-90 pulse sequence as described by Farrar et al (Farrar et al, in Pulse and Fourier Transform NMR. Intro. Theory and Meth., pp. 18–33, Academic Press, N.Y. (1971)).

Values are obtained at 30 points for tau and then are plotted as an exponential curve versus time. The method relies on an approximate estimation of the actual T1 value of the substance in the sample being measured. Two T1 values are determined for each sample.

The preliminary or pre-injection blood and urine samples are then "doped" (i.e., given an internal standard) with pre-measured aliquots of a specified volume of known Gd concentration. Pre-injection "standards" are thus produced for the urine and serum samples and their T1s are then measured in the manner described above. The data for the different samples are then recorded on data sheets as shown below.

Data recording sheet for patients in GFR study

Data Recording Sheet for Each Patent

| Name | Time | Content | Value |
|------|------|---------|-------|
| S1 | pre | preliminary blood sample | |
| SS1 | pre | blood STD 1 + Gd-DTPA | |
| SS2 | pre | blood STD 2 + Gd-DTPA | |
| S2 | post | blood start Interval 1 | |
| S3 | post | blood end interval 1 | |
| S4 | post | blood end interval 2 | |
| S5 | post | blood end interval 3 | |
| S6 | post | blood end interval 4 | |
| U1 | pre | preliminary urine sample | |
| US1 | pre | urine STD 1 + Gd-DTPA | |
| US2 | pre | urine STD 2 + Gd-DTPA | |
| U2 | post | urine end interval 1 | |
| U3 | post | urine end interval 2 | |
| U4 | post | urine end interval 3 | |
| U5 | post | urine end interval 4 | |

STD: Standard
Points S6 and U5 are taken only when desired or necessary.

Neutron Activation of Sm

Whole blood and urine samples are added to preweighted vials containing monitor to correct for neutron flux, and are mailed to the user's facility for neutron activation. The weight of each sample is determined at the facility. Samples are activated by exposure to a neutron flux in a 5 megawatt reactor for 15 minutes. After one day of storage, samples are counted for 3 minutes. Samarium concentrations in each sample are determined using a standard curve developed with NIST traceable Sm.

Computation of Results

Computational methods of the results for $^{99m}$Tc-DTPA and Gd-DTPA, and calculation of GFR are as described in U.S. Pat. No. 5,100,646.

The results (Table 26) show that the method herein, using stable isotope labeled chelates, both correlates and agrees with established methods for determining GFR (R=0.95; $^{99m}$Tc-DTPA vs Sm-DTPA. R=0.99; Gd-DTPA vs Sm-DTPA).

TABLE 26

Results of a hypothetical study in humans comparing GFR results obtained using Sm-DTPA (determined by neutron activation) with two other methods ($^{99m}$Tc-DTPA and Gd-DTPA).

| PATIENT # | Tc GFR | Gd GFR | Sm GFR |
|-----------|--------|--------|--------|
| 1 | 57.6 | 54.5 | 55.8 |
| 2 | 15.4 | 15.4 | 16.3 |
| 3 | 93.4 | 99.5 | 103.7 |
| 4 | 86 | 106 | 110 |
| 5 | 57.3 | 54.6 | 58.6 |
| 6 | 83.2 | 83.2 | 82.9 |
| 7 | 139 | 158 | 161 |
| 8 | 100 | 112 | 108 |
| 9 | 58.9 | 54.4 | 52.4 |

TABLE 26-continued

Results of a hypothetical study in humans comparing GFR results obtained using Sm-DTPA (determined by neutron activation) with two other methods ($^{99m}$Tc-DTPA and Gd-DTPA).

| PATIENT # | Tc GFR | Gd GFR | Sm GFR |
|---|---|---|---|
| 10 | 65.2 | 71.6 | 70.5 |
| 11 | 83.8 | 77 | 79.4 |
| 12 | 97.1 | 97.2 | 98.0 |
| 13 | 88.4 | 74.6 | 82.7 |
| 14 | 83 | 89 | 86 |
| 15 | 87 | 80.3 | 77.1 |
| 16 | 79.3 | 76.6 | 77.8 |
| 17 | 93.2 | 99 | 103 |
| 18 | 82.8 | 93.7 | 98.4 |
| 19 | 60 | 65.6 | 62.4 |
| 20 | 83.2 | 86.8 | 88.9 |
| 21 | 54 | 58.9 | 60.4 |
| 22 | 74.5 | 72.3 | 73 |
| 23 | 101 | 110 | 112 |
| 24 | 57.5 | 59 | 59 |
| 25 | 100.4 | 99.2 | 97 |
| 26 | 82.1 | 81.3 | 82 |
| 27 | 65.7 | 63 | 64 |
| 28 | 72.4 | 72.2 | 72 |
| 29 | 100 | 109.7 | 110 |
| 30 | 78.3 | 84.5 | 86.3 |
| 31 | 89.6 | 92.7 | 91.5 |
| 32 | 77 | 82.2 | 79.1 |
| 33 | 51.8 | 52.3 | 52.0 |
| 34 | 93.5 | 102.6 | 104 |
| 35 | 58.8 | 58.5 | 58 |

The values with the $^{99m}$Tc-DTPA clearance test and the Gd-DTPA clearance test show a good correlation (R=0.96). These data represent the summation of the GFRs obtained with the Sm-DTPA clearance method of the invention for 10 patients who received 0.1 mmole/kg wt Sm-DTPA and for 30 patients who received 0.01 mmole/kg wt.

The dose of Sm-DTPA administered to the patient does not significantly alter the accuracy of the results. In view of this information, establishing the dose to be no greater than the lower dose of Sm-DTPA is preferred for further applications.

The invention regarding the use of stable isotope labeled substances for use in determining GFR now being fully described, it will be apparent to one of ordinary skill in the art that many changes and modifications can be made thereto without departing from the spirit or scope of the invention as set forth herein.

Example 38

Synthesis of Ficoll (MW 70 kDa) Carboxymethyl$_{10}$. (Carboxymethyl Ficoll 70)

Ficoll of molecular weight 70 kDa (0.75 g), and sodium hydroxide (1.15 g) dissolved in 7.2 ml of deionized water, were combined with 0.55 g of bromoacetic acid dissolved in 1.425 ml deionized water. The solution was stirred for 2 hours at 25° C., neutralized to pH 7 with 6 N hydrochloric acid, and dialyzed against Spectropor 2 (MWCO 12,000) membrane with deionized water. The retained material was lyophilized. The conjugate contained 10 mmoles of carboxymethyl group per gram of product as determined by titration with sodium hydroxide to an endpoint with phenolphthalein.

Example 39

Synthesis of Ficoll (MW 400) Carboxymethyl$_{10}$. (Carboxymethyl Ficoll 400)

Ficoll of molecular weight 400 kDa (0.75 g), and sodium hydroxide (1.15 g) were dissolved in 7.2 ml of deionized water, and were combined with 0.55 g of bromoacetic acid dissolved in 1.425 ml deionized water. The solution was stirred for 2 hours at 25° C., neutralized to pH 7 with 6 N hydrochloric acid, and dialyzed against Spectropor 2 (MWCO 12,000) membrane with deionized water. The retained material was lyophilized. The conjugate contained 10 mmoles of carboxymethyl group per gram of product as determined by titration with sodium hydroxide to an endpoint with phenolphthalein.

Example 40

Synthesis of Inulin Carboxymethyl$_{10}$

Inulin of molecular weight 5 kDa (0.75 g), and sodium hydroxide (1.1 5 g), are dissolved in 7.2 ml of deionized water is combined with 0.55 g of bromoacetic acid dissolved in 1.425 ml deionized water. The solution is stirred for 2 hours at 25° C., neutralized to pH 7 with 6 N hydrochloric acid and dialyzed against Spectropor 2 (MWCO 12,000) membrane with deionized water. The retained material is lyophilized. The conjugate contains 10 mmoles of carboxymethyl group per gram of product as determined by titration with sodium hydroxide to an endpoint with phenolphthalein.

Example 41

Synthesis of Ficoll-CM$_{10}$-ethylenediamine (MW 70 kDa; Amino Ficoll 70)

The carboxyl groups of carboxymethyl ficoll 70 were converted to amines by reaction with ethylene diamine. Carboxymethyl ficoll 70 (0.97 g) was dissolved in 15 ml of water. Ethylene diamine (1.10 ml) and 1-hydroxybenzotriazol (1.25 g) were added, and the pH was adjusted to 6.5. The reagent 1-(3-dimethylaminopropyl)3-ethylcarbodiimide hydrochloride (3.4 g) was added to the Ficoll-CM$_{10}$ solution. The reaction was maintained at 20° C. and pH 6.5 for 24 hours. The reaction was dialyzed against distilled water and lyophilized. The number of amine functional groups introduced is assayed using the OPA Fluorescent assay for primary amines of Pierce Chemical Co. The yield was 8 mmol amine per gram.

Example 42

Synthesis of Ficoll-CM$_{10}$-ethylenediamine (MW 400 kDa; Amino Ficoll 400)

The carboxyl groups of carboxymethyl ficoll 400 were converted to amines by reaction with ethylene diamine. Carboxymethyl ficoll 400 (0.97 g) was dissolved in 15 ml of water. Ethylene diamine (1.10 ml) and 1-hydroxybenzotriazol (1.25 g) were added, and the pH was adjusted to 6.5. 1-(3-dimethylaminopropyl)3-ethylcarbodiimide hydrochloride (3.4 g) was added to the Ficoll-CM$_{10}$ solution. The reaction was maintained at 20° C. and pH 6.5 for 24 hours. The reaction was dialyzed against distilled water and lyophilized. The number of amine functional groups introduced is assayed using the OPA Fluorescent assay for primary amines of Pierce Chemical Co. The yield was 8 mmol amine per gram.

Example 43

Synthesis of Inulin-$CM_{10}$-ethylenediamine (Amino Inulin)

The carboxyl groups of carboxymethyl inulin are converted to amines by reaction with ethylene diamine. Carboxymethyl inulin (0.97 g) is dissolved in 15 ml of water. Ethylene diamine (1.10 ml) and 1-hydroxybenzotriazol (1.25 g) are added, and the pH was adjusted to 6.5. The reagent 1-(3-dimethylaminopropyl)3-ethylcarbodiimide hydrochloride (3.4 g) is added to the Ficoll-$CM_{10}$ solution. The reaction is maintained at 20° C. and pH 6.5 for 24 hours. The reaction is dialyzed against distilled water and lyophilized. The number of amine functional groups introduced is assayed using the OPA Fluorescent assay for primary amines of Pierce Chemical Co.

A chelating group is then used to complex a desired stable isotope and this complex is then reacted with the amino moiety of the amino-polysaccharide. Various bifunctional chelates are used for lanthamide elements, such as samarium, lanthanum, europium, terbium, and dysprosium. One such chelate is ($N^1$-p-isothiocyanatobenzyl)-diethylenetriamine-$N^1,N^2,N^3,N^3$-tetraacetic acid (DTTA) which has been used as a chelating agent to introduce probes used in time-resolved fluoroimmunoassays. For conjugation of DTTA and other similar bifunctional chelates the isothiocyanate group of the chelate reacts with primary amines to form a stable thiourea bond. The reagent is reacted under mild conditions in 0.1M sodium carbonate buffer, pH 9.0. Examples are presented using p-isothiocyanatobenzyl-1,4,7,10-tetraazacyclododecane-1,4,7,10-tetraacetic acid (p-SCN-Bz-DOTA), although use of other bifunctional chelates is contemplated.

Example 44

Labeling of Amino Ficoll 70 with Samarium (Sm-Ficoll 70)

Five μmol of p-isothiocyanatobenzyl-1,4,7,10-tetraazacyclododecane-1,4,7,10-tetraacetic acid (p-SCN-Bz-DOTA) and 4.5 μmol of samarium chloride are incubated in water pH (5.5) for 5 minutes at 25° C. The solution is then added dropwise to 10 mg (0.14 μmol) of Amino Ficoll 70 dissolved in 10 ml of 0.1 M carbonate buffer (pH 9). The reactants are mixed for 60 minutes at 25 C. Succinic acid (100 μmol) is added as a solid, to convert the remaining amino groups to carboxyl groups. The solution is incubated for an additional 60 minutes. The solution is dialyzed and lyophilized to obtain about 10 mg of solid containing 10 mol of Sm per mol of ficoll.

Chemical structure

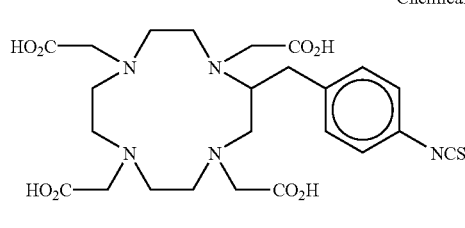

p-SCN-Bz-DOTA

Example 45

Labeling of Amino Ficoll 70 with Lanthanum (La-Ficoll 70)

Five μmol of p-isothiocyanatobenzyl-1,4,7,10-tetraazacyclododecane-1,4,7,10-tetraacetic acid (p-SCN-Bz-DOTA) and 4.5 μmol of lanthanum chloride are incubated in water pH 5 for 5 minutes at 25° C. The solution is then added dropwise to 10 mg of Amino Ficoll 70 dissolved in 10 ml of 0.1 M carbonate buffer (pH 9). The reactants are mixed for 60 minutes at 25 C. Succinic acid (100 μmol) is added as a solid to convert the remaining amino groups to carboxyl groups. The solution is incubated for an additional 60 minutes. The solution is dialyzed and lyophilized to obtain about 10 mg of solid containing 10 mol of La per mol of Ficoll.

Example 46

Labeling of Amino Ficoll 400 with Samarium (Sm-Ficoll 400)

Five μmol of p-isothiocyanatobenzyl-1,4,7,10-tetraazacyclododecane-1,4,7,10-tetraacetic acid (p-SCN-Bz-DOTA) and 4.5 μmol of samarium chloride are incubated in water pH 5 for 5 minutes at 25 C. The solution is then added dropwise to 10 mg of Amino Ficoll 400 dissolved in 10 ml of 0.1 M carbonate buffer (pH 9). The reactants are mixed for 60 minutes at 25 C. Succinic acid (100 μmol) is added as a solid to convert the remaining amino groups to carboxyl groups. The solution is incubated for an additional 60 minutes. The solution is dialyzed and lyophilized to obtain about 10 mg of solid containing 1.7 moles of Sm per mol of Ficoll.

Example 47

Labeling of Amino Ficoll 400 with Lanthanum (La-Ficoll 400)

Five μmol of p-isothiocyanatobenzyl-1,4,7,10-tetraazacyclododecane-1,4,7,10-tetraacetic acid (p-SCN-Bz-DOTA) and 4.5 μmol of lanthanum chloride are incubated in water pH 5 for 30 minutes at 25 C. The solution is then added dropwise to 10 mg of Amino Ficoll 400 dissolved in 10 ml of 0.1 M carbonate buffer (pH 9). The reactants are mixed for 60 minutes at 25 C. Succinic acid (100 μmol) is added as a solid to convert the remaining amino groups to carboxyl groups. The solution is incubated for an additional 60 minutes. The solution is dialyzed and lyophilized to obtain about 10 mg of solid containing 1.7 moles of La per mol of Ficoll.

Example 48

Labeling of Amino Inulin with Samarium (Sm-Inulin)

Five μmol of p-isothiocyanatobenzyl-1,4,7,10-tetraazacyclododecane-1,4,7,10-tetraacetic acid (p-SCN-Bz-DOTA) and 4.5 μmol of samarium chloride are incubated in water pH 5 for 5 minutes at 25 C. The solution is then added dropwise to 10 mg of amino inulin dissolved in 10 ml of 0.1 M carbonate buffer (pH 9). The reactants are mixed for 60 minutes at 25 C. Succinic acid (100 μmol) is added as a solid to convert the remaining amino groups to carboxyl groups. The solution is incubated for an additional 60 minutes. The solution is dialyzed and lyophilized to obtain about 10 mg of solid containing three moles of Sm per mol of inulin.

Example 49

Labeling of Amino Inulin with Lanthanum (La-Inulin)

Five μmol of p-isothiocyanatobenzyl-1,4,7,10-tetraazacyclododecane-1,4,7,10-tetraacetic acid (p-SCN-Bz-DOTA) and 4.5 μmol of lanthanum chloride are incubated in water pH 5 for 30 minutes at 25 C. The solution is then added dropwise to 10 mg of inulin dissolved in 10 ml of 0.1 M carbonate buffer (pH 9). The reactants are mixed for 60 minutes at 25 C. Succinic acid (100 μmol) is added as a solid to convert the remaining amino groups to carboxyl groups. The solution is incubated for an additional 60 minutes. The solution is dialyzed and lyophilized to obtain about 10 mg of solid containing three moles of La per mol of inulin.

Example 50

Labeling of Albumin with Samarium (Sm) Sm-albumin

Five μmol of p-isothiocyanatobenzyl-1,4,7,10-tetraazacyclododecane-1,4,7,10-tetraacetic acid (p-SCN-Bz-DOTA) and 4.5 μmol of samarium chloride were incubated in water pH 5 for 5 minutes at 25° C. The solution was then added dropwise to 6 mg of albumin dissolved in 1 ml of 0.1 M carbonate buffer (pH 9). The reactants were mixed for 60 minutes at 25° C. The solution was dialyzed and lyophilyzed to obtain about 6 mg of solid containing 10 mol of Sm per mol of albumin.

Example 51

Labeling of Ferritin with Lutetium (Lu) Lu-ferritin

Five μmol of p-isothiocyanatobenzyl-1,4,7,10-tetraazacyclododecane-1,4,7,10-tetraacetic acid (p-SCN-Bz-DOTA) and 4.5 μmol of lutetium chloride are incubated in water pH 5 for 5 minutes at 25 C. The solution is then added dropwise to 10 mg of ferritin dissolved in 1 ml of 0.1 M carbonate buffer (pH 9). The reactants are mixed for 60 minutes at 25 C. The solution is dialyzed and lyophylyzed to obtain about 10 mg of solid containing 1.7 moles of Lu per mol of ferritin.

Example 52

Other Chelates that can be used to Introduce Stable Isotopes as Chelates into Ficoll and Inulin and other Polysaccharides Examples of other chelating groups that can be used to modify amino ficoll, other amino polysaccharides, proteins, and other amino containing molecules following a similar chemical strategy indicated in Examples 44–51 include include $N^1$-p-isothiocyanatobenzyl)-diethylenetriamine-$N^1$, $N^2$,$N^3$,$N^3$-tetraacetic acid (DTTA), p-isothiocyanatobenzyl-diethylenetriaminepentaacetic acid (p-SCN-Bz-DTPA), and diethylenetriaminepentaacetic acid (DTPA). In addition, amine terminated chelates such as, 1,4,7,10-tetraazacyclododecane-1,4,7,10-tetraacetic acid mono(p-aminoanilide), 2-p-aminobenzyl-1,4,7,10-tetraazacyclododecane-1,4,7,10-tetraacetic acid, and p-aminobenzyl-diethylenetriaminepentaacetic acid can be coupled to amino polysaccharides using cross linking agents (Pierce, Rockford, Ill.) and can be coupled to carboxyl containing polysaccharides using water soluble carbodiimides.

Example 53

Assay of Sm-Ficoll 70

Preparation of carboxymethyl Sephadex column. To a 10 ml plastic pipet cut off at the 3 ml mark and plugged with glass wool at the bottom, add enough slurry to form a 2 ml volume of the CM Sephadex. Wash the packed resin with 6 ml of 1 M Tris buffer pH 7.5, and 6 ml of 0.01M Tris buffer pH 7.5. Sm-Ficoll 70 is suspended in 0.01 M Tris buffer pH 7.5 (10 ug/ml). Apply fractions as follows. Fraction 1. Three ml of 0.01 M Tris buffer pH 7.5 and allow to drain into column. Fraction 2. One ml of sample Sm-Ficoll 70 and allow to drain into column. Apply 3 ml of 0.01 M Tris buffer pH 7.5 and allow to drain into column. Fraction 3. Three ml of 0.01M Tris buffer pH 7.5 and allow to drain into column. Collect the eluant of fractions 1 through 3. Fraction 4. Column and contents. Dry all fractions at 70° C. for 76 hours and add 25 μl of Arsenic internal standard. Samples are activated by exposure to a neutron flux in a 1 megawatt reactor for 15 minutes. After an interval of three days, samples are counted for 3 minutes.

TABLE 27

| Assay of Sm-Ficoll 70 | | | |
|---|---|---|---|
| Samarium Ficoll 70 from Example 44 | | | % |
| Fraction # | Sample description | dpm | of total |
| 1 | 3 ml of 0.01M Tris buffer pH 7.5 | 0 | 0 |
| 2 | 1 ml of diluted Sm-Ficoll 70 from Example 43 followed by 3 ml of 0.01M Tris buffer pH 7.5 | 1582087 | 98 |
| 3 | 3 ml of 0.01M Tris buffer pH 7.5 | 17089 | 1 |
| 4 | Column and contents | 0 | 0 |
| Samarium chloride from Example 9 | | | % |
| Fraction # | Sample description | dpm | of total |
| 1 | 3 ml of 0.01M Tris buffer pH 7.5 | 0 | 0 |
| 2 | 1 ml of $SmCl_3$ from Example 3 diluted 1:10 followed by 3 ml of 0.01M Tris buffer pH 7.5 | 0 | 0 |
| 3 | 3 ml of 0.01M Tris buffer pH 7.5 | 0 | 0 |
| 4 | Column and contents | 1128598 | 100 |

Results: Table 27 shows that 100% of Sm-Ficoll 70 elutes from the CM-Sephadex column as expected for a negatively charged molecule. In contrast, 100% of unchelated $Sm^{+3}$ is retained on the column as expected for a positive ion. These results demonstrate that Sm-Ficoll 70 forms a stable complex at pH 7.

Example 54

Assay of La-Ficoll 70

Preparation of carboxymethyl sephadex column. To a 10 ml plastic pipet cut off at the 3 ml mark and plugged with glass wool at the bottom, add enough slurry to form a 2 ml volume of the CM sephadex. Wash the packed resin with 6 ml of 1 M Tris buffer pH 7.5, and 6 ml of 0.01M Tris buffer pH 7.5. La-Ficoll 70 is suspended in 0.01 M Tris buffer pH 7.5 (10 ug/ml). Apply fractions as follows. Fraction 1. Three ml of 0.01 M Tris buffer pH 7.5 and allow to drain into column. Fraction 2. One ml of sample La-Ficoll 70 and allow to drain into column. Apply 3 ml of 0.01 M Tris buffer pH 7.5 and allow to drain into column. Fraction 3. Three ml of 0.01M Tris buffer pH 7.5 and allow to drain into column. Collect the eluant of fractions 1 through 3. Fraction 4.

Column and contents. Dry all fractions at 70° C. for 76 hours and add 25 µl of Arsenic internal standard. Samples are activated by exposure to a neutron flux in a 1 megawatt reactor for 15 minutes. After three days samples are counted for 3 minutes.

TABLE 28

Assay of La-Ficoll 70

| Lanthanum Ficoll 70 from Example 45 | | | % |
|---|---|---|---|
| Fraction # | Sample description | dpm | of total |
| 1 | 3 ml of 0.01M Tris buffer pH 7.5 | 0 | 0 |
| 2 | 1 ml of diluted La-Ficoll 70 from Example 44 followed by 3 ml of 0.01M Tris buffer pH 7.5 | 1582087 | 98 |
| 3 | 3 ml of 0.01M Tris buffer pH 7.5 | 17089 | 1 |
| 4 | Column and contents | 0 | 0 |

| Lanthanum chloride from Example 10 | | | % |
|---|---|---|---|
| Fraction # | Sample description | dpm | of total |
| 1 | 3 ml of 0.01M Tris buffer pH 7.5 | 0 | 0 |
| 2 | 1 ml of LaCl$_3$ from Example 10 diluted 1:10 followed by 3 ml of 0.01M Tris buffer pH 7.5 | 0 | 0 |
| 3 | 3 ml of 0.01M Tris buffer pH 7.5 | 0 | 0 |
| 4 | Column and contents | 1128598 | 100 |

Results: Table 28 shows that 100% of La-Ficoll 70 elutes from the CM-Sephadex column as expected for a negatively charged molecule. In contrast, 100% of unchelated La$^{+3}$ is retained on the column as expected for a positive ion. These results demonstrate that La-Ficoll 70 forms a stable complex at pH 7.

Similar results are obtained for Sm-Ficoll 400, La-Ficoll 400, Sm-Inulin, and La-inulin in analogous experiments.

Example 55

Stability of Sm-Ficoll 70 in Rat Serum

To 0.45 ml of rat serum, add 50 µl of 1 mM Sm-Ficoll 70, Sm-Ficoll 400, or Sm-Inulin. Incubate at room temperature for 24 hours. To 0.45 ml of rat serum add 50 ul of Sm chloride.

Incubate at room temperature for 24 hours. Samples were assayed as described in Example 17, except that 0.2 ml of sample was applied to column, and samples were not diluted. Collect fractions as indicated in Table 29. Dry fractions at 70 C for 76 hours and add 25 µl of as internal standard. Samples are activated by exposure to a neutron flux in a 1 megawatt reactor for 15 minutes. After three days, samples are counted for 3 minutes.

Results: Table 29 shows that 100% of the Sm chelates of Ficoll 70, Ficoll 400 and inulin elute from CM Sephadex columns while approximately 50% of the respective samarium salt is bound to the column. The portion of unchelated salt eluting from the column is a result of the free metal ions binding to serum components. Since all of the chelates elute from the CM-column, one concludes that little to no serum binding occurs for the three test compounds. Based on the minimum number of dpms detectable on the column, one concludes that less than 2% of the samarium dissoiates from Ficoll 70, Ficoll 400 or Inulin.

TABLE 29

Fractionation of Sm chelates of Ficoll 70, Ficoll 400 and Inulin on Cm Sephadex as an indication of serum binding

| | Samarium-Ficoll 70 in rat serum | dpm | % of total |
|---|---|---|---|
| 1 | Apply 0.2 ml of Sm-Ficol 70 incubated in rat serum, allow sample to drain into column followed by 2 ml of 0.01M Tris buffer pH 7.5 | 287916 | 99 |
| 2 | 3 ml of 0.01M Tris buffer pH 7.5 | 1213 | <1 |
| 3 | Column and contents | 0 | 0 |

| | Samarium-Ficoll 400 in rat serum | dpm | % of total |
|---|---|---|---|
| 1 | Apply 0.2 ml of Sm Ficoll 400 incubated in rat serum, allow sample to drain into column followed by 2 ml of 0.01M Tris buffer pH 7.5 | 82912 | 93 |
| 2 | 3 ml of 0.01M Tris buffer pH 7.5 | 6167 | 7 |
| 3 | Column and contents | 0 | |

| | Samarium-Inulin in rat serum | dpm | % of total |
|---|---|---|---|
| 1 | Apply 0.2 ml Sm-Inulin incubated in rat serum, allow sample to drain into column followed by 2 ml of 0.01M Tris buffer pH 7.5 | 4763 | 91 |
| 2 | 3 ml of 0.01M Tris buffer pH 7.5 | 499 | 9 |
| 3 | Column and contents | 0 | 0 |

| | Samarium chloride in rat serum (data from Example 22) | dpm | % of total |
|---|---|---|---|
| 1 | Apply 0.2 ml of SmCl$_3$ incubated in rat serum, allow sample to drain into column followed by 2 ml of 0.01M Tris buffer pH 7.5 | 104992 | 48 |
| 2 | 3 ml of 0.01M Tris buffer pH 7.5 | 5702 | 3 |
| 3 | Column and contents | 108299 | 49 |

Example 56

Simultaneous Bioassay of Lu-DTPA, Sm-Ficoll 70 and La-Ficoll 400 in Healthy Rats This example illustrates the application of using multiple compounds labeled with different stable isotopes to measure simultaneously different biological activities. In this example, Lu-DTPA is used to measure glomerular filtration rate, while Sm-Ficoll-70 and La-Ficoll 400 are used to measure degradation of glomerular size selectivity. As the glomerular structure breaks down over time, first assay compounds such as Sm-Ficoll-70, of molecular weight or size just above the cut off limit of normally functioning glomerulus, will pass into the urine, followed later in disease progression by larger molecules such as La-Ficoll-400, which will pass into the urine as a result of further glomerular deterioration.

In this example in normal rats with healthy glomerular filtration, only the Lu-DTPA will pass into the urine. The Sm-Ficoll-70 however is small enough to equilibrate with the interstitial space accounting for an initial decrease in blood concentration. This molecule will then slowly leave the blood but remain in the animal. Sa-Ficoll-400, because of its higher molecular weight will remain in the blood and not equilibrate readily with the interstitial space. It will slowly leave the blood through opsonization processes.

Biodistribution

Rats (300–375 g) used in all studies are male hooded/BBZDR from BioMedical Research Models (Worcester, Mass.). For each set of experiments, three rats are anesthetized with Nembutal. The carotid artery and jugular vein are exposed, and each animal receives via jugular vein an injection of Lu-DTPA, Sm-Ficoll 70 and La-Ficoll 400 (50 ug/kg). At various times, blood samples are removed from the tail. Urine samples are collected using a metabolic cage.

Neutron Activation.

Lutetium, samarium, and lanthanum content in all samples are each quantitated by the user's facility (for example, BioPAL, Worcester, Mass.; www.biopal.com). Samples are placed in 2-ml polypropylene tubes free of trace element contaminants and dried at 70° C. for at least 12 hours. An internal standard of tungsten is added to each sample, to correct for variations in neutron flux. Samples are activated for 15 minutes in a neutron field created by a 2-megawatt nuclear reactor. Short lived activated products, principally resulting from sodium and chloride, are allowed to decay for two days, and the remaining radioactivity from activated samarium or gold is counted using a high resolution gamma spectrometer.

The fate of Lu-DTPA, Sm-Ficoll 70 and La-Ficoll 400 after intravenous injection into rats is examined by obtaining the biodistribution of the compounds 24 hours after injection. Biodistribution of the compounds is inferred by the presence of lutetium, samarium, and lanthanum in tissues after the injection of Lu-DTPA, Sm-Ficoll 70 and La-Ficoll 400. Lu-DTPA is found only in the urine, consistent with its low molecular weight and lack of strong interaction with blood components and cells. Sm-Ficoll 70 and La-Ficoll 400 are present in the liver (~10–20% of injected dose), with most of the initial dose remaining in the blood after 24 hours, consistent with a long blood-half life. Blood levels of Sm-Ficoll 70 are lower due to its ability to enter the interstitial space compared with La-Ficoll 400, which remains principally in the blood. Trace amounts are found in the spleen, lung, and muscle. The lack of renal clearance of Sm-Ficoll 70 and La-Ficoll 400 is consistent with their molecular weights. Blood clearance and appearance in the urine as a function of time for Lu-DTPA, Sm-Ficoll 70 and La-Ficoll 400 are presented in Table 30. These results are consistent with the literature reports for low molecular weight chelates and high molcular weight polymers.

TABLE 30

Bioassay of Lu-DTPA, Sm-Ficoll 70 and La-Ficoll 400 in healthy rats

| Time | Lu | Sm | La | Lu | Sm | La |
|---|---|---|---|---|---|---|
| | % of initial injection in blood | | | % of initial injection in urine | | |
| 0 | 100 | 100 | 100 | 0 | 0 | 0 |
| 15 min | 80 | | | | | |
| 30 min | 61 | | | 22 | | |
| 60 min | 34 | 85 | 98 | | 2 | 0 |
| 4 hr | 2 | | | 92 | | |
| 8 hr | | | | 96 | | |
| 16 hr | | | | | | |
| 24 hr | 0 | 47 | 83 | 100 | 5 | 0 |

Example 57

Synthesis of the Ethylene Diamine Amide of Cholic Acid (EDAC)

Activation of cholic acid [1]. In a 20 ml vial, 1 g cholic acid was dissolved in 5 ml dimethylformamide. N-methylmorpholine (0.286 ml) was added and mixed. Ethylchloroformate (0.3 ml) was diluted in 2.7 ml dimethylformamide and immediately added to the cholic acid dropwise with mixing. The mixture was reacted for 30 minutes at room temperature, and formation of a precipitate was observed.

Formation of the ethylene diamine amide of cholic acid [2]. Ethylene diamine (0.7 ml) was added to 5 ml dimethylformamide dropwise with stirring to the activated cholic acid, and allowed to react for 60 minutes at room temperature. A gummy oil precipitated on the glass container.

Purification. The supernatant was added to 50 ml of water, and a milky suspension was obtained. This was dialyzed against water to remove low molecular contaminants while retaining the colloidal product.

Alternative purification. Add 5 ml of water (pH 8.5) to the reaction in [2], and extract three times with 10 ml of ethyl acetate. Back extract the ethyl acetate twice with water (pH 8.5).

Dry the ethyl acetate over anhydrous magnesium sulfate, and evaporate the ethyl acetate to obtain the product of the yield of which was 733 mg.

Example 58

Labeling of [2] with Samarium (Sm-cholic Acid). Labeling a Bile Acid

Five μmol of p-isothiocyanatobenzyl-1,4,7,10-tetraazacyclododecane-1,4,7,10-tetraacetic acid (p-SCN-Bz-DOTA) and 4.5 μmol of samarium chloride are incubated in water pH (5.5) for 5 minutes at 25° C. The solution is then added dropwise to 5 mmol of ethylene diamine amide of cholic acid in the reaction of [2] dissolved in 0.1 M carbonate buffer pH 9. The reactants are mixed for 60 minutes at 25 C to obtain Sm-cholic acid [3].

Purification. Add 5 ml of water (pH 8.5) to [3] and extract three times with 10 ml of ethyl acetate to remove unreacted ethylene diamine amide of cholic acid in the reaction of [2].

Discard the ethyl acetate, and dry the aqueous phase by lyophilization to obtain the p-isothiocyanatobenzyl-1,4,7,1 0-tetraazacyclododecane-1,4,7,1 0-tetraacetic acid adduct of ethylene diamine amide of cholic acid.

Example 59

Labeling of Glycine with Samarium (Sm-glycine). Labeling an Amino Acid

Five μmol of p-isothiocyanatobenzyl-1,4,7,10-tetraazacyclododecane-1,4,7,10-tetraacetic acid (p-SCN-Bz-DOTA) and 4.5 μmol of samarium chloride are incubated in water pH (5.5) for 5 minutes at 25° C. The solution is then added dropwise to 7 mmol of glycine dissolved in 0.1M carbonate buffer (pH 9). The reactants are mixed for 60 minutes at 25 C to obtain Sm-glycine.

Purification. The product is purified by ultrafiltration using a 500 molecular weight cutoff membrane to separate unreacted glycine (MW 75) from the p-isothiocyanatobenzyl-1,4,7,10-tetraazacyclododecane-1,4,7,10-tetraacetic acid adduct of glycine (MW 937). The retained fraction is dried by lyophilization to obtain a white powder.

Example 60

Labeling of Folate with Samarium (Sm-folate). Labeling a Vitamin

Five μmol of p-amino-benzyl-1,4,7,10-tetraazacyclododecane-1,4,7,10-tetraacetic acid (p-amino-Bz-DOTA) and 4.5 μmol of samarium chloride are incubated in water pH (5.5) for 5 minutes at 25° C. The solution is then added to 7 μmol of folate and 30 mmol of EDAC (water soluble carbodiimide) dissolved in 0.1pyridine buffer (pH 5.5). The reactants are mixed for 180 minutes at 25 C to obtain Sm-folate.

Purification. The product is purified by ultrafiltration using a 500 molecular weight cutoff membrane to separate unreacted EDAC and folate from the p-amino-1,4,7,10-tetraazacyclododecane-1,4,7,10-tetraacetic acid-Sm adduct of folate. The retained fraction is dried by lyophilization to obtain a white powder.

Example 61

Labeling of Estradiol with Samarium (Lu-estradiol). Labeling a Steroid

Estradiol-17β-hemisuccinate prepared by reaction of estradiol and succinic anhydride following procedures known in the art. The hemisuccinate is then activated with ethylchloroformate and reacted with an excess of p-amino-benzyl-1,4,7,10-tetraazacyclododecane-1,4,7,10-tetraacetic acid. Unreacted p-amino-benzyl-1,4,7,10-tetraazacyclododecane-1,4,7,10-tetraacetic acid is separated from the estradiol-p-amino-benzyl-1,4,7,10-tetraazacyclododecane-1,4,7,10-tetraacetic acid adduct by extraction with ethylacetate against pH 2 water. The purified adduct is charged with a stoichiometric amount of $LuCl_3$ to form Lu-estradiol.

Example 62

Labeling of Tobramycin with Samarium (Sm-tobramicin). Labeling an Antibiotic

Five μmol of p-isothiocyanatobenzyl-1,4,7,10-tetraazacyclododecane-1,4,7,10-tetraacetic acid (p-SCN-Bz-DOTA) and 4.5 μmol of samarium chloride are incubated in water pH (5.5) for 5 minutes at 25° C. The solution is then added dropwise to 7 μmol of tobramycin dissolved in 0.1M carbonate buffer (pH 9). The reactants are mixed for 60 minutes at 25 C to obtain Sm-tobramycin.

Purification. The product is purified by ultrafiltration using a 500 molecular weight cutoff membrane to separate unreacted tobramycin (MW 467) from the p-isothiocyanatobenzyl-1,4,7,10-tetraazacyclododecane-1,4,7,10-tetraacetic acid adduct of tobramycin (MW 1329). The retained fraction is dried by lyophilization to obtain a white powder.

Example 63

Measurement of Sm-cholic Acid Clearance from the Blood Patients and Control Groups Sixteen patients are evaluated at the National Institutes of Health (N.I.H.) under an Institutional Review Broad-Approved protocol. The following procedure is followed for all patients in the study.

Nine patients with clinical diagnosis of Laennec's cirrhosis, confirmed by liver biopsy, are selected for the study (Table 1). None of the patients is azotemic or in hepatic coma when studied, although the majority have ascites and are undergoing diuretic therapy. The age, sex and liver function tests are listed in Table 31. The control group, consisting of seven patients similar in age to the cirrhotic group, are hospitalized patients having no clinical or laboratory evidence of liver or biliary tract disease.

TABLE 31

Clinical information and bile acid data on patients with Laennec's cirrhosis

| Sex/Age | Bilirubin Direct/Total mg/100 ml | Albumin/Globulin g/100 ml | Prothrombin time/patient over control Seconds | Ascites* | Esophageal varices ⊥ |
|---|---|---|---|---|---|
| M/56 | 5.8/9.3 | 2.3/4.1 | 20/13 | + | + |
| F/48 | 10.2/14.2 | 2.6/3.8 | 21/14 | ++ | + |
| M/60 | 1.6/3.0 | 2.5/4.0 | 20/13 | ++ | + |
| M/62 | /1.8 | 3.3/3.6 | 22/14 | ++ | + |
| M/42 | /1.4 | 2.4/3.8 | 19/13 | ++ | + |
| M/54 | /1.0 | 3.0/4.0 | 16/13 | | + |
| M/40 | 6.4/8.4 | 2.8/3.1 | 21/14 | ++ | |
| M/38 | 11.4/14.0 | 3.1/3.3 | 26/14 | ++ | + |
| M/60 | 1.6/ | 4.0/3.0 | 22/14 | | + |

*+ = physical signs without increased abdominal girth; ++ = increased abdominal girth; ⊥ = by radiology or esophagoscopy.

Methods

The dose of each labeled agent is determined by weight. $^{14}C$-Cholic acid (0.14 μCi/kg) and Sm-cholic acid (0.01 mg/kg) are simultaneously administered to each patient i.v. Serial plasma specimens are obtained from a vein other than the one injected at time points 10, 20, 40, and 60-minutes, and then daily, after injection. The volume of each plasma collection is measured, than $^{14}C$ and Sm concentration are determined (scintillation counting for $^{14}C$; neutron activation for Sm).

Scintillation Count of Samples

Half of the volume of plasma of each sample is used to determine the $^{14}C$-cholic acid concentration. The $^{14}C$-cholic acid samples are counted in a scintillation counter as is known in the art. The $^{14}C$-cholic acid clearance rate is calculated from these data in accordance with standard methods known in the art.(14,60)

Neutron Activation Analysis

The other half of the plasma volume is used to determine Sm-cholic acid concentration. Plasma samples are placed in vials containing pre-added monitor to correct for neutron flux variations, and are mailed to the facility, e.g., BioPAL, Inc. for analysis. Samples are activated by exposure to a high neutron flux generated by a two megawatt reactor for 15-minutes. After two days of decay, samples are counted for 3-minute using a high-resolution gamma-ray counting system. Samarium concentration in each sample is determined using a standard curve developed with a reference batch of samarium of known concentration.

Computation of the Results

Rates of clearance of injected Sm-cholic acid in a group of seven normal subjects during the first 60-minutes are compared to that of nine patients with cirrhosis (FIG. 4). In the normal group, the mean half time of cholic acid is 30.7±6.2 minutes, whereas in the cirrhotic group the half time is approximately four times longer, averaging 120.7±53.9 minutes. The difference is highly significant.

TABLE 32

Clearance rates in (min) for labeled cholic acid in Laennec's cirrhotic and normal patients.

| | Laennec's Cirrhosis | | | | | Normal Control | | | |
|---|---|---|---|---|---|---|---|---|---|
| | $^{14}C$ | $r^2$ | Sm | $r^2$ | | $^{14}C$ | $r^2$ | Sm | $r^2$ |
| 1 | 67.5 | 0.96 | 64.7 | 0.97 | 1 | 29.3 | 0.98 | 28.5 | 1.00 |
| 2 | 75.8 | 0.99 | 73.0 | 0.99 | 2 | 33.3 | 0.97 | 30.9 | 0.99 |
| 3 | 105.1 | 0.99 | 95.8 | 1.00 | 3 | 33.6 | 0.97 | 34.6 | 0.98 |
| 4 | 113.3 | 0.99 | 115.8 | 1.00 | 4 | 17.3 | 0.96 | 18.2 | 0.96 |
| 5 | 165.7 | 0.97 | 150.9 | 0.99 | 5 | 34.1 | 0.99 | 32.7 | 0.99 |
| 6 | 181.3 | 0.96 | 195.0 | 0.96 | 6 | 33.8 | 0.98 | 37.4 | 0.99 |
| 7 | 223.3 | 0.97 | 213.7 | 0.97 | 7 | 33.3 | 0.96 | 32.6 | 0.97 |
| 8 | 80.2 | 0.98 | 89.6 | 0.99 | | | | | |
| 9 | 88.7 | 0.97 | 87.6 | 0.99 | | | | | |
| Average | 122.3* | | 120.7h | | Average | 30.7 | | 30.7 | |
| s.d. | 54.7 | | 53.9 | | s.d. | 6.1 | | 6.2 | |

P = NS $^{14}C$ vs. Sm in Laennec's cirrhosis group; P = NS $^{14}C$ vs. Sm in control group; *P = 0.0006 Laennec's cirrhosis group vs. control for $^{14}C$-cholic acid; h P = 0.0006 Laennec's cirrhosis group vs. control for SM-cholic acid.

Similar values are obtained using co-injected $^{14}C$-cholic acid. Table 32 lists values obtained for each patient. In the normal group, mean half-time of cholic acid is 30.7±6.1 minutes, whereas in the cirrhotic group the half-time is approximately four times longer, averaging 122.3±54.7 minutes. The difference is again highly significant. In both groups, no significant difference is observed when values obtained by $^{14}C$-cholic acid are compared to values obtained by Sm-cholic acid. In the normal subjects, plasma activity ($^{14}C$ and Sm) is undetectable in all specimens obtained more than 6-hours after injection. In striking contrast, significant plasma activity is demonstrable for up to 14 days.

Example 64

Bioassay of Sm-taurocholic Acid (Sm-TCA) Oral Ingestion Patient Group

Twenty consecutive patients with chronic or recurrent diarrhea of unknown cause are investigated with Sm-TCA and $^{75}$SeHCAT test. Urgent watery diarrhea is the major problem in all patients. Lactose restricted diet, loperamide or anticholinergic agents has not relieved their symptoms. Patients with periods of constipation, dominating abdominal pain or fragmented mucus stool are excluded. All patients have a long history of diarrhea without known cause, and a mean age of 13 years (range 3 months to 30 years). Clinical, endoscopic and radiological examinations are performed, as well as laboratory tests, to exclude inflammatory bowel disease, lactose intolerance, celiac disease, abuse of laxatives or other causes of diarrhea.

Methods

One capsule of 10 ΦCi $^{75}$SeHCAT (Amersham International) and one capsule of 0.7 mg Sm-TCA (BioPAL, Inc.) are simultaneously swallowed with water by the patient after an overnight fast. Stool samples are collected every 24-hours over a 5-day period. The date and time of collection are recorded.

Measurement of $^{75}$SeHCAT

Samples of homogenized 24-hour stool collections are precisely weighed and combusted in a tube-oven. Radioactivity is measured using a collimated 2-inch NaI crystal in a selected standard geometry, as is known in the art. Daily excretion is expressed as the fraction of the administered dose. Elimination of bile acids from a pool is found to follow first order kinetics; turnover is expressed as half-time (days) of elimination of the administered dose of $^{75}$SeHCAT in accordance with standard methods known in the art.(25)

Neutron Activation Analysis

Dried stool samples are placed in vials containing monitor to correct for neutron flux variations and are mailed to a facility, for example, BioPAL, Inc. for analysis. Samples are activated by exposure to a high neutron flux generated by a two megawatt reactor for 15-minutes. Following two days of decay, samples are counted for 3-minute using a high-resolution gamma-ray counting system. Samarium concentration in each sample is determined using a standard curve developed with reference samarium. The results obtained for Sm-TCA are expressed above as for $^{75}$SeHCAT.

Computation of the Results

As shown in FIG. 5, daily excretion of each tracer, expressed as percentage of the administered dose, shows an excellent correlation with the other tracer (P<0.005, paired t-test). Both tracers exhibit identical physical behavior with respect to resorption and excretion phenomena. As shown in FIG. 6, no significant deviation from the identical function is found (P>0.05, paired t-test) when the half-times of the bile acid elimination are compared.

Example 65

Preparation of Arabinogalactan Coated Ferrite Particles

A general process for the preparation of arabinogalactan coated ferrite particles follows.(25) An aqueous solution of trivalent and divalent metal salts is prepared by use of the following amounts of ferric and ferrous halide salts: $FeCl_3 \cdot 6H_2O$ (15.8 g, 58.6 mmol) and $FeCl_2 \cdot 4H_2O$ (6.24 g, 31.6 mmol) are combined in 200 ml distilled water and the resulting solution is filtered through a 0.22 μm filter. Equal volumes of this metal halide solution and a carbohydrate solution, prepared by dissolving arabinogalactan (from larch wood, 60 g, Sigma Chemical Co.) in 120 ml distilled water are then combined at ambient temperature with stirring. To this mixture is added dropwise a 30% solution of ammonium hydroxide until the pH of the mixture reaches about 10, and the mixture is heated to 90° C. for 15 minutes. The mixture is cooled, and a black colloidal superparamagnetic iron oxide is obtained. Excess arabinogalactan is removed by ultrafiltration using a 300 kDa molecular cutoff membrane. The filtered product, obtained with a yield in iron of about 90%, is refrigerated until needed.

Following this procedure a number of new products labeled with stable isotopes can be made without change to the above chemical procedure, other than the substitution of one isotope or one element for either ferric or ferrous chloride. Illustrative of possible metal atom substitutions are the substances and proportions presented in Table 33 This list is presented for purposes of illustration and should not be construed to limit the possible types of substitutions by stable isotope labeled metals.

TABLE 33

Possible metal substitutions in the preparation of ferrites

Sample 1  50% of $^{56}Fe^{3+}$ will be substituted with an equivalent molar amount of $^{58}Fe^{3+}$
Sample 2  10% of $^{56}Fe^{2+}$ will be substituted with an equivalent molar amount of $^{57}Co^{2+}$
Sample 3  20% of $^{56}Fe^{2+}$ will be substituted with an equivalent molar amount of $^{57}Co^{2+}$
Sample 4  10% of $^{56}Fe^{3+}$ will be substituted with an equivalent molar amount of $Sm^{3+}$
Sample 5  20% of $^{56}Fe^{3+}$ will be substituted with an equivalent molar amount of $Sm^{3+}$
Sample 6  10% of $^{56}Fe^{3+}$ will be substituted with an equivalent molar amount of $La^{3+}$
Sample 7  20% of $^{56}Fe^{3+}$ will be substituted with an equivalent molar amount of $La^{3+}$ Example 66

Preparation of Arabinogalactan Coated Non Ferrite Particles

A general process for the preparation of arabinogalactan coated non-ferrite particles follows. An aqueous solution of trivalent or divalent metal salt (M) is prepared by use of the following amounts of salt: $MCl_2$ or $MCl_3$ (58.6 mmol) is dissolved in 200 ml distilled water and is filtered through a 0.22 μm filter. Equal volumes of this metal halide solution and a carbohydrate solution, prepared by dissolving arabinogalactan (from larch wood, 60 g, Sigma Chemical Co.) in 120 ml distilled water are then combined at ambient temperature with stirring To this mixture is added dropwise a 30% solution of ammonium hydroxide, until the pH of the mixture reaches about 10, and the mixture is heated to 90° C. for 15 minutes. The mixture is cooled, and a colloidal metal oxide is formed. Excess arabinogalactan is removed by ultrafiltration using a 300 kDa molecular cutoff membrane. The filtered product, obtained with a yield in M of about 90%, is refrigerated until needed. M is chosen so that it contains a stable isotope suitable for neutron activation. Following this procedure a number of new products can be made without change in the chemical procedure other then the substitution of one isotope or one element for M chloride.

Example 67

Synthesis of Colloidal Gold Coated with Galactose Clusters

Gold nano-particles of size 10 nm coated with albumin are purchased from Sigma Chemical Co. The surface coat of albumin is modified with lactose to produce a lactosylated albumin coated gold nanoparticle. Galactose terminal sugars are coupled to albumin using lactose, a reducing disaccharide, by the method of Schwartz and Gray as follows. [Schwartz, 1977 #132] Sixty-seven milligrams of albumin coated gold nanoparticles, 100 mg of lactose containing 10 μCi of $^{14}C$-lactose, and 42 mg of sodium cyanoborohydride are dissolved in 5 ml of 0.2 M potassium phosphate buffer (pH 7), and incubated at room temperature for about 100 hr. Upon completion of the reaction excess reagents are removed by diafiltration.

Example 68

Synthesis and Filter Sterilization of Colloidal Gold Coated with Galactose Clusters (PolyGalactoseGold™)

Uncoated 10 nm gold particles are purchased form Sigma Chemical Co. These particles are added to an aqueous solution of lactosylated albumin (5 mg/ml) incubated for 30 minutes at room temperature and are ultrafiltered against a 300 kDa molecular weight cutoff membrane, with five changes of phosphate buffered saline (pH 7.4) to remove excess lactosylated albumin. The resulting solution is passed through a 0.2 μm filter, and the sterile solution is stored at 4° C.

Example 69

Measurement of Receptor Activity Using Colloidal Gold Coated with Multiple Galactose Moieties (Example 68)

While effort has been devoted to developing drug delivery systems utilizing the asialoglycoprotein receptor, there is still a need for simple, easy to use assays to measure this receptor activity in vivo. In this example, measurement of the asialoglycoprotein receptor in normal rats is presented using stable isotope labeling and neutron activation.

Receptor Interaction and Biodistribution.

Rats (300–375 g) used in all studies were male hooded/BBZDR from BioMedical Research Models (Worcester, Mass.). For each set of experiments three rats were anesthetized with Nembutal. The carotid artery and jugular vein were exposed and the animal administered PolyGalactose-Gold (50 μg/kg) or albumin coated gold (50 μg/kg) via jugular vein injection. Second set of animals was injected with 100 mg/kg of asialofetuin followed by PolyGalactose-Gold. At various times blood samples were removed from the carotid artery.

After 60 minutes the animals were sacrificed and approximately one-gram amounts of various tissues were recovered for quantitation of samarium or gold. Tissues were blotted to remove blood and clots. No additional processing of tissue such as perfusion was necessary to perform neutron activation analysis.

Neutron Activation.

Gold content in all samples was quantitated by a facility such as BioPAL (Worcester, Mass.; www.biopal.com). Samples were placed in 2-ml polypropylene tubes free of trace element contaminants and dried at 70° C. for a minimum of 12 hours. An internal standard of tungsten, to correct for variations in neutron flux, was added to each sample. Samples were activated for 15 minutes in a neutron field created by a 2-megawatt nuclear reactor. Short lived activated products, principally resulting from sodium and chloride, were allowed to decay for two days and the remaining radioactivity from activated samarium or gold was counted using a high resolution gamma spectrometer.

The fate of PolyGalactoseGold after intravenous injection into rats and mice was examined by obtaining the biodistribution of the conjugate 60 minutes after injection. Biodistribution of the conjugate was inferred by the presence of gold in tissues after the injection of PolyGalactoseGold. PolyGalactoseGold was found to be present in the liver (~100% of injected dose) but not in the spleen, adrenals, lung, kidney, heart, marrow, brain, muscle or urine. When asialofetuin, a ligand for the asialoglycoprotein receptor of hepatocytes, was coinjected with PolyGalactoseGold, blood clearance of PolyGalactoseGold was substantially slower (FIG. 3). When albumin coated colloidal gold (see Example 66) was substituted for PolyGalactoseGold, blood clearance for albumin coated gold was also substantially slower than that seen with PolyGalactoseGold, demonstrating the specific role of galactose for clearing PolyGalactoseGold. These results are consistent with the literature reports that lactosylated albumin is a ligand of the asialoglycoprotein receptor, and indicate that the hepatic clearance of PolyGalactoseGold was mediated by the asialoglycoprotein receptor. The lack of renal clearance of PolyGalactoseGold is consistent with its size (20 nm) which corresponds to a molecule about the size of IgM.

Using the activation procedure described in the methods, one nanogram of gold corresponding to about 800 dpm could be easily distinguished from the background (about 5 dpm).

REFERENCES

1. SNAPKA, R. M., KWOK, K., BERNARD, J. A., HARLING, O. K., and VARSHAVSKY, A. Post-separation detection of nucleic acids and proteins by neutron activation, Proc. Natl. Acad. Sci. USA. 83: 8939–8942, 1986.
2. FALLEY, M. P., ANDERSON, D. L., ZOLLER, W. H., GORDON, G. E., and LINDSTROM, R. M. Neutron-capture prompt gamma-ray activation analysis for multi-element determination in complex samples, Anal. Chem. 51: 2209–2221, 1979.
3. KITCHIN, K. T. and BROWN, J. L. Incorporation of 5-iodo-2'-deoxyuridine and 5-bromo-2'-deoxyuridine into rodent DNA as determined by neutron activation analysis, Anal. Biochem. 229: 180–187, 1995.
4. CHOU, F. I., LIN, H. D., WEI, J. C., WANG, A. Y., and LO, J. G. Simplified measurement of protein-bound iodine with epithermal neutron activation analysis, Nucl. Med. Biol. 20: 631–636, 1993.
5. KIM, H. W., YU, Y. J., and GREENBURG, A. G. Iron-58 and neutron activation analysis: A non-radioactive method for tracing hemoglobin iron, Art. Cells, Blood Subs., and Immob. Biotech. 22: 619–624, 1994.
6. KILLIAN, E. W., KOEPPEN, L. D., and FEMEC, D. A. Quality-assurance techniques used with automated analysis of gamma-ray spectra, Radioact. Radiochem. 5: 34–41, 1994.
7. NEER, R., TULLY, G., SCHATZ, P., and HNATOWICH, D. J. Use of stable 48Ca in the clinical measurement of intestinal calcium absorption, Calcif. Tiss. Res. 26: 5–11, 1978.
8. LAUFFER, R. B. Paramagnetic metal complexes as water proton relaxation agents for NMR imaging: Theory and design, Chem. Rev. 87: 901–927, 1987.
9. BETEBENNER, D. A., CARNEY, P. L., ZIMMER, A. M., KAZIKIEWICZ, J. M., BRUCHER, E., SHERRY, A. D., and JOHNSON, D. K. Hepatobiliary delivery of polyaminopolycarboxylate chelates: Synthesis and characterization of a cholic acid conjugate of EDTA and biodistribution and imaging studies with its indium-111 chelate, Bioconjugate Chem. 2: 117–123, 1991.
10. GOECKELER, W. F., EDWARDS, B., VOLKERT, W. A., HOLMES, R. A., SIMON, J., and WILSON, D. Skeletal localization of samarium-153 chelates: Potential therapeutic bone agent, J. Nucl. Med. 28: 495–504, 1987.
11. SIGMAN, E., ELWOOD, C., REAGAN, M., MORRIS, A., and CATANZARO, A. The renal clearance of 131I-labeled sodium iothalamate in man, Invest Urol. 2: 432, 1965.
12. COHEN, M., SMITH, F., Jr., MINDELL, R., and VERNIER, R. A simple reliable method of measuring glomerular filtration rate using single low dose sodium iothalamate 131-I, Pediatircs. 43: 407, 1969.
13. N-E BACK et al., 72, 765 (1988)). J. Pharm. Sci. 72: 765, 1988.
14. TWEEDLE Relaxation Agents in NMR Imaging. In: J. -C. G. Bunzli and G. R. Choppin (eds.), Lanthamide Probes in Life, Chemical and Earth Sciences, Theory and Practice, pp. 127–179: Elsevier, 1989.
15. AGODOA, L., EKNOYAN, G., GELFINGER, J., KEANE, W., MAUER, M., MITCH, W., STRIKER, G., and WILCOW, C. Assessment of structure and function in progressive renal disease, Kidney Int. 52: S144–S150, 1997.
16. APPERLOO, A. J., DE ZEEUW, D., DONKER, A. J. M., and DE JONG, P. E. Precision of glomerular filtration rate determinations for long-term slope calculations in improved by simultaneous infusion of 125I-iothalamate and 131I-hippuran, J. Am. Soc. Nephrol. 7: 567–572, 1996.
17. GASPARI, F., N. PERICO, N., and REMUZZI, G. Measurement of glomerular filtration rate, Kidney Int. 52: S151–S154, 1997.
18. PERRONE, R. D., MADIAS, N. E., and LEVEY, A. S. Serum creatinine as an index of renal function: New insights into old concepts, Clin. Chem. 38: 1933–1953, 1992.
19. BARNAS, U. and MAYER, G. Glomerular proteinuria in renal transplant patients: Mechanisms and treatment, Kidney Int. 52: 52:S78–S80, 1997.
20. RUSTOM, R., GRIME, J. S., MALTBY, P., STOCKDALE, H. R., JACKSON, M. J., CRITCHLEY, M., and BONE, J. M. Renal tubular protein degradation of radio-labelled aprotinin (Trasylol) in patients with chronic renal failure, Clin. Sci. 85: 733–736, 1993.
21. BLOUCH, K., DEEN, W. M., FAUVEL, J., BIALEK, P. J., DERBY, G., and MYERS, B. D. Molecular configuration and glomerular size selectivity in healthy and nephrotic humans, Am. J. Physiol. 42: F430–F437, 1997.
22. SCANDLING, J. D., BLACK, V. M., DEEN, W. M., and MYERS, B. D. Glomerular permselectivity in healthy and nephrotic humans, Advances in Nephrology. 21: 159–176, 1992.
23. KAKUTA, T., SUZUKI, Y., HIDA, M., M. WAKABAYASI, FUJISAKI, T., KITAMURA, M., and HIRAGA, S. Functional evaluation of the remaining kidney in kidney donors by radionuclide dynamic imaging using a graphic method with factor analysis, Nucl. Med. Comm. 18: 937–942, 1997.
24. LUFFT, V., KLIEM, V., HAMKENS, A., BLECK, J. B., EISENBERGER, U., PETERSEN, R., EHLERDING, G., MASCHEK, H., PICHLMAY, R., and BRUNKHORST, R. Antiproteinuric efficacy of fosinopril after renal transplantation is determined by the extent of vascular and tubulointerstitial damage, Clin Transplantation. 12: 409–415, 1998.
25. WALSER, M., DREW, H. H., and LAFRANCE, N. D. Creatinine measurements often yield false estimates of progression in chronic renal failure, Kidney Int. 34: 412–418, 1988.
26. EDWARDS, A. and DEEN, W. M. Error propagation in the estimation of glomerular pressure from marcromolecule sieving data, Am. J. Physiol. 37: F736–F745, 1995.
27. HULME, B. Studies on glomerular permeability using inert polymers, Contrib Nephrol. 1: 3–8, 1975.
28. DE BELDER, A. N. and GRANATH, K. Preparation and properties of fluorescein-labelled dextrans, Carbohydrate Res. 30: 375–378, 1973.
29. REMUZZI, A., BATTAGLIA, C., ROSSI, L., ZOJA, C., and REMUZZI, G. Glomerular size selectivity in nephrotic rats exposed to diets with different protein content, Am. J. Physiol. 253: F318–F327, 1987.
30. LANG, T., SENDL, A. F., ESPUIVEL, C. O., BERQUIST, W. E., and COX, K. L. Cholic acid synthesis is reduced in pediatic liver recipients during graft dysfunction due to ischemic injury and allograft rejection, Transplantation. 64: 1585–1590, 1997.
31. THEILMANN, L., OTTO, G., ARNOLD, J., GMELIN, K., and STIEHL, A. Biliary secretion of bile acids, lipids, and bilirubin by the transplanted liver: A quantitative study in patients on cyclosporine, Transplantation. 52: 1020–1023, 1991.
32. MCCORMICK, W. C., III, BELL, C. C., JR., SWELL, L., and VLAHCEVIC, Z. R. Cholic acid synthesis as an index of the severity of liver disease in man, Gut. 14: 895–902, 1973.
33. POTTER, G. D. Bile acid diarrhea, Dig. Dis. 16: 118–124, 1998.
34. MILLARD, R. W., BAIG, H., and VATNER, S. F. Cardiovascular effects of radioactive microsphere suspensions and Tween 80 solutions, Am. J. Physiol. 232: H331–H334, 1977.
35. PAUMGARTNER, G. Serum bile acids: Physiological determinants and results in liver disease, J Hepatol. 2: 291–298, 1986.
36. DE CAESTECKER, J. S., JAXRAWI, R. P., NISBETT, J. A., JOSEPH, A. E. A., MAXWELL, J. D., and NORTHFIELD, T. C. Direct assessmant of the mechanism for a raised serum bile acid level in chronic liver disease, Eur. J. Gastroenterol. Hepatol. 7: 955–961, 1995.
37. FARKKILA, M. A., KAIREMO, K. J., TAAVITSAINEN, M. J., STANDBERG, T. A., and MIETTINEN, T. A. Plasma lathosterol as a screening test for bile acid malabsorption due to ileal resection: Correlation with 75SeHCAT test and faecal bile acid excretion, Clin. Sci. 90: 315–319, 1996.
38. RUDBURG, U. and NYLANDER, B. Radiological bile acid absorption test 75SeHCAT in patients with diarrhoea of unknown cause, Acta Radiol. 37: 672–675, 1996.
39. MILKIEWICZ, P., BAIOCCHI, L., MILLS, C. O., AHMED, M., KHALAF, H., KEOGH, A., BAKER, J., and ELIAS, E. Plasma clearance of cholyl-lysyl-fluorescein: A pilot study in humans, J Hepatol. 27: 1106–1109, 1997.
40. POPPER, H. Biology and Pathogiology. In: I. ARIAS, H. POPPER, D. SCHACTER, and A. A. SHAFRITZ (eds.), The Liver, pp. p. 771–773. New York: Raven Press, 1982.
41. SAWANMURA, T., NAKADA, H., HAZAMA, H., SHIOZAKI, Y., SAMESHIMA, Y., and TASHIRO, Y. Hyperasialoglycoproteinemia in patients with chronic liver diseases and/or liver cell carcinoma. Asialoglycoprotein receptor in cirrhosis and liver cell carcinoma, Gastroenterology. 87: 1217–1221, 1984.
42. LAUFFER, R. B., GREIF, W. L., STARK, D. D., VINCENT, A. C., SAINI, S., WEDEEN, V. J., and BRADY, T. J. Iron-EHPG as an hepatobiliary MR contrast agent: Intitial imaging and biodistribution studies, J Comput Assist Tomogr. 9: 431–438, 1985.
43. BENNESS, G., KHANGURE, M., MORRIS, I., WARWICK, A., BURROWS, P., VOGLER, H., and WEINMANN, H. J. Hepatic kinetics and magnetic resonance imaging of gadolinium-EOB_DTPA in dogs, Invest. Radiol. 31. 211–217, 1996.
44. SAINI, S., STARK, D. D., HAHN, P. F., WITTENBERG, J., BANDY, T. J., and FERRUCCI, J. T., JR. Ferrite particles: A superparamagnetic MR contrast agent for the reticuloendothelial system, Radiology. 162: 211–217, 1987.
45. EARP, H. S. and O'KEEFE, E. J. Epidemal growth factor receptor number decreases during rat liver regeneration, Clin. Invest. 67: 1580–1583, 1981.
46. BOCCHETTA, M., BRUSCALUPI, G., CASTELLANO, F., TRENTALANCE, A., KOMAROMY, M., FONG, L. G., and COOPER, A. D. Early induction of LDL receptor gene during rat liver regeneration, J. Cell. Physiol. 156: 601–609, 1993.
47. KATO, S., OTSU, K., OHTAKE, K., KIMURA, Y., YASHIRO, T., SUZUKI, T., and AKAMATSU, N. Concurrent changes in sinusoidal expression of laminin and affinity of hepatocytes to laminin during rat liver regeneration, Exp. Cell Res. 198: 59–68, 1992.
48. SCOTT, C. D. and BAXTER, R. C. Regulation of soluble insulin-like growth factor-II/mannose 6-phosphate receptor in hepatocytes from intact and regenerating rat liver, Endocrinology. 137: 3864–3870, 1996.
49. NAIR, B. G., STEINKE, L., YU, Y. M., RASHED, H. M., SEYER, J. M., and PATAEL, T. B. Increase in the number of atrial natriuretic hormone receptors in regenerating rat liver, J. Biol. Chem. 266: 567–573, 1991.
50. CHI, L., FARAJ, A., ALAOUI, A., GROMAN, E. V., RUTKOWSKI, J., JOSEPHSON, L., and SOMMA-DOSSI, J. -P. Arabinogalactan (9 kDa)-9-b-D-arabinofiranosyl-adenine-5'-monophosphate, a novel liver-targeted conjugate that selectively inhibits hepatitis B virus replication in vivo, Antiviral Chem. Chemotherapy. 8: 529–536, 1997.
51. SATO, S. B., SKO, Y., YAMASHINA, S., and OHNISHI, S. A. A novel method for isolating specific endocytic vesicles using very fine ferrite particles coated with biological ligands and the high-gradient magnetic separation technique, J Biochem (Tokyo). 100: 1481–1492, 1986.
52. REIMER, P., WEISSLEDER, R., WITTENBERG, J., and BRADY, T. J. Receptor-directed contrast agents for MR imaging: Preclinical evaluation with affinity assay., Radiology. 182: 565–569, 1992.
53. LEVEILE-WEBSTER, C. R., ROGERS, J., and ARIAS, I. M. Use of an asialoglycoprotein receptor-targeted magnetic resonance contrast agent to study changes in receptor biology during liver regeneration and endotoxemia in rats, Hepatology. 23: 1631–1641, 1996.
54. VERA, D. R., BUONOCORE, M. H., WISNER, E. R., KATZBERG, R. W., and STADALNIK, R. C. A molecular receptor-binding contrast agent for magnetic resonance imaging of the liver, Acta Radiol. 2: 497–506, 1995.

55. FUJIOKA, H., KAWASHITA, Y., KAMOHARA, Y., YAMASHITA, A., MIZOE, A., YAMAGUCHI, J., AZUMA, T., FURUI, J., and KANEMATSU, T. Utility of technetium-99m-labeled galactosyl human serum albumin scintigraphy for estimating the hepatic functional reserve, J. Clin. Gastroenterol. 28: 329–333, 1999.

56. KOKUDO, N., VERA, D. R., KOIZUMI, M., SEKI, M., SATO, T., STADALNIK, R. C., and TAKAHASHI, T. Recovery of hepatic asialoglycoprotein receptors after major hepatic resection, J. Nucl. Med. 40: 137–141, 1999.

57. PREVOT, A., SEMAMA, D. S., JUSTRABO, E., GUIGNARD, J. P., ESCOUSSE, A., and GOUYON, J. B. Actue cyclosporine A-induced nephrotoxicity: a rabbit model, Pediatric Nephrology. 14: 370–375, 2000.

58. EBERSTADT, P. L. Comparative study of glomerular filtration rate with diverse labelled agents, Inter Urology Nephr. 16: 3–11, 1984.

59. THLIVERIS, J. A., YATSCOFF, R. W., LUKOWSKI, M. P., COPELAND, K. R., JEFFERY, J. R., and MURPHY, G. F. Chronic ciclosporin nephrotoxicity: a rabbit model, Nephron. 57: 470–476, 1991.

60. JOSEPHSON, L., GROMAN, E.V., MENZ, E., LEWIS, J. M., and BENZEL, H. A. A functionalized superparamagentic iron oxide colloid as a receptor directed MR contrast agent.
Magn.Reson.Imaging 8: 637–646, 1990.

What is claimed is:

1. A method of determining the glomerular filtration rate (GFR) of a subject, comprising:
administering to the subject an amount of a test substance having at least one atom of a stable isotope of an element with a nucleus that captures a neutron and subsequently emits a photon, wherein the test substance is filtered by the kidneys and detected by neutron activation analysis of a sample of a bodily fluid;
obtaining at least one sample of a bodily fluid from the subject at least one predetermined time interval following administering the test substance;
determining an amount of the test substance in a volume of the at least one sample of the bodily fluid by neutron flux activation;
and calculating the GFR from the amount of photon emission by the activated element, thereby determining the GFR of the subject.

2. A method according to claim 1, wherein determining the amount of the test substance further involves comparing photon emission of the activated element in the sample of the bodily fluid to photon emission from a standard that includes the same stable isotope and is exposed to the same neutron flux.

3. A method according to claim 1, further comprising prior to administering the test substance to the subject, obtaining a sample from the subject of at least one bodily fluid for determining a baseline of concentration of the element.

4. A method according to claim 1, wherein the test substance is selected from the group consisting of Gd-DTPA, Sm-DTPA, La-DTPA, Eu-DTPA, Gd-DOTA, Sm-DOTA, La-DOTA, and Lu-DOTA.

5. A method according to claim 1, wherein the test substance is an iodinated contrast agent.

6. A method of determining the glomerular filtration rate (GFR) of a subject, comprising:
administering to the subject an amount of a test substance having at least one atom of a stable isotope of an element with a nucleus that captures a neutron and subsequently emits a photon, wherein the test substance is filtered by the kidneys and detected by neutron activation analysis of a sample of a bodily fluid;
obtaining at least one sample of a bodily fluid from the subject at least one predetermined time interval following administering the test substance;
determining an amount of the test substance in a volume of the at least one sample of the bodily fluid by neutron flux activation;
and calculating the GFR from the amount of photon emission by the activated element, thereby determining the GFR of the subject, wherein the test substance is an iodinated contrast agent that comprises iohexol or iothalamate.

7. A method according to claim 1, wherein a dose of the test substance administered to the subject is about one µmol to about 0.5 mmol per kg body weight of the subject.

8. A method according to claim 1, wherein the test substance is administered intravenously.

9. A method according to claim 1, wherein the time interval is about 10 to about 60 or about 180 minutes.

10. A method according to claim 1, wherein calculating the GFR further involves using a computerized program.

11. A method of determining the glomerular filtration rate (GFR) of a subject, comprising:
administering to the subject an amount of a test substance having at least one atom of a stable isotope of an element with a nucleus that captures a neutron and subsequently emits a photon, wherein the test substance is filtered by the kidneys and detected by neutron activation analysis of a sample of a bodily fluid;
obtaining at least one sample of a bodily fluid from the subject at least one predetermined time interval following administering the test substance;
determining an amount of the test substance in a volume of the at least one sample of the bodily fluid by neutron flux activation;
and calculating the GFR from the amount of photon emission by the activated element, thereby determining the GFR of the subject, wherein obtaining a sample from the subject further comprises catheterizing the urethra of the subject.

12. A method according to claim 1, wherein determining the amount by neutron flux activation further includes adding to the sample of the bodily fluid a monitor which is an internal standard for correcting for variation in neutron flux, wherein the monitor is a stable isotope of an element with a nucleus that captures a neutron and subsequently emits a photon.

13. A method according to claim 12, wherein calculating the GFR from the photon emission by the activated element is normalizing for the variation in neutron flux.

14. A method according to claim 12, wherein the test substance and the monitor are stable isotopes of elements with a nucleus that captures a neutron and subsequently emits a photon, and are different isotopes.

15. A method according to claim 12, wherein the test substance and the monitor are stable isotopes of elements with a nucleus that captures a neutron and subsequently emits a photon, and are different elements.

16. A method according to any of claims 12–13 and 14–15, wherein the stable isotope of each of the test substance and the monitor are selected from the group consisting of $^{36}S$, $^{45}Sc$, $^{50}Cr$, $^{51}V$, $^{55}Mn$, $^{58}Fe$, $^{59}Co$, $^{63}Cu$, $^{75}As$, $^{79}Br$, $^{81}Br$, $^{103}Rh$, $^{107}Ag$, $^{109}Ag$, $^{113}Cd$, $^{114}Cd$, $^{113}In$, $^{115}In$, $^{123}Te$, $^{121}Sb$, $^{123}Sb$, $^{123}Te$, $^{127}I$, $^{133}Cs$, $^{139}La$, $^{141}Pr$, $^{146}Nd$, $^{149}Sm$, $^{152}Sm$, $^{151}Eu$, $^{153}Eu$, $^{152}Gd$, $^{155}Gd$, $^{157}Gd$, $^{159}Tb$, $^{158}Dy$, $^{160}Dy$, $^{161}Dy$, $^{162}Dy$, $^{163}Dy$, $^{164}Dy$, $^{165}Ho$, $^{168}Yb$, $^{169}Tm$, $^{174}Hf$, $^{175}Yb$, $^{175}Lu$, $^{176}Lu$, $^{181}Ta$, $^{184}Os$, $^{185}Re$, $^{186}W$, $^{187}Re$, $^{190}Ir$, $^{190}Pt$, $^{193}Ir$, $^{196}Hg$, $^{206}Hg$, and $^{197}Au$.

* * * * *

UNITED STATES PATENT AND TRADEMARK OFFICE
CERTIFICATE OF CORRECTION

PATENT NO. : 7,048,907 B2　　　　　　　　　　　　　　　　　　　Page 1 of 1
APPLICATION NO. : 10/060,652
DATED : May 23, 2006
INVENTOR(S) : Groman et al.

It is certified that error appears in the above-identified patent and that said Letters Patent is hereby corrected as shown below:

Claim 4, column 83, line 56:　　delete "Eu-DTPA" and insert --Lu-DTPA--

Claim 16, column 84, line 64, between "$^{174}$Hf," and "$^{175}$Yb,":　　insert --$^{178}$Hf,--

Column 2, line 13:　　delete "$^{187}$Re, $^{187}$Re" and insert --$^{185}$Re, $^{187}$Re--

Column 4, line 38:　　delete "159Gd" and insert --$^{159}$Tb--

Column 4, line 40, between "$^{187}$Re," and "$^{193}$Ir,":　　insert --$^{190}$Ir,--

Column 22, line 4:　　delete "[Si]$_{SI}$" and insert --[SI]$_{SI}$--

Column 27, line 28:　　delete "10 million visits to physicians" and insert --50 million visits to physicians--

Column 35, line 42:　　delete "lest" and insert --test--

Column 58, line 30:　　delete "s$^{-2}$" and insert --s$^{-1}$--

Column 59, line 56:　　delete "ketanine" and insert --ketamine--

Signed and Sealed this

Fifteenth Day of August, 2006

JON W. DUDAS
*Director of the United States Patent and Trademark Office*